(12) United States Patent
Goldstein et al.

(10) Patent No.: US 9,187,487 B2
(45) Date of Patent: Nov. 17, 2015

(54) AZAINDOLE DERIVATIVES AS TYROSINE KINASE INHIBITORS

(75) Inventors: David M. Goldstein, Redwood City, CA (US); Kenneth Albert Brameld, Menlo Park, CA (US); Erik Verner, Belmont, CA (US)

(73) Assignee: PRINCIPIA BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 14/117,885

(22) PCT Filed: May 16, 2012

(86) PCT No.: PCT/US2012/038120
§ 371 (c)(1),
(2), (4) Date: Nov. 26, 2013

(87) PCT Pub. No.: WO2012/158785
PCT Pub. Date: Nov. 22, 2012

(65) Prior Publication Data
US 2014/0073626 A1 Mar. 13, 2014

Related U.S. Application Data

(60) Provisional application No. 61/486,988, filed on May 17, 2011.

(51) Int. Cl.
C07D 487/04 (2006.01)
A61K 45/06 (2006.01)
A61K 31/4985 (2006.01)
A61K 31/5377 (2006.01)

(52) U.S. Cl.
CPC .......... *C07D 487/04* (2013.01); *A61K 31/4985* (2013.01); *A61K 31/5377* (2013.01); *A61K 45/06* (2013.01)

(58) Field of Classification Search
CPC ............... C07D 487/04; A61K 45/06
See application file for complete search history.

(56) References Cited

U.S. PATENT DOCUMENTS

| 2008/0207613 A1 | 8/2008 | Styles et al. |
| 2009/0215750 A1 | 8/2009 | Bamberg et al. |
| 2009/0215788 A1 | 8/2009 | Elworthy et al. |
| 2011/0059118 A1 | 3/2011 | de Vicente Fidalgo et al. |

FOREIGN PATENT DOCUMENTS

| WO | 2004013091 | 2/2004 |
| WO | 2009062258 | 5/2009 |
| WO | 2009106441 | 9/2009 |
| WO | 2009106444 | 9/2009 |
| WO | 2009106445 | 9/2009 |
| WO | 2010014930 | 2/2010 |
| WO | 2011003418 | 1/2011 |
| WO | 2011144585 | 11/2011 |
| WO | 2012054364 | 4/2012 |

OTHER PUBLICATIONS

Rodgers et al., caplus an 2009:859320.*
Hsu et al., Journal of Immunology Research, vol. 2014, 2014, 7 pages.*
Legendre, Transplantation Research, 2013, 2, 5 pages.*
Spoerl, abstract, 2015, http://www.ncbi.nlm,nih.gov/pubmed/24711661.*
West, abstract, 2015, http://www.ncbi.nlm,nih.gov/pubmed/19431082.*
Honold et al., caplus an 2008:316754, 2008.*
Buzzetti, F., et al., Cinnamamide analogs as inhibitors of protein tyrosine kinases, Il Farmaco, 1993, 48(5): 615-636.
Donald, A., et al., Rapid evolution of 6-phenylpurine inhibitors of protein kinase B through structure-based design, J. Med. Chem., 2007, 50: 2289-2292.
Gu, L., et al., Combinatorial approach to identification of tyrphostin inhibitors of sytokine signaling, Bioorganic & Medicinal Chemistry, 2005, 13: 4269-4278.
Kakehi, A., et al., Synthesis using allylidenedihydropyridines I. convenient systhesis of 3-ethenylpyrazolo[1,5-a] pyridines, 1977, Chemistry Letters: 545-546.
Kakehi, A., et al., Synthesis using allylidenedihydropyridines. VIII. facile preparation of 2-alkylthio-3-vinylpyrazolo[1,5-a]pyridines, Bull. Chem. Soc. Jpn., 1980, 53: 1775-1776.
Kamath, S., et al., Receptor-guided alignment-based comparative 3D-QSAR studies of benzylidence malonitrile tyrphostins as EGFR and HER-2 kinase inhibitors, J. Med. Chem., 2003, 46: 4657-4668.
Patch, R. J., et al., Identification of diaryl ether-based ligands for estrogen-related receptor a as potential antidiabetic agents, J. Med. Chem., 2011, 54: 788-808.
Patent Cooperation Treaty, International Search Report and Written Opinion issued for PCT/US2012/038120, mailed Aug. 20, 2014, 13 pages.
Meydan, N., et al., Inhibition of acute lymphoblastic leukaemia by a Jak-2 inhibitor, Letters to Nature, 1996, 379L 645-648.
Ghoreschi, K., et al., Janus kinases in immune cell signaling; Immunological Review, 2009, 228: 273-287.

* cited by examiner

Primary Examiner — Sun Jae Yoo
(74) Attorney, Agent, or Firm — Bryan Cave LLP

(57) ABSTRACT

The present disclosure provides compounds and pharmaceutically acceptable salts that are tyrosine kinase inhibitors, in particular BLK, BMX, EGFR, HER2, HER4, ITK, JAK3, TEC, Btk, and TXK and are therefore useful for the treatment of diseases treatable by inhibition of tyrosine kinases such as cancer and inflammatory diseases such as arthritis, and the like. Also provided are pharmaceutical compositions containing such compounds and pharmaceutically acceptable salts and processes for preparing such compounds and pharmaceutically acceptable salts.

23 Claims, No Drawings

AZAINDOLE DERIVATIVES AS TYROSINE KINASE INHIBITORS

The present disclosure provides compounds and pharmaceutically acceptable salts thereof that are tyrosine kinase inhibitors, in particular BLK, BMX, EGFR, HER2, HER4, ITK, JAK3, TEC, BTK, and TXK and are therefore useful for the treatment of diseases treatable by inhibition of tyrosine kinases such as cancer and inflammatory diseases such as arthritis, and the like. Also provided are pharmaceutical compositions containing such compounds and processes for preparing such compounds.

The human genome contains at least 500 genes that encode for protein kinases. Many of these kinases have been implicated in human disease and as such represent potentially attractive therapeutic targets. For example EGFR is overexpressed in breast, head and neck cancers and the overexpression is correlated with poor survival (see Do N. Y., et al., Expression of c-erbB receptors, MMPs and VEGF in squamous cell carcinoma of the head and neck. *Oncol Rep*. August 12:229-37. 2004 and Foley J, et al. EGFR signaling in breast cancer: bad to the bone. *Semin Cell Dev Biol.* 21:951-60. 2010). Her2, another EGFR family member, also is amplified or overexpressed in up to 30% of breast cancers, also correlating with poor survival (see Murphy C. G, Modi S. HER2 breast cancer therapies: a review. *Biologics* 3:289-301. 2009). HER4, also in the EGFR family, is overexpressed in head and neck squamous cell carcinomas (4). Other studies show decreased expression of HER4 in certain cancers and suggest tumor suppressor activity (see Thomasson M, et al., ErbB4 is downregulated in renal cell carcinoma—a quantitative RT-PCR and immunohistochemical analysis of the epidermal growth factor receptor family. *Acta Oncol.* 43:453-9. 2004). Overall the data support a role for members of the EGFR family in cancer. ITK, a member of the TEC kinase family, is involved in activation of T cells and mast cells (see Iyer A. S. et al. Absence of Tec Family Kinases Interleukin-2 Inducible T cell Kinase (Itk) and Bruton's Tyrosine Kinase (Btk) Severely Impairs Fc {epsilon}RI-dependent Mast Cell Responses. *J Biol Chem.* 286:9503-13. 2011) and is a potential target in inflammatory immune diseases such as asthma. Mice deficient in ITK are resistant to development of allergic asthma (see Sahu N, et al., Differential sensitivity to Itk kinase signals for T helper 2 cytokine production and chemokine-mediated migration. *J. Immunol.* 180:3833-8. 2008). Another family member, BMX, is involved in supporting tumor angiogenesis though it's role in the tumor vascular endothelium (see Tu T, et al., Bone marrow X kinase-mediated signal transduction in irradiated vascular endothelium. *Cancer Res.* 68:2861-9. 2008) and is also progressively up-regulated during bladder cancer progression (see Guo S, et al., Tyrosine Kinase ETK/BMX Is Up-Regulated in Bladder Cancer and Predicts Poor Prognosis in Patients with Cystectomy. *PLoS One.* 6:e17778.2011) suggesting a potential therapeutic target in this type cancer. Bruton's tyrosine kinase (BTK) has strong pre-clinical validation in rheumatoid arthritis (RA), systemic lupus erythematosus and lymphoma (see Honigberg L A, et al. The Bruton tyrosine kinase inhibitor PCI-32765 blocks B-cell activation and is efficacious in models of autoimmune disease and B-cell malignancy. Proc Natl Acad Sci USA. 107:13075-80. 2010). The B lymphoid kinase (BLK) is linked through genetic association with a variety of rheumatic diseases including systemic lupus erythematosus and systemic sclerosis (see Ito I, et al., Association of the FAM167A-BLK region with systemic sclerosis. *Arthritis Rheum.* 62:890-5. 2010).

JAK3 is a cytoplasmic tyrosine kinase that functions downstream of the common gamma chain receptor subunit for cytokine signaling. It is crucial for signal transduction in response to stimulation by IL-2, IL-4, IL-5, Il-7, IL-9, and IL-21 (see Shuai K and Liu B. Regulation of JAK-STAT signaling in the immune system. *Nat Rev Immunol.* 3:900-11. 2003 and O'Shea J J, et al. A new modality for immunosuppression: targeting the JAK/STAT pathway. *Nat Rev Drug Discov.* 3:555-64. 2004). The expression of JAK3 is restricted to mainly lymphoid and myeloid cells in contrast to the other Jak family members, which are more ubiquitously expressed (see Johnston J A, et al. Phosphorylation and activation of the Jak-3 Janus kinase in response to interleukin-2. *Nature.* 370: 151-3. 1994). This makes JAK3 an attractive target for immunosuppression. JAK3 null humans have a severe combined immunodeficiency disease (SCID). These individuals display lack of circulating T and NK cells with normal numbers of B cells (see Pesu M, et al. JAK3, severe combined immunodeficiency, and a new class of immunosuppressive drugs. *Immunol Rev.* 203:127-42. 2005). In mice, JAK3 deficiency results in not only T and NK cell depletion, but B cells as well (see Pesu M, et al. JAK3, severe combined immunodeficiency, and a new class of immunosuppressive drugs. *Immunol Rev.* 203: 127-42. 2005). CP-690-550, a pan Jak inhibitor, blocks the mixed lymphocyte reaction (MLR) (see Kudlacz E, et al. The novel JAK-3 inhibitor CP-690550 is a potent immunosuppressive agent in various murine models. *Am J Transplant.* 4:51-7. 2004), the delayed-type hypersensitivity response (DTH) (see Kudlacz E, et al. The novel JAK-3 inhibitor CP-690550 is a potent immunosuppressive agent in various murine models. *Am J Transplant.* 4:51-7. 2004), as well as the collagen-induced arthritis model (see Milici A J, et al. Cartilage preservation by inhibition of Janus kinase 3 in two rodent models of rheumatoid arthritis. *Arthritis Res Ther.* 10:R14 1-9. 2008). Other Jak family members include Jak2, which is involved in hematopoietic growth factor signaling, and Jak1 and Tyk2 which in combination with Jak2 are important for interferon signaling and contribute to host resistance (see Shuai K and Liu B. Regulation of JAK-STAT signaling in the immune system. *Nat Rev Immunol.* 3:900-11. 2003).

Compounds that target the Jak pathway are in clinical development, but none is selective for a single Jak family member. However, these studies provide clinical validation of the Jak pathway in rheumatoid arthritis (see Krenmer J, et al. The oral Jak inhibitor CP-690,550 in combination with methotrexate is efficacious, safe and well tolerated in patients with active rheumatoid arthritis with an inadequate response to methotrexate alone. *Arthritis & Rheum.* 58:4030a. 2008). Improvements in disease activity are observed as early as 1 week after initiation of treatment with significant improvements in ACR20, ACR50 and ACR70 as early as 4 weeks. The current disclosure which targets JAK3 selectively should have significant improvements over other compounds in clinical development due to improvements in the safety profile. Other clinical applications for JAK3 inhibition include kidney transplantation, Crohn's disease, psoriasis, and JAK3-dependent hematopoietic malignancies (see Ghoreschi K, et al., Janus kinases in immune cell signaling. *Immunol Rev.* 228:273-87. 2009). A short-term study with CP-690,550 on psoriasis patients demonstrated efficacy, suggesting possible utility in this indication (see Boy M G, et al. Double-blind, placebo-controlled, dose-escalation study to evaluate the pharmacologic effect of CP-690,550 in patients with psoriasis. *J Invest Dermatol.* 129:2299-302. 2009).

Accordingly, there is a need for compounds that inhibit tyrosine kinases thereby providing treatment for diseases such as autoimmune diseases, thromboembolic diseases and cancer. The present disclosure can fulfill this need and related needs.

In one aspect, this disclosure is directed to a compound of Formula (IA) or a pharmaceutically acceptable salt thereof:

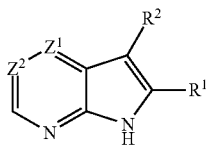

(IA)

wherein:

$Z^1$ is N or $CR^3$;

$Z^2$ is N or $CR^4$ provided that at least one of $Z^1$ and $Z^2$ is N and both $Z^1$ and $Z^2$ are not simultaneously N;

$R^1$ is hydrogen, alkyl, halo, haloalkyl, haloalkoxy, cyano or cycloalkyl; and (i) when $Z^1$ is $CR^3$ where $R^3$ is hydrogen, alkyl, halo, haloalkyl, haloalkoxy, cyano, cycloalkyl, or a ring of formula (A):

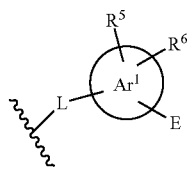

(A)

then, $R^2$ is hydrogen, alkyl, halo, haloalkyl, haloalkoxy, cyano, cycloalkyl, or a ring of formula (B):

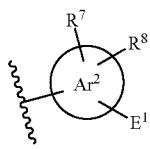

(B)

provided at least one ring of formula (A) and (B) is present and not both rings of formula (A) and (B) are present simultaneously; and (ii) when $Z^2$ is $CR^4$ where $R^4$ is a ring of formula (C):

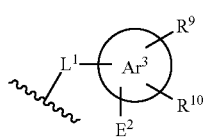

(C)

then, $R^2$ is hydrogen, alkyl, cycloalkyl, halo, cyano, acyl, or aminocarbonyl; and wherein:

L and $L^1$ are independently bond, —CH$_2$—, —NR—, —O—, CO, —S(O)$_n$— (where n is 0-2), —NRCO—, —CONR—, or heteroalkylene (where R is hydrogen, alkyl or cycloalkyl);

$Ar^1$, $Ar^2$ and $Ar^3$ are independently aryl, heteroaryl, cycloalkyl or heterocyclyl;

$R^5$, $R^7$, $R^8$ and $R^9$ are independently hydrogen, alkyl, alkoxy, halo, haloalkyl, haloalkoxy, cyano or cycloalkyl;

$R^6$ and $R^{10}$ are independently hydrogen, alkyl, alkoxy, halo, haloalkyl, haloalkoxy, cyano, cycloalkyl, hydroxyalkoxy, alkoxyalkoxy, aminoalkoxy, or alkylsulfonylalkoxy;

E and $E^2$ are independently:

(i) —P—CH=C($R^b$)(EWG) where P is a bond, $NR^a$ (where $R^a$ is hydrogen or alkyl), —O—, —S—, —S(O)—, —S(O$_2$)—, alkylene or heteroalkylene, $R^b$ is cyano, nitro, halo, haloalkyl, haloalkoxy, alkylthio, or alkylsulfonyl and EWG is an electron withdrawing group; or (ii) —Z'-(EWG')-C($R^b$)=CHR$^c$ where Z' is bond, $NR^a$ (where $R^a$ is hydrogen or alkyl), —O—, —S—, —S(O)—, —S(O$_2$)—, alkylene, or heteroalkylene, EWG' is a bond or an electron withdrawing group, $R^b$ is cyano, nitro, halo, haloalkyl, haloalkoxy, alkylthio, or alkylsulfonyl and $R^c$ is alkyl, substituted alkyl, haloalkoxy, cycloalkyl, cycloalkyleneNR$^d$R$^e$ where $R^d$ and $R^e$ are independently hydrogen, alkyl, or cycloalkyl; or (iii) a group of formula (a) or (b);

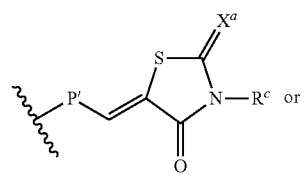

(a)

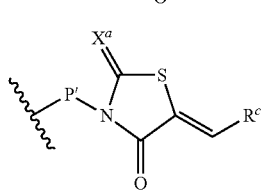

(b)

where P' is bond, alkylene or heteroalkylene, $X^a$ is O or N(H or alkyl) and $R^c$ is hydrogen, alkyl, substituted alkyl, haloalkoxy, cycloalkyl, or cycloalkyleneNR$^d$R$^e$ where $R^d$ and $R^e$ are independently hydrogen, alkyl, or cycloalkyl; and $E^1$ is:

(i) —P-Q-CH=C($R^b$)(EWG) where P is a bond, $NR^a$ (where $R^a$ is hydrogen or alkyl), —O—, —S—, —S(O)—, —S(O$_2$)—, alkylene or heteroalkylene, Q is a bond, aryl or heteroaryl wherein the aryl or heteroaryl ring is substituted with one or two substituents independently selected from hydrogen, alkyl, halo, haloalkyl, or haloalkoxy, $R^b$ is cyano, nitro, halo, haloalkyl, haloalkoxy, alkylthio, or alkylsulfonyl and EWG is an electron withdrawing group; or (ii) —Z-(EWG')-C($R^b$)=CHR$^c$ where Z is bond, $NR^a$ (where $R^a$ is hydrogen or alkyl), —O—, —S—, —S(O)—, —S(O$_2$)—, alkylene, cycloalkylene, heteroalkylene, —(Z$^a$)$_{n1}$-aryl, or —(Z$^a$)$_{n1}$-heteroaryl (wherein n1 is 0 or 1, $Z^a$ is $NR^a$ (where $R^a$ is hydrogen or alkyl), —O—, —S—, —S(O)—, —S(O$_2$)—, alkylene, or heteroalkylene and aryl or heteroaryl is optionally substituted with one or two substituents independently selected from hydrogen, halo, alkyl, alkoxy, alkylthio, haloalkyl, or haloalkoxy), EWG' is a bond or an electron withdrawing group, $R^b$ is cyano, nitro, halo, haloalkyl, haloalkoxy, alkylthio, or alkylsulfonyl and $R^c$ is alkyl, substituted alkyl, haloalkoxy, cycloalkyl, cycloalkyleneNR$^d$R$^e$ where $R^d$ and $R^e$ are independently hydrogen, alkyl, or cycloalkyl; or (iii) a group of formula (c) or (d);

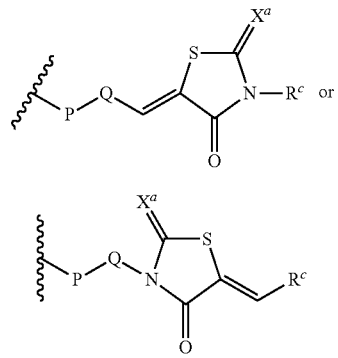

where P and Q are as defined above, $X^a$ is O or N(H or alkyl) and $R^c$ is hydrogen, alkyl, substituted alkyl, haloalkoxy, cycloalkyl, or cycloalkyleneNR$^d$R$^e$ where $R^d$ and $R^e$ are independently hydrogen, alkyl, or cycloalkyl;

provided the compound of Formula (I) is not:

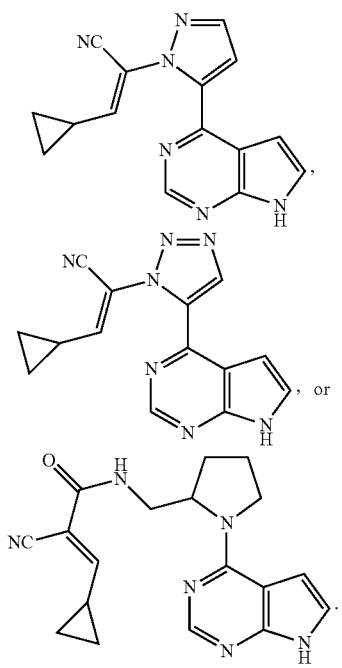

In another aspect, this disclosure is directed to a compound of Formula (I) or a pharmaceutically acceptable salt thereof:

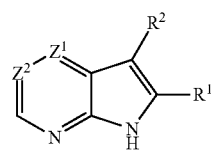

wherein:
$Z^1$ is N or $CR^3$;
$Z^2$ is N or $CR^4$ provided that at least one of $Z^1$ and $Z^2$ is N and both $Z^1$ and $Z^2$ are not simultaneously N;

$R^1$ is hydrogen, alkyl, halo, haloalkyl, haloalkoxy, cyano or cycloalkyl; and (i) when $Z^1$ is $CR^3$ where $R^3$ is hydrogen, alkyl, halo, haloalkyl, haloalkoxy, cyano, cycloalkyl, or a ring of formula (A):

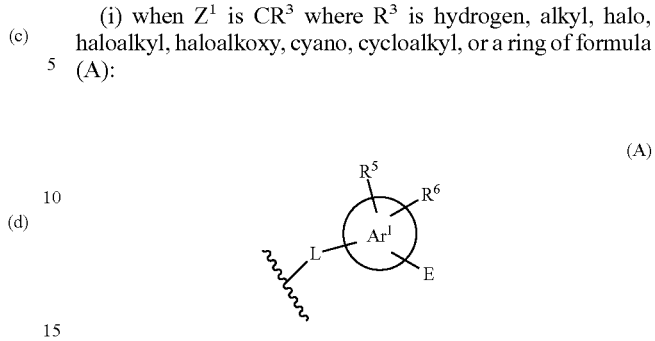

then, $R^2$ is hydrogen, alkyl, halo, haloalkyl, haloalkoxy, cyano, cycloalkyl, or a ring of formula (B):

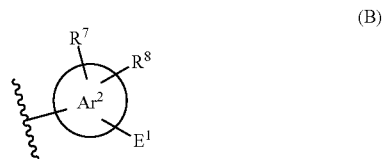

provided at least one ring of formula (A) and (B) is present and not both rings of formula (A) and (B) are present simultaneously; and (ii) when $Z^2$ is $CR^4$ where $R^4$ is a ring of formula (C):

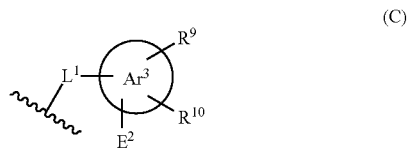

then, $R^2$ is hydrogen, alkyl, cycloalkyl, halo, cyano, acyl, or aminocarbonyl; and wherein:

L and $L^1$ are independently bond, —NR—, —O—, CO, —S(O)$_n$— (where n is 0-2), —NRCO—, —CONR—, or heteroalkylene (where R is hydrogen, alkyl or cycloalkyl);

$Ar^1$, $Ar^2$ and $Ar^3$ are independently aryl, heteroaryl, cycloalkyl or heterocyclyl;

$R^5$, $R^6$, $R^7$, $R^8$, $R^9$ and $R^{10}$ are independently hydrogen, alkyl, alkoxy, halo, haloalkyl, haloalkoxy, cyano or cycloalkyl;

E and $E^2$ are independently:

(i) —P—CH=C($R^b$)(EWG) where P is a bond, NR$^a$ (where $R^a$ is hydrogen or alkyl), —O—, —S—, —S(O)—, —S(O$_2$)—, alkylene or heteroalkylene, $R^b$ is cyano, nitro, halo, haloalkyl, haloalkoxy, alkylthio, or alkylsulfonyl and EWG is an electron withdrawing group; or (ii) —Z'-(EWG')-C($R^b$)=CHR$^c$ where Z' is bond, NR$^a$ (where $R^a$ is hydrogen or alkyl), —O—, —S—, —S(O)—, —S(O$_2$)—, alkylene, or heteroalkylene, EWG' is a bond or an electron withdrawing group, $R^b$ is cyano, nitro, halo, haloalkyl, haloalkoxy, alkylthio, or alkylsulfonyl and $R^c$ is alkyl, substituted alkyl, haloalkoxy, cycloalkyl, cycloalkyleneNR$^d$R$^e$ where $R^d$ and $R^e$ are independently hydrogen, alkyl, or cycloalkyl; or (iii) a group of formula (a) or (b);

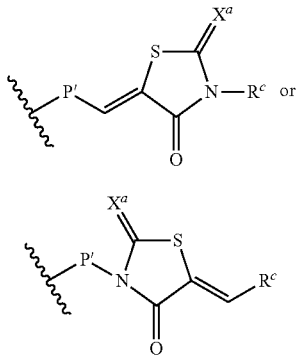

where P' is bond, alkylene or heteroalkylene, $X^a$ is O or N(H or alkyl) and $R^c$ is hydrogen, alkyl, substituted alkyl, haloalkoxy, cycloalkyl, or cycloalkyleneNR$^d$R$^e$ where R$^d$ and R$^e$ are independently hydrogen, alkyl, or cycloalkyl; and $E^1$ is:

(i) —P-Q-CH=C(R$^b$)(EWG) where P is a bond, NR$^a$ (where R$^a$ is hydrogen or alkyl), —O—, —S—, —S(O)—, —S(O$_2$)—, alkylene or heteroalkylene, Q is a bond, aryl or heteroaryl wherein the aryl or heteroaryl ring is substituted with one or two substituents independently selected from hydrogen, alkyl, halo, haloalkyl, or haloalkoxy, R$^b$ is cyano, nitro, halo, haloalkyl, haloalkoxy, alkylthio, or alkylsulfonyl and EWG is an electron withdrawing group; or (ii) —Z-(EWG')-C(R$^b$)=CHR$^c$ where Z is bond, NR$^a$ (where R$^a$ is hydrogen or alkyl), —O—, —S—, —S(O)—, —S(O$_2$)—, alkylene, cycloalkylene, heteroalkylene, —(Z$^a$)$_{n1}$-aryl, or —(Z$^a$)$_{n1}$-heteroaryl (wherein n1 is 0 or 1, Z$^a$ is NR$^a$ (where R$^a$ is hydrogen or alkyl), —O—, —S—, —S(O)—, —S(O$_2$)—, alkylene, or heteroalkylene and aryl or heteroaryl is optionally substituted with one or two substituents independently selected from hydrogen, halo, alkyl, alkoxy, alkylthio, haloalkyl, or haloalkoxy), EWG' is a bond or an electron withdrawing group, R$^b$ is cyano, nitro, halo, haloalkyl, haloalkoxy, alkylthio, or alkylsulfonyl and R$^c$ is alkyl, substituted alkyl, haloalkoxy, cycloalkyl, cycloalkyleneNR$^d$R$^e$ where R$^d$ and R$^e$ are independently hydrogen, alkyl, or cycloalkyl; or (iii) a group of formula (c) or (d);

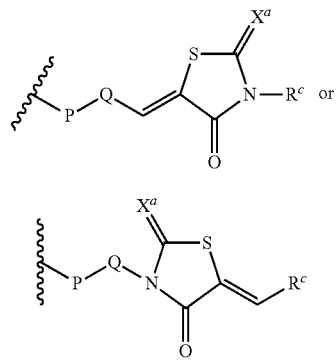

where P and Q are as defined above, $X^a$ is O or N(H or alkyl) and R$^c$ is hydrogen, alkyl, substituted alkyl, haloalkoxy, cycloalkyl, or cycloalkyleneNR$^d$R$^e$ where R$^d$ and R$^e$ are independently hydrogen, alkyl, or cycloalkyl;

provided the compound of Formula (I) is not:

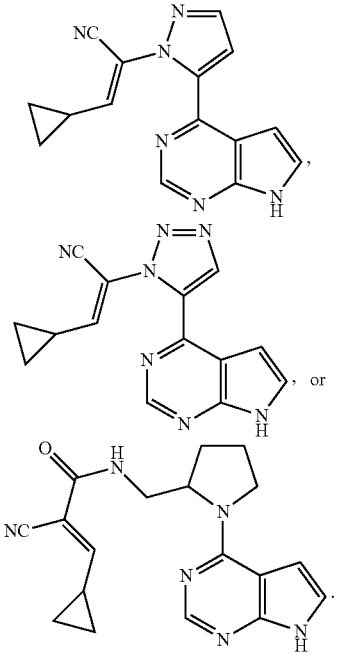

In one embodiment, in the compound of Formula (IA) and (I), when $L^1$ is a bond, Ar$^1$ is not pyrazolyl, triazolyl or pyrrolidinyl each ring substituted as provided therein.

In a second aspect, this disclosure is directed to a pharmaceutical composition comprising a compound of Formula (IA), (I) (or any of the embodiments thereof described herein), or a pharmaceutically acceptable salt thereof; and a pharmaceutically acceptable excipient.

In a third aspect, this disclosure is directed to a method of treating a disease treatable by inhibition of a tyrosine kinase, preferably JAK3, in a patient which method comprises administering to the patient in need thereof, a pharmaceutical composition comprising a compound of Formula (IA), (I) (or any of the embodiments thereof described herein) or a pharmaceutically acceptable salt thereof and a pharmaceutically acceptable excipient In one embodiment of this aspect, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. Preferably, the disease is rheumatoid arthritis. Preferably, the autoimmune disease is lupus. Preferably, the autoimmune disease is psoriasis or transplant. In another embodiment of this aspect, the patient in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In another embodiment of this aspect, the patient in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In another embodiment of this aspect, the patient is suffering from inflammatory skin disease which includes, by way of example, dermatitis, contact dermatitis, eczema, urticaria, rosacea, and scarring psoriatic lesions in the skin, joints, or other tissues or organs.

In yet another embodiment of this aspect, the subject in need is suffering from a cancer. In some embodiments, the compound of Formula (IA), (I) (or any embodiments thereof described herein) is administered in combination with another an anti-cancer agent e.g., the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, LY294002, Nexavar®, Tarceva®, Sutent®, Tykerb®, Sprycel®, Crizotinib, or Xalkori®.

In yet another embodiment, the patient in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a fourth aspect, the disclosure is directed to use of compound of Formula (IA), (I) (and any embodiments thereof described herein) for use as a medicament. In one embodiment, the use of compound of Formula (IA), (I) (and any embodiments thereof described herein) is for treating inflammatory disease or proliferative diseases.

In a fifth aspect, is the use of a compound of Formula (IA), (I) (and any embodiments thereof described herein) in the manufacture of a medicament for treating an inflammatory disease in a patient in which the activity of a tyrosine kinase such as BLK, BMX, EGFR, HER2, HER4, ITK, JAK3, TEC, Btk, and TXK, preferably, JAK3 contributes to the pathology and/or symptoms of the disease. In another embodiment of this aspect, the inflammatory disease is respiratory, cardiovascular, or proliferative diseases.

In any of the aforementioned aspects involving the treatment of proliferative disorders, including cancer, are further embodiments comprising administering the compound of Formula (IA), (I) (and any embodiments thereof described herein) in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, paclitaxel, Taxol™, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol. When combination therapy is used, the agents can be administered simultaneously or sequentially.

Definitions

Unless otherwise stated, the following terms used in the specification and claims are defined for the purposes of this application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxy" means an —OR radical where R is alkoxyalkyl as defined above. Representative examples include, but are not limited to, 2-methoxyethyloxy, 3-methoxypropyloxy, and the like. "Alkoxycarbonyl" means a —C(O)OR radical where R is alkyl as defined above, e.g., methoxycarbonyl, ethoxycarbonyl, and the like.

"Aminocarbonyl" means a —CONRR' radical where R is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the cycloalkyl, aryl, heteroaryl or heterocyclyl ring either alone or part of another group such as aralkyl, is optionally substituted with one, two, or three substituents independently selected from alkyl, halo, haloalkyl, haloalkoxy, alkoxy, cyano, carboxy, hydroxyl, —CONRR' (where R and R' are hydrogen or alkyl) alkylcarbonyl, alkylthio, or alkylsulfonyl, e.g., —CONH$_2$, methylaminocarbonyl, 2-dimethylaminocarbonyl, and the like.

"Aminosulfonyl" means a —SO$_2$NRR' radical where R is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the aryl, heteroaryl or heterocyclyl ring either alone or part of another group such as aralkyl, is optionally substituted with one, two, or three substituents independently selected from alkyl, halo, haloalkyl, haloalkoxy, alkoxy, cyano, carboxy, hydroxyl, alkylthio, or alkylsulfonyl, e.g., —SO$_2$NH$_2$, methylaminosulfonyl, dimethylaminosulfonyl, and the like.

"Aminoalkyloxy" means an —O-(alkylene)NRR' radical where R and R' are independently hydrogen or alkyl or R and R' together with the nitrogen atom to which they are attached form a saturated, monocyclic 4 to 7 membered ring in which one additional ring atom is optionally N, O or S(O)n where n is 0-2 and the ring is optionally substituted with one or two alkyl and where alkylene is as defined above. Representative examples include, but are not limited to, 2-aminoethyloxy, 3-aminopropyloxy, 2-methylaminoethyloxy, 3-methylaminopropyloxy, 2-dimethylaminoethyloxy, 3-dimethylaminopropyloxy, 2-diethylaminoethyloxy, 3-diethylaminopropyloxy, 2-piperidin-1-ylethyloxy, 3-piperidin-1-ylpropyloxy, 2-piperazin-1-ylethyloxy, 3-piperazin-1-ylpropyloxy, 2-(4-methylpiperazin-1-yl)ethyloxy, 3-(4-methylpiperazin-1-yl)propyloxy, 2-(4-ethylpiperazin-1-yl)ethyloxy, 3-(4-ethylpiperazin-1-yl)propyloxy, 2-morpholin-4-ylethyloxy, 3-morpholin-4-ylpropyloxy, and the like.

"Alkylsulfonylalkyloxy" means an —O-(alkylene)-SO$_2$R where R is alkyl where alkylene and alkyl are as defined above. Representative examples include, but are not limited to, 2-methylsulfonylethyloxy, 3-methylsulfonylpropyloxy, and the like.

"Acyl" means a —COR radical where R is alkyl, substituted alkyl, haloalkyl, cycloalkyl, cycloalkylalkyl, aryl, aralkyl, heteroaryl, heteroaralkyl, heterocyclyl, or heterocyclylalkyl, each as defined herein and wherein the cycloalkyl, aryl, heteroaryl or heterocyclyl ring either alone or part of another group such as aralkyl, is optionally substituted with one, two, or three substituents independently selected from alkyl, halo, haloalkyl, haloalkoxy, alkoxy, cyano, carboxy, hydroxyl, —CONRR' (where R and R' are hydrogen or alkyl), alkylcarbonyl, alkylthio, or alkylsulfonyl, e.g., acetyl, propionyl, benzoyl, pyridinylcarbonyl, and the like. When R is alkyl, the radical is also referred to herein as alkylcarbonyl.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Cycloalkylene" means a divalent cyclic saturated hydrocarbon radical of three to ten carbon atoms wherein one or two carbon atoms may be replaced by an oxo group, e.g., cyclopropylene, cyclobutylene, cyclopentylene, or cyclohexylene, and the like.

"Carboxy" means —COOH.

The term "electron withdrawing group" refers to a chemical substituent that modifies the electrostatic forces acting on a nearby chemical reaction center by withdrawing negative charge from that chemical reaction center. Thus, electron withdrawing groups draw electrons away from a reaction center. As a result, the reaction center is fractionally more positive than it would be in the absence of the electron-withdrawing group. In some embodiments, the chemical reaction center is one of the two carbons forming the carbon-carbon double bond (olefin). In some embodiments, the chemical reaction center is the olefin carbon attached to EWG. The electron withdrawing group functions to draw charge or electrons away from this olefin carbon thereby making the olefin carbon electron deficient (relative to the absence of the electron withdrawing group). The electron deficient olefin carbon is thereby rendered more reactive toward electron rich chemical groups, such as the sulfhydryl of a kinase active site cysteine.

Some non-limiting examples of EWG include, but are not limited to, —N(R'$_3$)$^+$, —SO$_3$H, —SO$_3$R', —S(O$_2$)R', —S(O)R', —C(O)NH$_2$, —C(O)NHR$^g$, —C(O)NR$^f$R$^g$, —S(O$_2$)NH$_2$, —SO$_2$NHR$^h$, —SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)OR')OR", halo, heteroaryl, or aryl; wherein X' is independently halogen (e.g. chloro of fluoro), R', R", R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached from heterocycloamino; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, EWG is —CO—NR$^f$R$^g$, —SO$_2$NR$^h$R$^i$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and R$^h$ and R$^i$ together with the nitrogen atom to which they are attached from heterocycloamino), aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, or pyridinyl N-oxide optionally substituted as defined in previous paragraph.

Some non-limiting examples of EWG' include, but are not limited to, —CH(haloalkyl), —NR'—, —S(O$_2$), —S(O), —CO—, —NR'CO—, —NR'SO$_2$—, —PO(OR')—,

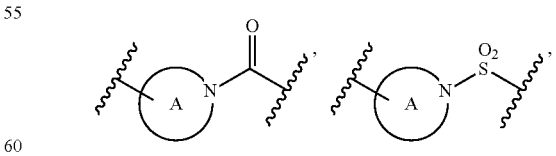

heteroaryl, or aryl; wherein each R' is independently hydrogen, alkyl, substituted alkyl, cycloalkyl; ring A is heterocycloamino where the carbonyl and sulfonyl groups are attached to —C(R$^b$)═CHR$^c$ in the definition of R$^1$ and R$^5$ in compound of Formula (I); and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, the heteroaryl ring is pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, or pyridinyl N-oxide optionally substituted as defined in previous paragraph.

In some embodiments, a composition of the present disclosure comprises a compound corresponding to Formula (I) (or a pharmaceutically acceptable salt thereof) in which E is —Z-(EWG')-C($R^b$)=$CHR^c$ or $E^1$ or $E^2$ is —Z'-(EWG')-C ($R^b$)=$CHR^c$ group, Z is a bond, and the ring $Ar^1$, $Ar^2$ and $Ar^3$ in the compound of Formula (I) to which E, $E^1$ and $E^2$ is attached respectively, possess an electron deficient π system. In such embodiments, the —C($R^b$)=$CHR^c$ group can be directly attached to the $Ar^1$, $Ar^2$ and $Ar^3$ ring in the compound of Formula (I). In general, a ring has an electron deficient π system when it is substituted with an electron withdrawing group or the ring itself is electron deficient, e.g., a heteroaryl ring containing an electronegative ring atom such as nitrogen, oxygen or sulfur. For example, in the compounds of Formula (I), when $Ar^1$, $Ar^2$ or $Ar^3$ is phenyl, the phenyl ring can be electron deficient when it is substituted with an electron withdrawing group such as halo, cyano, or haloalkyl. By way of further example, the $Ar^1$, $Ar^2$ or $Ar^3$ ring can also be an electron deficient π system when it is heteroaryl, e.g.,

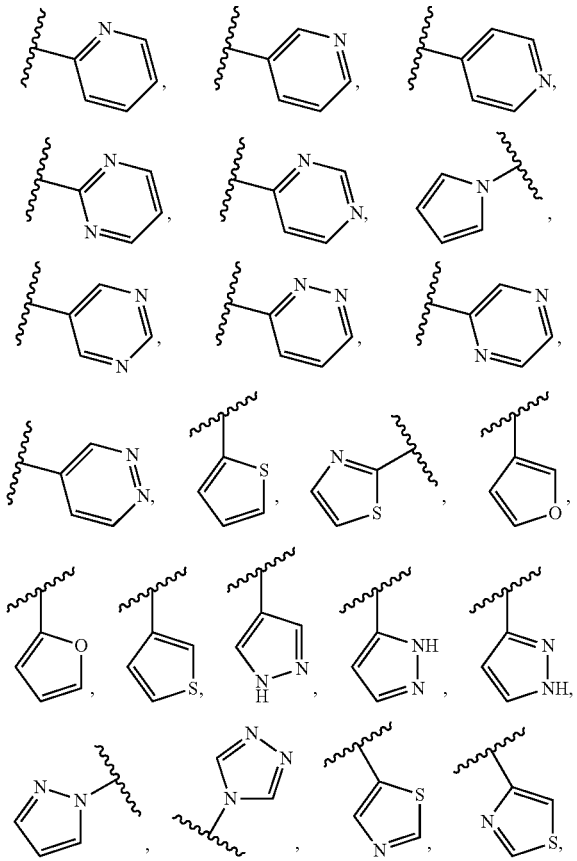

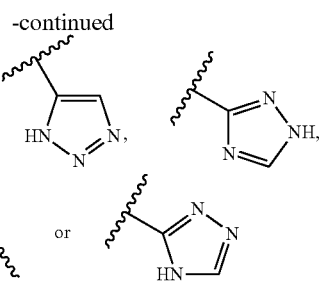

Each optionally substituted as defined above.

"Halo" means fluoro, chloro, bromo, or iodo, preferably fluoro or chloro.

"Haloalkyl" means alkyl radical as defined above, which is substituted with one or more halogen atoms, preferably one to five halogen atoms, preferably fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the alkyl is substituted with only fluoro, it is referred to in this application as fluoroalkyl.

"Haloalkoxy" means a —OR radical where R is haloalkyl as defined above e.g., —$OCF_3$, —$OCHF_2$, and the like. When R is haloalkyl where the alkyl is substituted with only fluoro, it is referred to in this application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkoxy" or "hydroxyalkyloxy" means a —OR radical where R is hydroxyalkyl as defined above. Representative examples include, but are not limited to, 2-hydroxyethyloxy, 3-hydroxypropyloxy, and the like.

"Heterocyclyl" means a saturated or unsaturated monovalent monocyclic group of 4 to 8 ring atoms in which one or two ring atoms are heteroatom selected from N, O, or S(O)$_n$—, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocyclylalkyl" means a -(alkylene)-R radical where R is heterocyclyl ring as defined above e.g., tetrahydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocyloamino ring can optionally be substituted with one, two, or three substituents independently selected from alkyl, hydroxyl, alkoxy, amino, alkylamino, or dialkylamino.

"Heteroaryl" means a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroalkylene" means a -(alkylene)- radical where one, two or three carbons in the alkylene chain is replaced by —O—, N(H, alkyl, or substituted alkyl), S, SO, $SO_2$, or CO.

"Heteroaralkyl" means an -alkylene-R radical where R is heteroaryl as defined above.

The present disclosure also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of this disclosure.

The present disclosure also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

The present disclosure also includes polymorphic forms (amorphous as well as crystalline) and deuterated forms of compounds of Formula (I).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of this disclosure, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this disclosure.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Substituted alkyl" means alkyl group as defined herein which is substituted with one, two or three substituents independently selected from hydroxyl, alkoxy, carboxy, cyano, alkoxycarbonyl, alkylthio, alkylsulfonyl, halo, haloalkoxy, —SO$_2$—NRR', —CONRR' or —NRR' (where each R is hydrogen, alkyl, hydroxyalkyl, or alkoxyalkyl, and each R' is hydrogen, alkyl, or cycloalkyl) or heterocyclyl (preferably heterocycloamino) optionally substituted with one or two groups independently selected from alkyl, hydroxyl, alkoxy, alkylthio, alkylsulfonyl, halo, or —CONRR' (where R and R' are independently hydrogen or alkyl).

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) that, when administered to a mammal for treating a disease, is sufficient to effect such treatment for the disease. The "therapeutically effective amount" will vary depending on the compound, the disease and its severity and the age, weight, etc., of the mammal to be treated.

Representative compounds of the Disclosure are shown in Table I below:

| CPD # | Name | Mass Spec. m/z |
|---|---|---|
| 1 | 3-(3-(7H-pyrrolo[2,3-d]pyrimidin-4-yl)phenyl)-2-cyano-N,N-dimethylacrylamide | ES m/z: 318 (M + 1) |
| 2 | 3-(4-(7H-pyrrolo[2,3-d]pyrimidin-4-yl)phenyl)-2-cyano-N,N-dimethylacrylamide | ES m/z: 318 (M + 1) |
| 3 | 3-(3-((7H-pyrrolo[2,3-d]pyrimidin-4-yl)amino)-phenyl)-2-cyano-N,N-dimethylacrylamide | (ES m/z: 333 (M + 1) |
| 4 | 2-cyano-N,N-dimethyl-3-(3-(methyl(7H-pyrrolo[2,3-d]pyrimidin-4-yl)amino)phenyl)acrylamide | |
| 5 | 2-cyano-3-(3-(isopropyl(7H-pyrrolo[2,3-d]pyrimidin-4-yl)amino)phenyl)-N,N-dimethylacrylamide | |
| 6 | 3-(4-((7H-pyrrolo[2,3-d]pyrimidin-4-yl)amino)-phenyl)-2-cyano-N,N-dimethylacrylamide | (ES m/z: 333 (M + 1) |
| 7 | 2-cyano-N,N-dimethyl-3-(4-(methyl(7H-pyrrolo[2,3-d]pyrimidin-4-yl)amino)phenyl)acrylamide | (ES m/z: 347 (M + 1) |
| 8 | 2-cyano-3-(4-(isopropyl(7H-pyrrolo[2,3-d]pyrimidin-4-yl)amino)phenyl)-N,N-dimethylacrylamide | (ES m/z: 375 (M + 1) |
| 9 | 2-(4-(7H-pyrrolo[2,3-d]pyrimidin-4-yl)pyridin-2-yl)-3-cyclopropylacrylonitrile | (ES m/z: 288 (M + 1) |
| 10 | 2-(4-(7H-pyrrolo[2,3-d]pyrimidin-4-yl)pyridin-2-yl)-4,4-dimethylpent-2-enenitrile | (ES m/z: 304 (M + 1) |
| 11 | 3-(3-((7H-pyrrolo[2,3-d]pyrimidin-4-yl)oxy)phenyl)-2-cyano-N,N-dimethylacrylamide | (ES m/z: 334 (M + 1) |
| 12 | 3-(4-((7H-pyrrolo[2,3-d]pyrimidin-4-yl)oxy)phenyl)-2-cyano-N,N-dimethylacrylamide | (ES m/z: 334 (M + 1) |
| 13 | 2-(5-(7H-pyrrolo[2,3-d]pyrimidin-4-yl)pyridin-2-yl)-3-cyclopropylacrylonitrile | (ES m/z: 288 (M + 1) |
| 14 | 2-(5-(7H-pyrrolo[2,3-d]pyrimidin-4-yl)pyridin-2-yl)-4,4-dimethylpent-2-enenitrile | (ES m/z: 304 (M + 1) |
| 15 | 3-(3-((7H-pyrrolo[2,3-d]pyrimidin-4-yl)amino)-2-methoxyphenyl)-2-cyano-N,N-dimethylacrylamide | (ES m/z: 363 (M + 1) |
| 16 | 3-(3-((7H-pyrrolo[2,3-d]pyrimidin-4-yl)amino)-2-methylphenyl)-2-cyano-N,N-dimethylacrylamide | (ES m/z: 347 (M + 1) |
| 17 | 3-(5-((7H-pyrrolo[2,3-d]pyrimidin-4-yl)amino)-2-chlorophenyl)-2-cyano-N,N-dimethylacrylamide | (ES m/z: 367 (M + 1) |
| 18 | 3-(5-((7H-pyrrolo[2,3-d]pyrimidin-4-yl)amino)-2-fluorophenyl)-2-cyano-N,N-dimethylacrylamide | (ES m/z: 351 (M + 1) |
| 19 | 3-(5-((7H-pyrrolo[2,3-d]pyrimidin-4-yl)amino)-2-methylphenyl)-2-cyano-N,N-dimethylacrylamide | (ES m/z: 347 (M + 1) |
| 20 | 3-(5-((7H-pyrrolo[2,3-d]pyrimidin-4-yl)amino)-2-methoxyphenyl)-2-cyano-N,N-dimethylacrylamide | |
| 21 | 2-(4-((7H-pyrrolo[2,3-d]pyrimidin-4-yl)amino)-pyridin-2-yl)-3-cyclopropylacrylonitrile | (ES m/z: 303 (M + 1) |
| 22 | 3-cyclopropyl-2-(4-(methyl(7H-pyrrolo[2,3-d]-pyrimidin-4-yl)amino)pyridin-2-yl)acrylonitrile | |
| 23 | 2-(4-((7H-pyrrolo[2,3-d]pyrimidin-4-yl)oxy)pyridin-2-yl)-3-cyclopropylacrylonitrile | |
| 24 | 2-(5-((7H-pyrrolo[2,3-d]pyrimidin-4-yl)amino)-pyridin-2-yl)-3-cyclopropylacrylonitrile | (ES m/z: 303 (M + 1) |
| 25 | 3-cyclopropyl-2-(5-(methyl(7H-pyrrolo[2,3-d]-pyrimidin-4-yl)amino)pyridin-2-yl)acrylonitrile | (ES m/z: 317 (M + 1) |
| 26 | 2-(5-((7H-pyrrolo[2,3-d]pyrimidin-4-yl)oxy)pyridin-2-yl)-3-cyclopropylacrylonitrile | |
| 27 | 3-(3-(5H-pyrrolo[2,3-b]pyrazin-2-yl)phenyl)-2-cyano-N,N-dimethylacrylamide | (ES + APCI m/z: 318(M + 1) |
| 28 | 3-(4-(5H-pyrrolo[2,3-b]pyrazin-2-yl)phenyl)-2-cyano-N,N-dimethylacrylamide | ES &APCI m/z: 318 (M + 1) |
| 29 | 3-(3-((5H-pyrrolo[2,3-b]pyrazin-2-yl)amino)phenyl)-2-cyano-N,N-dimethylacrylamide | |
| 30 | 3-(4-((5H-pyrrolo[2,3-b]pyrazin-2-yl)amino)phenyl)-2-cyano-N,N-dimethylacrylamide | |
| 31 | 3-(3-((5H-pyrrolo[2,3-b]pyrazin-2-yl)oxy)phenyl)-2-cyano-N,N-dimethylacrylamide | ES + APCI m/z: 334 (M + 1) |
| 32 | 3-(4-((5H-pyrrolo[2,3-b]pyrazin-2-yl)oxy)phenyl)-2-cyano-N,N-dimethylacrylamide | (ES m/z: 334 (M + 1) |
| 33 | 2-(4-(5H-pyrrolo[2,3-b]pyrazin-2-yl)pyridin-2-yl)-4,4-dimethylpent-2-enenitrile | ES + APCI m/z: 304 (M + 1) |
| 34 | 2-(4-(5H-pyrrolo[2,3-b]pyrazin-2-yl)pyridin-2-yl)-3-cyclopropylacrylonitrile | ES + APCI m/z: 288 (M + 1) |
| 35 | 2-(5-(5H-pyrrolo[2,3-b]pyrazin-2-yl)pyridin-2-yl)-3-cyclopropylacrylonitrile | ES + APCI m/z: 288 (M + 1) |
| 36 | 2-(5-(5H-pyrrolo[2,3-b]pyrazin-2-yl)pyridin-2-yl)-4,4-dimethylpent-2-enenitrile | ES + APCI m/z: 304 (M + 1) |
| 37 | 2-cyano-3-(3-(7-isobutyryl-5H-pyrrolo[2,3-b]pyrazin-2-yl)phenyl)-N,N-dimethylacrylamide | ES + APCI m/z: 386 (M − 1 |
| 38 | 2-cyano-3-(4-(7-isobutyryl-5H-pyrrolo[2,3-b]pyrazin-2-yl)phenyl)-N,N-dimethylacrylamide | (ES + APCI m/z: 386 (M − 1) |
| 39 | 2-cyano-3-(3-((7-isobutyryl-5H-pyrrolo[2,3-b]pyrazin-2-yl)amino)phenyl)-N,N-dimethylacrylamide | |
| 40 | 2-cyano-3-(4-((7-isobutyryl-5H-pyrrolo[2,3-b]pyrazin-2-yl)amino)phenyl)-N,N-dimethylacrylamide | |
| 41 | 2-cyano-3-(3-((7-isobutyryl-5H-pyrrolo[2,3-b]pyrazin-2-yl)oxy)phenyl)-N,N-dimethylacrylamide | |
| 42 | 2-cyano-3-(4-((7-isobutyryl-5H-pyrrolo[2,3-b]pyrazin-2-yl)oxy)phenyl)-N,N-dimethylacrylamide | |
| 43 | 2-(4-(7-isobutyryl-5H-pyrrolo[2,3-b]pyrazin-2-yl)pyridin-2-yl)-4,4-dimethylpent-2-enenitrile | |
| 44 | 3-cyclopropyl-2-(4-(7-isobutyryl-5H-pyrrolo[2,3-b]pyrazin-2-yl)pyridin-2-yl)acrylonitrile | |
| 45 | 3-cyclopropyl-2-(5-(7-isobutyryl-5H-pyrrolo[2,3-b]pyrazin-2-yl)pyridin-2-yl)acrylonitrile | |
| 46 | 2-(5-(7-isobutyryl-5H-pyrrolo[2,3-b]pyrazin-2-yl)pyridin-2-yl)-4,4-dimethylpent-2-enenitrile | |
| 47 | 2-(3-(2-cyano-3-(dimethylamino)-3-oxoprop-1-en-1-yl)phenyl)-N-isopropyl-5H-pyrrolo[2,3-b]pyrazine-7-carboxamide | ES m/z: 403 (M + 1) |

-continued

| CPD # | Name | Mass Spec. m/z |
|---|---|---|
| 48 | 2-(4-(2-cyano-3-(dimethylamino)-3-oxoprop-1-en-1-yl)phenyl)-N-isopropyl-5H-pyrrolo[2,3-b]pyrazine-7-carboxamide | ES &APCI m/z: 403 (M + 1) |
| 49 | 2-((3-(2-cyano-3-(dimethylamino)-3-oxoprop-1-en-1-yl)phenyl)amino)-N-isopropyl-5H-pyrrolo[2,3-b]pyrazine-7-carboxamide | |
| 50 | 2-((4-(2-cyano-3-(dimethylamino)-3-oxoprop-1-en-1-yl)phenyl)amino)-N-isopropyl-5H-pyrrolo[2,3-b]pyrazine-7-carboxamide | ES &APCI m/z: 418 (M + 1) |
| 51 | 2-(3-(2-cyano-3-(dimethylamino)-3-oxoprop-1-en-1-yl)phenoxy)-N-isopropyl-5H-pyrrolo[2,3-b]pyrazine-7-carboxamide | ES &APCI m/z: 419 (M + 1) |
| 52 | 2-(4-(2-cyano-3-(dimethylamino)-3-oxoprop-1-en-1-yl)phenoxy)-N-isopropyl-5H-pyrrolo[2,3-b]pyrazine-7-carboxamide | ES &APCI m/z: 419 (M + 1) |
| 53 | 2-(2-(1-cyano-3,3-dimethylbut-1-en-1-yl)pyridin-4-yl)-N-isopropyl-5H-pyrrolo[2,3-b]pyrazine-7-carboxamide | ES &APCI m/z: 389 (M + 1) |
| 54 | 2-(2-(1-cyano-2-cyclopropylvinyl)pyridin-4-yl)-N-isopropyl-5H-pyrrolo[2,3-b]pyrazine-7-carboxamide | ES &APCI m/z: 373 (M + 1) |
| 55 | 2-(6-(1-cyano-2-cyclopropylvinyl)pyridin-3-yl)-N-isopropyl-5H-pyrrolo[2,3-b]pyrazine-7-carboxamide | |
| 56 | 2-(6-(1-cyano-3,3-dimethylbut-1-en-1-yl)pyridin-3-yl)-N-isopropyl-5H-pyrrolo[2,3-b]pyrazine-7-carboxamide | |
| 57 | 2-cyano-N,N-dimethyl-3-(4-((7-pivaloyl-5H-pyrrolo[2,3-b]pyrazin-2-yl)amino)phenyl)-acrylamide | ES &APCI m/z: 417 (M + 1) |
| 58 | 2-cyano-N,N-dimethyl-3-(3-((7-pivaloyl-5H-pyrrolo[2,3-b]pyrazin-2-yl)amino)phenyl)-acrylamide | ES + APCI m/z: 415 (M − 1) |
| 59 | (2-cyano-3-cyclopropyl-N-(3-((7-pivaloyl-5H-pyrrolo[2,3-b]pyrazin-2-yl)amino)phenyl)acrylamide | ES m/z: 429 (M + 1) |
| 60 | 2-cyano-3-(4-((7-pivaloyl-5H-pyrrolo[2,3-b]-pyrazin-2-yl)amino)phenyl)acrylamide | ES m/z: 389 (M + 1) |
| 61 | 2-cyano-N-methyl-3-(4-((7-pivaloyl-5H-pyrrolo[2,3-b]pyrazin-2-yl)amino)-phenyl)acrylamide | ES m/z: 403(M + 1) |
| 62 | 2-(azetidine-1-carbonyl)-3-(4-((7-pivaloyl-5H-pyrrolo[2,3-b]pyrazin-2-yl)amino)phenyl)acrylonitrile | ES m/z: 429 (M + 1) |
| 63 | 2-(morpholine-4-carbonyl)-3-(4-((7-pivaloyl-5H-pyrrolo[2,3-b]pyrazin-2-yl)amino)phenyl)acrylonitrile | ES m/z: 459 (M + 1) |
| 64 | 2-(4-methylpiperazine-1-carbonyl)-3-(4-((7-pivaloyl-5H-pyrrolo[2,3-b]pyrazin-2-ylamino)phenyl)acrylonitrile | ES m/z: 472(M + 1) |
| 65 | 5-(4-(7-pivaloyl-5H-pyrrolo[2,3-b]pyrazin-2-ylamino)benzylidene)thiazolidine-2,4-dione | ES m/z: 322 (M + 1) |
| 66 | 2-cyano-3-(2-fluoro-4-((7-pivaloyl-5H-pyrrolo[2,3-b]pyrazin-2-yl)amino)phenyl)-N,N-dimethylacrylamide | ES m/z: 435 (M + 1) |
| 67 | 2-cyano-N,N-dimethyl-3-(6-((7-pivaloyl-5H-pyrrolo[2,3-b]pyrazin-2-yl)amino)pyridin-3-yl)acrylamide | ES m/z: 418 (M + 1) |
| 68 | 3-(2-chloro-4-(7-pivaloyl-5H-pyrrolo-[2,3-b]pyrazin-2-ylamino)phenyl)-2-cyano-N,N-dimethylacrylamide | ES m/z: 451 (M + 1) |
| 69 | 2-cyano-3-(3-fluoro-4-((7-pivaloyl-5H-pyrrolo[2,3-b]pyrazin-2-yl)amino)phenyl)-N,N-dimethylacrylamide | ES m/z: 435(M + 1) |
| 70 | 2-cyano-N,N-dimethyl-3-(5-((7-pivaloyl-5H-pyrrolo[2,3-b]pyrazin-2-yl)amino)pyridin-2-yl)acrylamide | ES m/z: 418 (M + 1) |
| 71 | N-(tert-butyl)-2-((4-(2-cyano-3-(dimethylamino)-3-oxoprop-1-en-1-yl)phenyl)amino)-5H-pyrrolo[2,3-b]pyrazine-7-carboxamide | ES m/z: 432 (M + 1) |
| 72 | 2-((4-(2-cyano-3-(dimethylamino)-3-oxoprop-1-en-1-yl)phenyl)amino)-N-isopropyl-5H-pyrrolo[2,3-b]pyrazine-7-carboxamide | ES m/z: 418 (M + 1) |
| 73 | 2-cyano-N,N-dimethyl-3-(5-((7-pivaloyl-5H-pyrrolo[2,3-b]pyrazin-2-yl)amino)thiophen-2-yl)acrylamide | ES m/z: 423 (M + 1) |
| 74 | 2-cyano-N-isopropyl-3-(4-((7-pivaloyl-5H-pyrrolo[2,3-b]pyrazin-2-yl)amino)phenyl)acrylamide | ES m/z: 431 (M + 1) |
| 75 | 2-cyano-3-(4-((7-pivaloyl-5H-pyrrolo[2,3-b]pyrazin-2-yl)amino)phenyl)-N-propylacrylamide | ES m/z: 431 (M + 1) |
| 76 | 2-(piperidine-1-carbonyl)-3-(4-((7-pivaloyl-5H-pyrrolo[2,3-b]pyrazin-2-yl)amino)phenyl)-acrylonitrile | ES m/z: 457 (M + 1) |
| 77 | 2-cyano-3-(4-((7-pivaloyl-5H-pyrrolo[2,3-b]pyrazin-2-yl)amino)phenyl)-N-ethylacrylamide | ES m/z: 417 (M + 1) |
| 78 | 3-ethyl-5-(4-((7-pivaloyl-5H-pyrrolo[2,3-b]pyrazin-2-yl)amino)benzylidene)thiazolidine-2,4-dione | ES m/z: 450 (M + 1) |
| 79 | ethyl 2-cyano-3-(4-((7-pivaloyl-5H-pyrrolo[2,3-b]-pyrazin-2-yl)amino)phenyl)acrylate | ES m/z: 418 (M + 1) |
| 80 | N-(isopropyl)-2-((4-(2-cyano-3-morpholino-3-oxoprop-1-en-1-yl)phenyl)amino)-5H-pyrrolo[2,3-b]pyrazine-7-carboxamide | ES m/z: 460(M + 1) |
| 81 | 2-(methylsulfonyl)-3-(4-((7-pivaloyl-5H-pyrrolo[2,3-b]pyrazin-2-yl)amino)phenyl)-acrylonitrile | ES m/z: 424 (M + 1) |
| 82 | 3-(4-((7-pivaloyl-5H-pyrrolo[2,3-b]pyrazin-2-yl)amino)phenyl)-2-(thiazol-2-yl)acrylonitrile | ES m/z: 429 (M + 1) |
| 83 | 2-((4-(2-cyano-3-oxo-3-(piperazin-1-yl)prop-1-en-1-yl)phenyl)amino)-N-isopropyl-5H-pyrrolo[2,3-b]pyrazine-7-carboxamide | |
| 84 | 3-methyl-5-(4-((7-pivaloyl-5H-pyrrolo[2,3-b]pyrazin-2-yl)amino)benzylidene)thiazolidine-2,4-dione | ES m/z: 436 (M + 1) |
| 85 | 2-cyano-N-methyl-N-phenyl-3-(4-((7-pivaloyl-5H-pyrrolo[2,3-b]pyrazin-2-yl)amino)phenyl)-acrylamide | ES m/z: 479 (M + 1) |
| 86 | 2-(isoxazol-5-yl)-3-(4-((7-pivaloyl-5H-pyrrolo[2,3-b]pyrazin-2-yl)amino)phenyl)-acrylonitrile | ES m/z: 413 (M + 1) |
| 87 | 2-(piperazine-1-carbonyl)-3-(4-((7-pivaloyl-5H-pyrrolo[2,3-b]pyrazin-2-yl)amino)phenyl)-acrylonitrile | |

-continued

| CPD # | Name | Mass Spec. m/z |
|---|---|---|
| 88 | 3-(2-(dimethylamino)ethyl)-5-(4-((7-pivaloyl-5H-pyrrolo[2,3-b]pyrazin-2-yl)amino)-benzylidene)thiazolidine-2,4-dione | |
| 89 | 3-(2-aminoethyl)-5-(4-((7-pivaloyl-5H-pyrrolo[2,3-b]pyrazin-2-yl)amino)benzylidene)thiazolidine-2,4-dione | ES m/z: 465 (M + 1) |
| 90 | 2-(oxazol-2-yl)-3-(4-((7-pivaloyl-5H-pyrrolo[2,3-b]pyrazin-2-yl)amino)phenyl)acrylonitrile | ES m/z: 413 (M + 1) |
| 91 | 3-(4-((7-pivaloyl-5H-pyrrolo[2,3-b]pyrazin-2-yl)amino)phenyl)-2-(1H-1,2,4-triazol-1-yl)acrylonitrile | ES m/z: 413 (M + 1) |
| 92 | 1-cyano-N,N-dimethyl-2-(4-((7-pivaloyl-5H-pyrrolo[2,3-b]pyrazin-2-yl)amino)phenyl)ethenesulfonamide | |
| 93 | 2-((4-(2-cyano-3-(4-methylpiperazin-1-yl)-3-oxoprop-1-en-1-yl)phenyl)amino)-N-isopropyl-5H-pyrrolo[2,3-b]pyrazine-7-carboxamide | ES m/z: 473 (M + 1) |
| 94 | N-(tert-butyl)-2-((4-(2-cyano-3-(4-methylpiperazin-1-yl)-3-oxoprop-1-en-1-yl)phenyl)amino)-5H-pyrrolo[2,3-b]pyrazine-7-carboxamide | |
| 95 | N-(tert-butyl)-2-((4-(2-cyano-3-morpholino-3-oxoprop-1-en-1-yl)phenyl)amino)-5H-pyrrolo[2,3-b]pyrazine-7-carboxamide | |
| 96 | 2-cyano-N,N-dimethyl-3-(4-(7-pivaloyl-5H-pyrrolo[2,3-b]pyrazin-2-yl)phenyl)acrylamide | ES m/z: 402 (M + 1) |
| 97 | 2-cyano-N,N-dimethyl-3-(3-(7-pivaloyl-5H-pyrrolo[2,3-b]pyrazin-2-yl)phenyl)acrylamide | ES m/z: 402 (M + 1) |
| 98 | 3-cyclopropyl-2-(4-(7-pivaloyl-5H-pyrrolo[2,3-b]pyrazin-2-yl)pyridin-2-yl)acrylonitrile | ES m/z: 372 (M + 1) |
| 99 | 4,4-dimethyl-2-(4-(7-pivaloyl-5H-pyrrolo[2,3-b]pyrazin-2-yl)pyridin-2-yl)pent-2-enenitrile | ES m/z: 388 (M + 1) |
| 100 | 2-cyano-N,N-dimethyl-3-(3-((7-pivaloyl-5H-pyrrolo[2,3-b]pyrazin-2-yl)oxy)phenyl)acrylamide | ES &APCI m/z: 418 (M + 1) |
| 101 | 2-cyano-N,N-dimethyl-3-(4-((7-pivaloyl-5H-pyrrolo[2,3-b]pyrazin-2-yl)oxy)phenyl)acrylamide | ES &APCI m/z: 418 (M + 1) |
| 102 | 2-cyano-3-cyclopropyl-N-(3-(7-pivaloyl-5H-pyrrolo[2,3-b]pyrazin-2-yl)phenyl)acrylamide | ES m/z: 414 (M + 1) | or an E or Z isomers or a pharmaceutically acceptable salt thereof.

Embodiment I

In one group of compounds the compounds of Formula (I) have the structure (Ia):

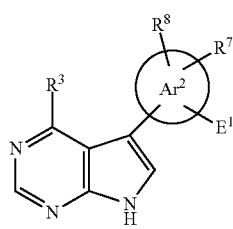

(Ia)

Embodiment A

Within embodiment (I), in one group of compounds $R^3$ is hydrogen.

Embodiment (a)

(a) Within embodiment (I) and (A) above, in one group of compounds, $E^1$ is —P-Q-CH=C($R^b$)(EWG) where EWG is —S(O$_2$)R', —S(O)R', —C(O)NH$_2$, —C(O)NHR$^g$, —C(O)NR$^f$R$^g$, —S(O$_2$)NH$_2$, —SO$_2$NHR$^{i\prime\prime}$, —SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)(OR')OR'', halo, heteroaryl, or aryl; wherein X' is independently halogen (e.g. chloro of fluoro), R', R'', R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached from heterocycloamino; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Embodiment (b)

(b) Within embodiments (I) and (A) above, in one group of compounds, $E^1$ is —P-Q-CH=C($R^b$)(EWG) where EWG is —CO—NR$^f$R$^g$ or —SO$_2$NR$^h$R$^i$ (wherein R$^c$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and R$^h$ and R$^i$ together with the nitrogen atom to which they are attached from heterocycloamino), aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, EWG is —CON(CH$_3$)$_2$.

Within groups in embodiment (b) above, in one group of compounds EWG is pyridine-2-yl, pyridine-3-yl, pyridine-4-yl, pyrrol-1-yl, pyrazol-1-yl, or thiazol-2-yl.

Within the groups in embodiment (b) above, in another group of compounds EWG is dimethylaminocarbonyl, methylaminocarbonyl, isopropylaminocarbonyl, tert-butylaminocarbonyl, or 3-hydroxy-1-methylpropylaminocarbonyl.

Within the groups in embodiment (b) above, in yet another group of compounds EWG is azetidin-1-ylcarbonyl, 4-hydroxyazetidin-1-ylcarbonyl, pyrrolidin-1-ylcarbonyl, 4-ethylpiperazin-1-ylcarbonyl, or 2,6-dimethylmorpholin-4-ylcarbonyl.

Embodiment (c)

(c). Within embodiments (I) and (A) above, in another group of compounds $E^1$ is —P-Q-CH=C($R^b$)(EWG) where EWG is —CO—NR$^f$R$^g$, preferably R$^f$ and R$^g$ are independently alkyl or substituted alkyl or together form

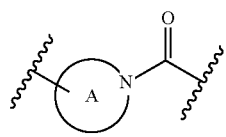

where A is heterocycloamino (such as piperazinyl or piperidinyl) optionally substituted with hydroxyl, methyl, methoxy, amino, methylamino or dimethylamino, preferably substituted at the 3 or 4 position of the piperidinyl and piperazinyl rings.

Embodiment (i)

(i) Within embodiments (I) and (A), (a), (b) and (c) above, and groups contained therein, in one group of compounds, P and Q together are bond.

Embodiment (ii)

(ii) Within embodiments (I) and (A), (a), (b), and (c) above, and groups contained therein, in another group of compounds, P is bond or methylene and Q is phenyl or heteroaryl, preferably -Q- are selected from:

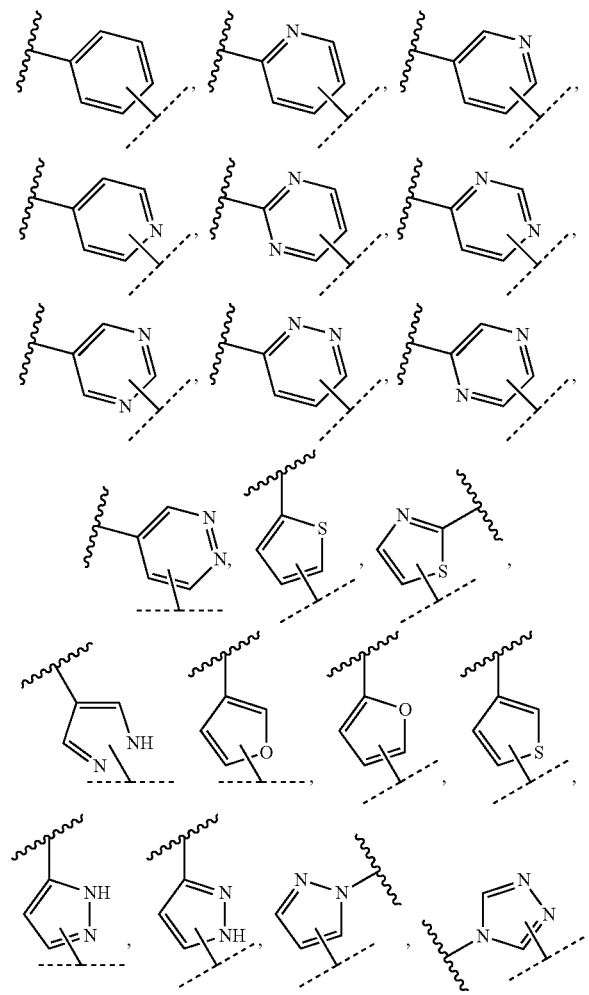

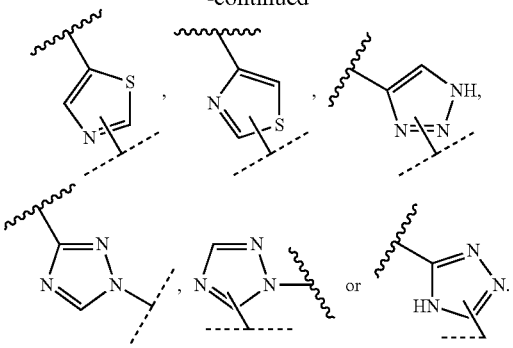

each substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl wherein

symbol denotes point of attachment of the ring to —P— when P is other than bond and directly to the rest of the molecule when P is a bond and

is bond attaching the ring to —CH=C($R^b$)(EWG).

Preferably, when Q is six membered ring, P is a bond and when Q is a five membered ring P is methylene.

Within embodiments (I) and (A), (a), (b), (c), (i) and (ii) above and groups contained therein in one group of compounds, $R^b$ is cyano.

Within embodiments (I), (a), (b), (c), (i) and (ii) above and groups contained therein in one group of compounds, $R^b$ is trifluoromethyl.

Embodiment (d)

(d) Within embodiments (I) and (A) above, in another group of compounds E' is —Z-(EWG')-C($R^b$)=CHR$^c$ where EWG' is —CH(haloalkyl), —NR'—, —S(O$_2$), —S(O), —CO—, —NR'CO—, —NR'SO$_2$

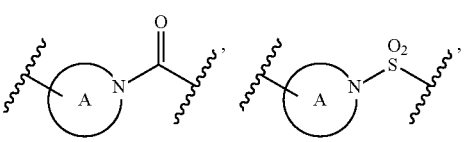

heteroaryl, or aryl; wherein each R' is independently hydrogen, alkyl, substituted alkyl, cycloalkyl; ring A is heterocycloamino where the carbonyl and sulfonyl groups are attached to —C($R^b$)=CHR$^c$; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Embodiment (ia)

(ia) Within embodiments (I), (A), and (d) above, in one group of compounds EWG' is —NR'CO— or —NR'SO$_2$—, preferably —NHCO— and Z is a bond, methylene or ethylene, preferably a bond.

Embodiment (iia)

(iia) Within embodiments (I), (A), and (d) above, in another group of compounds EWG' is

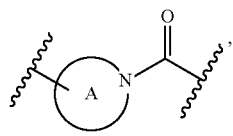

preferably pyrrolidin-1-ylcarbonyl or piperidin-1-ylcarbonyl. Preferably, in one group of compounds EWG' is

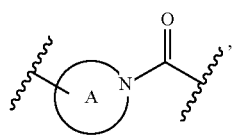

preferably

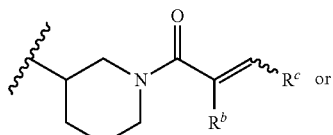

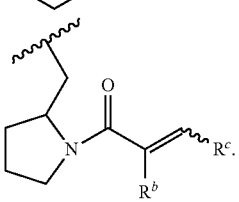

Embodiment (e)

(e) Within embodiments (I) and (A) above, in yet another group of compounds is $E^1$ is —C($R^b$)=CH$R^c$. Preferably, when $Ar^2$ is electron withdrawing in nature.

Embodiment (iiia)

(iiia) Within embodiments (d), (e), (ia) and (iia) above and groups contained therein, in one group of compounds $R^b$ is trifluoromethyl.

Embodiment (iva)

(iva) Within embodiments (d), (e), (ia) and (iia) above and groups contained therein, in one group of compounds, $R^b$ is cyano.

Embodiment (va)

(va) Within embodiments (e), (d) (ia), (iia), (iiia) and (iva) above, in one group of compounds, $R^c$ is tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl,1-methylaminocycloprop-1-ylene, or 1-dimethylaminocycloprop-1-ylene.

Embodiment (f)

(f) Within embodiments (I) and (A) above, in yet another group of compounds, $E^1$ is a group of formula (c);

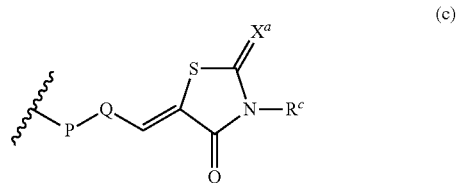

where P and Q are as defined in embodiments (c)(i) and (c)(ii) above, $X^a$ is O or N(H or alkyl) and $R^c$ is hydrogen, alkyl, substituted alkyl, haloalkoxy, cycloalkyl, or cycloalkyleneN-$R^d R^e$ where $R^d$ and $R^e$ are independently hydrogen, alkyl, or cycloalkyl. Preferably, in another group of compounds, P and Q are bond or alkylene, preferably methylene.

Within the groups in (f) above, in one group of compound $R^c$ is hydrogen, methyl, or cyclopropyl.

Embodiment (g)

(g) In yet another group of compounds, $E^1$ is a group of formula (d);

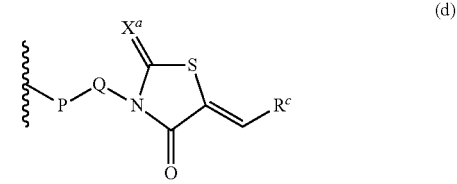

where P and Q are as defined in embodiments (c)(i) and (c)(ii) above, $X^a$ is O or N(H or alkyl) and $R^c$ is hydrogen, alkyl, substituted alkyl, haloalkoxy, cycloalkyl, or cycloalkyleneNR$^d R^e$ where $R^d$ and $R^e$ are independently hydrogen, alkyl, or cycloalkyl. Preferably, in one group of compounds P and Q are bond or alkylene, preferably methylene. Within groups in (f) in one group of compounds $R^c$ is tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl,1-methylaminocycloprop-1-ylene, or 1-dimethylaminocycloprop-1-ylene.

Embodiment II

In another group of compounds the compounds of Formula (I) have the structure (Ib):

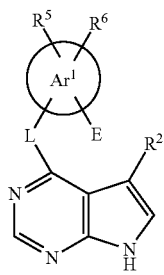

Embodiment (ib)

(ib) Within embodiment (II) above, in one group of compounds $R^2$ is hydrogen.

Embodiment III

In yet another group of compounds the compounds of Formula (I) have the structure (Ic):

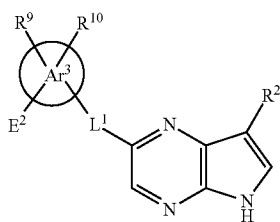

Embodiment (ic)

(ic) Within embodiment (III) above, in one group of compounds $R^2$ is hydrogen, alkyl, cycloalkyl, halo, cyano, —COR (where R is alkyl, heterocyclyl, heterocyclylalkyl or substituted alkyl), or —CONRR' (where R is hydrogen or alkyl and R' is hydrogen, alkyl, heterocyclyl, heterocyclylalkyl, or substituted alkyl).

Embodiment (iic)

(iic) Within embodiment (III) above, in one group of compounds $R^2$ is hydrogen, methyl, isopropyl, tert-butyl, cyclopropyl, fluoro or cyano. Preferably, $R^2$ is hydrogen, methyl, tert-butyl, cyclopropyl, fluoro or cyano.

Embodiment (iiic)

(iiic) Within embodiment (III) above, in one group of compounds $R^2$ is acyl, preferably —COR where R is alkyl, preferably —COR where R is isopropyl, isobutyl, or tert-butyl, more preferably tert-butyl.

Embodiment (ivc)

(ivc) Within embodiment (III) above, in one group of compounds $R^2$ is —COR where R is cycloalkyl or heterocyclyl, preferably R is cyclopropyl, cyclohexyl, cyclopentyl, pyrrolidinyl, tetrahydropyranyl, piperidinyl, tetrahydrothiopyranyl, or 1,1,-dioxo-tetrahydrothiopyranyl, more preferably, cyclopropyl, 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each of which is optionally substituted at the carbon attached to —CO— with alkyl, preferably methyl and the ring with a ring nitrogen atoms is optionally substituted at ring nitrogen with alkylcarbonyl, preferably acetyl. Preferably R is 1-methylcyclohex-1-yl.

Embodiment (vc)

(vc) Within embodiment (III) above, in one group of compounds $R^2$ is —COR where R is heterocyclylalkyl, preferably heterocyclyl ring is pyrrolidinyl, tetrahydropyranyl, piperidinyl, tetrahydrothiopyranyl, or 1,1,-dioxo-tetrahydrothiopyranyl; preferably $R^2$ is —COCH$_2$heterocyclyl where the heterocyclyl ring is 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each ring containing nitrogen ring atom is optionally substituted at ring nitrogen with alkylcarbonyl, preferably acetyl and each ring is optionally substituted at the carbon attached to —CH$_2$— with alkyl, preferably methyl.

Embodiment (vic)

(vic) Within embodiment (III) above, in one group of compounds $R^2$ is —COR where R is substituted alkyl, preferably alkyl substituted with one or two hydroxyl, alkoxy, or amino, preferably 1,3-dimethoxyprop-2-yl, —C(CH$_3$)$_2$CH$_2$NH$_2$, —CH(CH$_3$)CH$_2$OCH$_3$, 1,3-dihydroxyprop-2-yl, —CH(CH$_3$)CH$_2$OH, 1,3-dihydroxy-2-methylprop-2-yl, —C(CH$_3$)(OC$_2$H$_5$)$_2$, —CH$_2$C(CH$_3$)$_2$CH$_2$OH, 2-hydroxypropyl, 3-methoxyprop-2-yl, 2-methoxyprop-1-yl, 2,3-dihydroxyprop-1-yl, 2-methoxyethyl, 3-methoxypropyl, —CH$_2$C(CH$_3$)$_2$OCH$_3$, 3-methoxybutyl, —C(CH$_3$)$_2$OCH$_3$, or methoxymethyl.

Embodiment (viic)

(viic) Within embodiment (III) above, in one group of compounds $R^2$ is aminocarbonyl, preferably —CONHR' where R' is alkyl, preferably R' is isopropyl, isobutyl, or tert-butyl, more preferably tert-butyl. More preferably, R' is isopropyl.

Embodiment (viiic)

(viiic) Within embodiment (III) above, in one group of compounds $R^2$ is —CONHR' where R' is cycloalkyl or heterocyclyl, preferably R' is cyclopropyl, cyclohexyl, cyclopentyl, pyrrolidinyl, tetrahydropyranyl, piperidinyl, tetrahydrothiopyranyl, or 1,1,-dioxo-tetrahydrothiopyranyl, more preferably, cyclopropyl, 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each of which is optionally substituted at the carbon attached to —NH— with alkyl, preferably methyl and ring containing nitrogen ring atom is optionally substituted at ring nitrogen with alkylcarbonyl, preferably acetyl. Preferably R' is 1-methylcyclohex-1-yl.

Embodiment (ixc)

(ixc) Within embodiment (III) above, in one group of compounds $R^2$ is —CONHR' where R' is heterocyclylalkyl, preferably heterocyclyl ring is pyrrolidinyl, tetrahydropyranyl, piperidinyl, tetrahydrothiopyranyl, or 1,1,-dioxo-tetrahydrothiopyranyl; preferably $R^2$ is —COCH$_2$heterocyclyl where heterocyclyl is 3-, or 4-pyrrolidinyl, 3- or 4-tetrahydropyranyl, 3- or 4-piperidinyl, 3- or 4-tetrahydrothiopyranyl, or 3- or 4-1,1,-dioxo-tetrahydrothiopyranyl, each ring containing nitrogen ring atom is optionally substituted at ring nitrogen with alkylcarbonyl, preferably acetyl and each ring is optionally substituted at the carbon attached to —CH$_2$— with alkyl, preferably methyl.

Embodiment (xc)

(xc) Within embodiment (III) above, in one group of compounds $R^2$ is —CONHR' where R' is substituted alkyl, preferably alkyl substituted with one or two hydroxyl, alkoxy, amino, preferably R' is 1,3-dimethoxyprop-2-yl, —C(CH$_3$)$_2$CH$_2$NH$_2$, —CH(CH$_3$)CH$_2$OCH$_3$, 1,3-dihydroxyprop-2-yl, —CH(CH$_3$)CH$_2$OH, 1,3-dihydroxy-2-methylprop-2-yl, —C(CH$_3$)(OC$_2$H$_5$)$_2$, —CH$_2$C(CH$_3$)$_2$CH$_2$OH, 2-hydroxypropyl, 3-methoxyprop-2-yl, 2-methoxyprop-1-yl, 2,3-dihydroxyprop-1-yl, 2-methoxyethyl, 3-methoxypropyl, —CH$_2$C(CH$_3$)$_2$OCH$_3$, 3-methoxybutyl, —C(CH$_3$)$_2$OCH$_3$, or methoxymethyl.

Embodiment B

Within the compound of Formula (I) as defined above, embodiments (II), (III), and (ic)-(xc), and groups contained therein, in one group of compounds L and $L^1$ are bond, —O—, —NH—, —Nalkyl-, -(alkylene)NH— or —NH(alkylene). Within groups in embodiment (B), in one group of compounds L and $L^1$ are bond. Within groups in embodiment (B), in another group of compounds L and $L^1$ are —O—. Within groups in embodiment (B), in yet another group of compounds L and $L^1$ are —NH—, —Nmethyl-, —N(isopropyl)-, -(methylene)NH— or —NH(methylene), preferably NH or —NHmethylene-, preferably —NH—.

Embodiment (a1)

(a1) Within embodiments (II), (III), (ic)-(xc) in embodiments (III) above, and (B) above, and groups contained therein, in one group of compounds, E and $E^2$ are —P—CH═C($R^b$)(EWG) where EWG is —S(O$_2$)R', —S(O)R', —C(O)NH$_2$, —C(O)NHR$^g$, —C(O)NR$^f$R$^g$, —S(O$_2$)NH$_2$, —SO$_2$NHR$^i$, —SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)(OR')OR", halo, heteroaryl, or aryl; wherein X' is independently halogen (e.g. chloro of fluoro), R', R", R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached from heterocycloamino; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Embodiment (b1)

(b1) Within embodiments (II), (III), (ic)-(xc) in embodiments (III) above, and (B) above, and groups contained therein, in one group of compounds, E and $E^2$ are —P—CH═C($R^b$)(EWG) where EWG is —CO—NR$^f$R$^g$ or —SO$_2$NR$^h$R$^i$, preferably —CONR$^f$R$^g$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and R$^h$ and R$^i$ together with the nitrogen atom to which they are attached from heterocycloamino), aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, EWG is —CON(CH$_3$)$_2$. Within groups in embodiment (b1), in one group of compounds EWG is pyridine-2-yl, pyridine-3-yl, pyridine-4-yl, pyrrol-1-yl, pyrazol-1-yl, or thiazol-2-yl. Within the groups in embodiment (b), in another group of compounds EWG is dimethylaminocarbonyl, methylaminocarbonyl, isopropylaminocarbonyl, tert-butylaminocarbonyl, or 3-hydroxy-1-methylpropylaminocarbonyl. Within the groups in embodiment (b1), in yet another group of compounds EWG is azetidin-1-ylcarbonyl, 4-hydroxyazetidin-1-ylcarbonyl, pyrrolidin-1-ylcarbonyl, 4-ethylpiperazin-1-ylcarbonyl, or 2,6-dimethylmorpholin-4-ylcarbonyl.

Embodiment (c1)

(c1). Within embodiments (II), (III), (ic)-(xc) in embodiments (III) above, and (B) above, and groups contained therein, in one group of compounds, E and $E^2$ are —P—CH═C($R^b$)(EWG) where EWG is —CO—NR$^f$R$^g$, preferably R$^f$ and R$^g$ are independently alkyl or substituted alkyl or together form

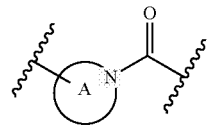

where A is heterocycloamino (such as piperazinyl or piperidinyl) optionally substituted with hydroxyl, methyl, methoxy, amino, methylamino or dimethylamino, preferably substituted at the 3 or 4 position of the piperidinyl and piperazinyl rings.

Embodiment (id)

(id) Within embodiments (a1), (b1) and (c1) above, and groups contained therein, in one group of compounds, P is bond.

Embodiment (iid)

(iid) Within embodiments (a1), (b1) and (c1) above, and groups contained therein, in one group of compounds, P is alkylene or heteroalkylene, preferably methylene.

Within embodiments (II), (III), (ic)-(xc) in embodiments (III) above, (B), (a1)-(c1), (id) and (iid) and groups contained therein in one group of compounds, $R^b$ is cyano.

Within groups (II), (III), (ic)-(xc) in embodiments (III) above, (B), (a1)-(c1), (id) and (iid) and groups contained therein in one group of compounds, $R^b$ is trifluoromethyl.

Embodiment (d1)

(d1) Within embodiments (II), (III), (ic)-(xc) in embodiments (III) above, and (B) above, in another group of compounds E and $E^2$ are —Z'-(EWG')-C($R^b$)=CH$R^c$ where EWG' is —CH(haloalkyl), —NR'—, —S(O$_2$), —S(O), —CO—, —NR'CO—, —NR'SO$_2$

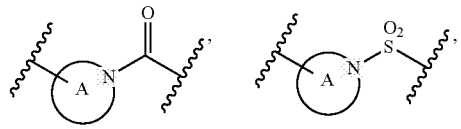

heteroaryl, or aryl; wherein each R' is independently hydrogen, alkyl, substituted alkyl, cycloalkyl; ring A is heterocycloamino where the carbonyl and sulfonyl groups are attached to —C($R^b$)=CH$R^c$; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Embodiment (e1)

(e1) Within embodiments (II), (III), (ic)-(xc) in embodiments (III) above, and (B) above, in another group of compounds E and $E^2$ are —Z'-(EWG')-C($R^b$)=CH$R^c$ where EWG' is —NR'CO— or —NR'SO$_2$—, preferably —NHCO— and Z is a bond, methylene or ethylene, preferably a bond.

Embodiment (f1)

(f1) Within embodiments (II), (III), (ic)-(xc) in embodiments (III) above, and (B), in another group of compounds E and $E^2$ are —Z'-(EWG')-C($R^b$)=CH$R^c$ where EWG' is

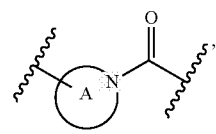

preferably pyrrolidin-1-ylcarbonyl or piperidin-1-ylcarbonyl. Preferably, in one group of compounds EWG' is

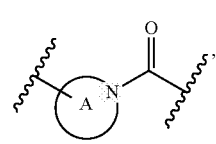

preferably

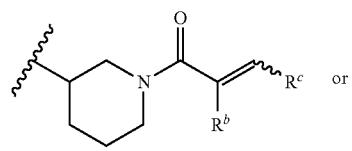

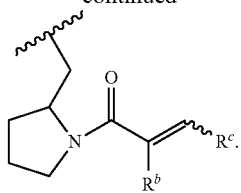

Embodiment (g1)

(g1) Within embodiments (II), (III), (ic)-(xc) in embodiments (III) above, and (B) above, in another group of compounds E and $E^2$ are —Z'—(CO')—C($R^b$)=CH$R^c$. Preferably Z' is bond.

Embodiment (h1)

(h1) Within embodiments (II), (III), (ic)-(xc) in embodiments (III) above, and (B) above, in another group of compounds E and $E^2$ are —C($R^b$)=CH$R^c$. Preferably, when $Ar^1$ and $Ar^3$ are electron withdrawing in nature e.g., pyridinyl or pyrimidinyl.

Embodiment (ie)

(ie) Within embodiments (d1), (e1), f1), (g1) and (h1) and groups contained therein, in one group of compounds $R^b$ is trifluoromethyl.

Embodiment (iie)

(iie) Within embodiments (d1), (e1), f1), (g1) and (h1) and groups contained therein, in one group of compounds, $R^b$ is cyano.

Embodiment (iiie)

(iiie) Within embodiments (d1), (e1), f1), (g1) and (h1) in one group of compounds, $R^c$ is tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl,1-methylaminocycloprop-1-ylene, or 1-dimethylaminocycloprop-1-ylene.

Embodiment (i1)

(i1) Within embodiments (II), (III), (ic)-(xc) in embodiments (III) above, and (B) above, in yet another group of compounds, E and $E^2$ is a group of formula (a);

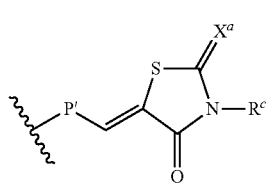

(a)

where P' is as defined above, $X^a$ is O or N(H or alkyl) and $R^c$ is hydrogen, alkyl, substituted alkyl, haloalkoxy, cycloalkyl, or cycloalkyleneNR$^d$R$^e$ where R$^d$ and R$^e$ are independently hydrogen, alkyl, or cycloalkyl. Preferably, in another group of compounds, P' is alkylene, preferably methylene.

Within the groups in (i1) above, in one group of compound $R^c$ is hydrogen, methyl, or cyclopropyl.

Embodiment (j1)

(j1) Within embodiments (II), (III), (ic)-(xc) in embodiments (III) above, and (B) above, in yet another group of compounds, E and $E^2$ is a group of formula (b);

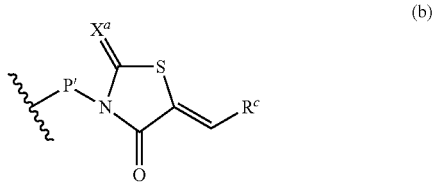

where P' is as defined above, $X^a$ is O or N(H or alkyl) and $R^c$ is hydrogen, alkyl, substituted alkyl, haloalkoxy, cycloalkyl, or cycloalkyleneNR$^d$R$^e$ where R$^d$ and R$^e$ are independently hydrogen, alkyl, or cycloalkyl. Preferably, in one group of compounds P is bond or alkylene, preferably methylene. Within groups in (j1) in one group of compounds $R^c$ is tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl,1-methylaminocycloprop-1-ylene, or 1-dimethylaminocycloprop-1-ylene.

Embodiment (IV)

(IV). Within all the embodiments described above e.g., (I), (A), (a), (b), (c), (i), (ii), (d), (ia), (iia), (e), (iiia)-(va), (f), (g), (II), (III), (ic)-(xc), (B), (a1)-(c1), (id), (iid), (d1), (e1)-(h1), (ie)-(iiie), (i1), and (j1), and groups contained therein, in one group of compounds, $Ar^1$, $Ar^2$ and $Ar^3$ are phenyl. Within the groups in (IV), in one group of compounds, E, $E^1$ and $E^2$ are attached to the 3 or 4, preferably 3-position of the phenyl ring, the carbon attached to L, $L^1$ or azaindole ring being C-1. Within the groups in this embodiment, in one group of compounds, $R^5$, $R^6$, $R^7$, $R^8$, $R^9$ and $R^{10}$ are independently hydrogen, methyl, methoxy, trifluoromethyl, fluoro, chloro, cyano, or cyclopropyl, preferably hydrogen, methyl, methoxy, trifluromethyl, cyano, fluoro or chloro, more preferably hydrogen, chloro, fluoro, methyl or methoxy. More preferably, $R^5$, $R^7$, and $R^9$ are hydrogen and $R^6$, $R^8$, and $R^{10}$ are at carbon ortho or para, preferably ortho, to carbon substituted with E, $E^1$ or $E^2$ respectively.

Embodiment (V)

(V). Within all the embodiments described above e.g., (I), (A), (a), (b), (c), (i), (ii), (d), (ia), (iia), (e), (iiia)-(va), (f), (g), (II), (III), (ic)-(xc), (B), (a1)-(c1), (id), (iid), (d1), (e1)-(h1), (ie)-(iiie), (i1), and (j1), and groups contained therein, in one group of compounds, $Ar^1$, $Ar^2$ and $Ar^3$ are heteroaryl, preferably pyridinyl, pyrimidinyl, or indolyl, preferably, pyrimidin-2-yl, pyridine-3-yl, pyridine-4-yl or indol-6-yl, even more preferably pyridine-3-yl or pyridine-4-yl. Within the groups in (V), in one group of compounds, E, $E^1$ and $E^2$ are attached to the 4-position of pyrimidin-2-yl, 2-position of pyridine-4-yl, 6-position of pyridine-3-yl, or 4-position of indol-6-yl, the nitrogen atom of enumerated rings being position 1. Within the groups in this embodiment, in one group of compounds, $R^5$, $R^6$, $R^7$, $R^8$, $R^9$ and $R^{10}$ are independently hydrogen, methyl, methoxy, trifluoromethyl, fluoro, chloro, cyano, or cyclopropyl, preferably hydrogen, methyl, triflurormethyl, cyano, fluoro or chloro, even more preferably hydrogen, fluoro, chloro, or methyl. More preferably, $R^5$, $R^7$, and $R^9$ are hydrogen and $R^6$, $R^8$, and $R^{10}$ are at carbon ortho or para to carbon substituted with E, $E^1$ or $E^2$ respectively.

Embodiment (VI)

(VI). Within all the embodiments described above e.g., (I), (A), (a), (b), (c), (i), (ii), (d), (ia), (iia), (e), (iiia)-(va), (f), (g), (II), (III), (ic)-(xc), (B), (a1)-(c1), (id), (iid), (d1), (e1)-(h1), (ie)-(iiie), (i1), and (j1), and groups contained therein, in one group of compounds, $Ar^1$, $Ar^2$ and $Ar^3$ are heterocyclyl, preferably piperidinyl, pyrrolidinyl, or 2,3-dihydroindolyl, preferably, pyrrolidin-3-yl, piperidin-3-yl, or 2,3-dihydroindol-6-yl. Within the groups in (VI), in one group of compounds, E, $E^1$ and $E^2$ are attached to the ring nitrogen atom nitrogen of pyrrolidin-3-yl, piperidin-3-yl or 2,3-dihydroindol-6-yl. Within the groups in this embodiment, in one group of compounds, $R^5$, $R^6$, $R^7$, $R^8$, $R^9$ and $R^{10}$ are independently hydrogen, methyl, trifluoromethyl, fluoro, chloro, cyano, or cyclopropyl, preferably hydrogen, methyl, trifluoromethyl, cyano, fluoro or chloro. More preferably, $R^5$, $R^7$, and $R^9$ are hydrogen and $R^6$, $R^8$, and $R^{10}$ are at carbon ortho or para to carbon substituted with E, $E^1$ or $E^2$ respectively. Within this group of compounds in one group of compounds E, $E^1$ or $E^2$ are —COC($R^b$)=CHR$^c$ where R$^b$ and R$^e$ are as defined above.

Embodiment (VII)

(VII). In further embodiments 1-34 below, the present disclosure include:

1. A compound of Formula (I) or a pharmaceutically acceptable salt thereof:

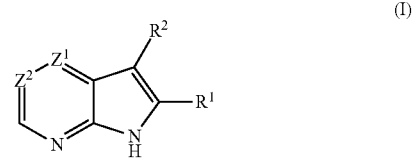

wherein:
$Z^1$ is N or $CR^3$;
$Z^2$ is N or $CR^4$ provided that at least one of $Z^1$ and $Z^2$ is N and both $Z^1$ and $Z^2$ are not simultaneously N;
$R^1$ is hydrogen, alkyl, halo, haloalkyl, haloalkoxy, cyano or cycloalkyl; and
(i) when $Z^1$ is $CR^3$ where $R^3$ is hydrogen, alkyl, halo, haloalkyl, haloalkoxy, cyano, cycloalkyl, or a ring of formula (A):

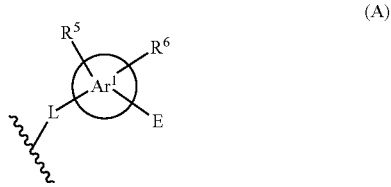

then, $R^2$ is hydrogen, alkyl, halo, haloalkyl, haloalkoxy, cyano, cycloalkyl, or a ring of formula (B):

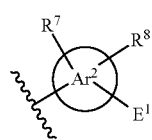

(B)

provided at least one ring of formula (A) and (B) is present and not both rings of formula (A) and (B) are present simultaneously; and (ii) when $Z^2$ is $CR^4$ where $R^4$ is a ring of formula (C):

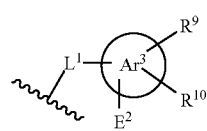

(C)

then, $R^2$ is hydrogen, alkyl, cycloalkyl, halo, cyano, acyl, or aminocarbonyl; and wherein:

L and $L^1$ are independently bond, —NR—, —O—, CO, —S(O)n- (where n is 0-2), —NRCO—, —CONR—, or heteroalkylene (where R is hydrogen, alkyl or cycloalkyl);

$Ar^1$, $Ar^2$ and $Ar^3$ are independently aryl, heteroaryl, cycloalkyl or heterocyclyl;

$R^5$, $R^6$, $R^7$, $R^8$, $R^9$ and $R^{10}$ are independently hydrogen, alkyl, alkoxy, halo, haloalkyl, haloalkoxy, cyano or cycloalkyl;

E and $E^2$ are independently:

(i) —P—CH=C($R^b$)(EWG) where P is a bond, $NR^a$ (where $R^a$ is hydrogen or alkyl), —O—, S, SO, $SO_2$, alkylene or heteroalkylene, $R^b$ is cyano, nitro, halo, haloalkyl, haloalkoxy, alkylthio, or alkylsulfonyl and EWG is an electron withdrawing group; or (ii) —Z'-(EWG')-C($R^b$)=$CHR^c$ where Z is bond, $NR^a$ (where $R^a$ is hydrogen or alkyl), —O—, S, SO, $SO_2$, alkylene, or heteroalkylene, EWG' is a bond or an electron withdrawing group, $R^b$ is cyano, nitro, halo, haloalkyl, haloalkoxy, alkylthio, or alkylsulfonyl and $R^c$ is alkyl, substituted alkyl, haloalkoxy, cycloalkyl, cycloalkyleneNR$^d$R$^e$ where $R^d$ and $R^e$ are independently hydrogen, alkyl, or cycloalkyl; or (iii) a group of formula (a) or (b);

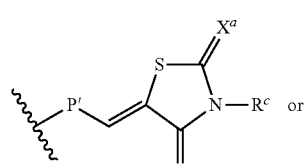

(a)

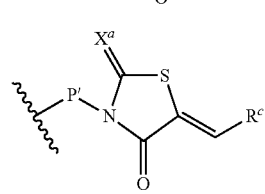

(b)

where P' is bond, alkylene or heteroalkylene, $X^a$ is O or N(H or alkyl) and $R^c$ is hydrogen, alkyl, substituted alkyl, haloalkoxy, cycloalkyl, or cycloalkyleneNR$^d$R$^e$ where $R^d$ and $R^e$ are independently hydrogen, alkyl, or cycloalkyl; and $E^1$ is:

(i) —P-Q-CH=C($R^b$)(EWG) where P is a bond, $NR^a$ (where $R^a$ is hydrogen or alkyl), —O—, S, SO, $SO_2$, alkylene or heteroalkylene, Q is a bond, aryl or heteroaryl wherein the aryl or heteroaryl ring is substituted with one or two substituents independently selected from hydrogen, alkyl, halo, haloalkyl, or haloalkoxy, $R^b$ is cyano, nitro, halo, haloalkyl, haloalkoxy, alkylthio, or alkylsulfonyl and EWG is an electron withdrawing group; or (ii) —Z-(EWG')-C($R^b$)=$CHR^c$ where Z is bond, $NR^a$ (where $R^a$ is hydrogen or alkyl), —O—, S, SO, $SO_2$, alkylene, cycloalkylene, heteroalkylene, —($Z^a$)$_{n1}$-aryl, or —($Z^a$)$_{n1}$-heteroaryl (wherein n1 is 0 or 1, $Z^a$ is $NR^a$ (where $R^a$ is hydrogen or alkyl), —O—, S, SO, $SO_2$, alkylene, or heteroalkylene and aryl or heteroaryl is optionally substituted with one or two substituents independently selected from hydrogen, halo, alkyl, alkoxy, alkylthio, haloalkyl, or haloalkoxy), EWG' is a bond or an electron withdrawing group, $R^b$ is cyano, nitro, halo, haloalkyl, haloalkoxy, alkylthio, or alkylsulfonyl and $R^c$ is alkyl, substituted alkyl, haloalkoxy, cycloalkyl, cycloalkyleneNR$^d$R$^e$ where $R^d$ and $R^e$ are independently hydrogen, alkyl, or cycloalkyl; or (iii) a group of formula (c) or (d);

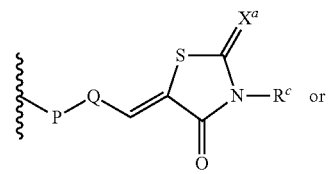

(c)

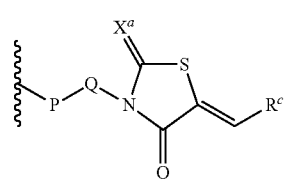

(d)

where P and Q are as defined above, $X^a$ is O or N(H or alkyl) and $R^c$ is hydrogen, alkyl, substituted alkyl, haloalkoxy, cycloalkyl, or cycloalkyleneNR$^d$R$^e$ where $R^d$ and $R^e$ are independently hydrogen, alkyl, or cycloalkyl.

2. The compound of previous embodiment 1 wherein the compound of Formula (I) has the structure (Ib):

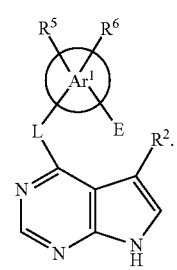

(Ib)

3. The compound of the previous embodiment 1 wherein the compound of Formula (I) has the structure (Ic):

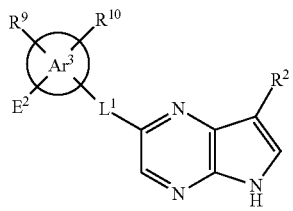

(Ic)

4. The compound of any of the previous embodiments 1 and 2, wherein $R^2$ is hydrogen.
5. The compound of any of the previous embodiments 1 and 3, wherein $R^2$ is hydrogen, alkyl, cycloalkyl, halo, cyano, —COR (where R is alkyl, heterocyclyl, heterocyclylalkyl or substituted alkyl), or —CONRR' (where R is hydrogen or alkyl and R' is hydrogen, alkyl, heterocyclyl, heterocyclylalkyl, or substituted alkyl).
6. The compound of the previous embodiment 3, wherein $R^2$ is acyl, preferably —COR where R is alkyl, preferably —COR where R is isopropyl, isobutyl, or tert-butyl, more preferably tert-butyl.
7. The compound of the previous embodiment 3, wherein $R^2$ is —COR where R is cycloalkyl or heterocyclyl, preferably R is cyclopropyl, cyclohexyl, cyclopentyl, pyrrolidinyl, tetrahydropyranyl, piperidinyl, tetrahydrothiopyranyl, or 1,1,-dioxo-tetrahydrothiopyranyl, more preferably, cyclopropyl, 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each of which is optionally substituted at the carbon attached to —CO— with alkyl, preferably methyl and the ring with a ring nitrogen atoms is optionally substituted at ring nitrogen with alkylcarbonyl, preferably acetyl. Preferably R is 1-methylcyclohex-1-yl.
8. The compound of the previous embodiment 3, wherein $R^2$ is aminocarbonyl, preferably —CONHR' where R' is alkyl, preferably R' is isopropyl, isobutyl, or tert-butyl, more preferably tert-butyl. More preferably, isopropyl.
9. The compound of the previous embodiment 3, wherein $R^2$ is —CONHR' where R' is cycloalkyl or heterocyclyl, preferably R' is cyclopropyl, cyclohexyl, cyclopentyl, pyrrolidinyl, tetrahydropyranyl, piperidinyl, tetrahydrothiopyranyl, or 1,1,-dioxo-tetrahydrothiopyranyl, more preferably, cyclopropyl, 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each of which is optionally substituted at the carbon attached to —NH— with alkyl, preferably methyl and ring containing nitrogen ring atom is optionally substituted at ring nitrogen with alkylcarbonyl, preferably acetyl. Preferably R' is 1-methylcyclohex-1-yl.
10. The compound of the previous embodiment 3, wherein $R^2$ is —CONHR' where R' is substituted alkyl, preferably alkyl substituted with one or two hydroxyl, alkoxy, amino, preferably R' is 1,3-dimethoxyprop-2-yl, —C(CH$_3$)$_2$CH$_2$NH$_2$, —CH(CH$_3$)CH$_2$OCH$_3$, 1,3-dihydroxyprop-2-yl, —CH(CH$_3$)CH$_2$OH, 1,3-dihydroxy-2-methylprop-2-yl, —C(CH$_3$)(OC$_2$H$_5$)$_2$, —CH$_2$C(CH$_3$)$_2$CH$_2$OH, 2-hydroxypropyl, 3-methoxyprop-2-yl, 2-methoxyprop-1-yl, 2,3-dihydroxyprop-1-yl, 2-methoxyethyl, 3-methoxypropyl, —CH$_2$C(CH$_3$)$_2$OCH$_3$, 3-methoxybutyl, —C(CH$_3$)$_2$OCH$_3$, or methoxymethyl.
11. The compound of any of the previous embodiments 1-10, wherein L and $L^1$ are bond, —O—, —NH—, —Nalkyl-, -(alkylene)NH— or —NH(alkylene). Preferably, L and $L^1$ are bond. Preferably, L and $L^1$ are —O—. Preferably, L and $L^1$ are L and $L^1$ are —NH—, —Nmethyl-, —N(isopropyl)-, -(methylene)NH— or —NH(methylene), preferably NH or —NHmethylene-, preferably NH.
12. The compound of any of the previous embodiments 1-11, wherein E and $E^2$ are —P—CH=C($R^b$)(EWG) where EWG is —S(O$_2$)R', —S(O)R', —C(O)NH$_2$, —C(O)NHR$^g$, —C(O)NR$^f$R$^g$, —S(O$_2$)NH$_2$, —SO$_2$NHR$^h$, —SO$_2$NR$^h$R$^i$, —PO(OR')$_2$, —PO$_3$H$_2$, —PO(NR'$_2$)$_2$, —C≡N, —CH(haloalkyl), —C(O)X', —COOH, —COOR', —C(O)R', —C(O)H, —P(O)(OR')OR", halo, heteroaryl, or aryl; wherein X' is independently halogen (e.g. chloro of fluoro), R', R", R$^f$, R$^g$, R$^h$, and R$^i$ are independently hydrogen, alkyl, substituted alkyl, cycloalkyl, cycloalkyleneNR$^d$R$^e$ (where R$^d$ and R$^e$ are independently hydrogen, alkyl, or cycloalkyl) or R$^f$ and R$^g$ and R$^h$ and R$^i$ together with the nitrogen atom to which they are attached from heterocycloamino; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.
13. The compound of any of the previous embodiments 1-11, wherein E and $E^2$ are —P—CH=C($R^b$)(EWG) where EWG is —CO—NR$^f$R$^g$ or —SO$_2$NR$^h$R$^i$, preferably —CONR$^f$R$^g$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and R$^h$ and R$^i$ together with the nitrogen atom to which they are attached from heterocycloamino), aryl or heteroaryl wherein each of the aforementioned ring is substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, EWG is —CON(CH$_3$)$_2$. Preferably, EWG is pyridine-2-yl, pyridine-3-yl, pyridine-4-yl, pyrrol-1-yl, pyrazol-1-yl, or thiazol-2-yl. Preferably, EWG is dimethylaminocarbonyl, methylaminocarbonyl, isopropylaminocarbonyl, tert-butylaminocarbonyl, or 3-hydroxy-1-methylpropylaminocarbonyl. Preferably, EWG is azetidin-1-ylcarbonyl, 4-hydroxyazetidin-1-ylcarbonyl, pyrrolidin-1-ylcarbonyl, 4-ethylpiperazin-1-ylcarbonyl, or 2,6-dimethylmorpholin-4-ylcarbonyl.
14. The compound of the previous embodiment 13, wherein P is a bond.
15. The compound of the previous embodiment 13, wherein P is a alkylene, preferably methylene.
16. The compound of any of the previous embodiments 1-15, wherein $R^b$ is cyano.
17. The compound of any of the previous embodiments 1-11, wherein E and $E^2$ are —Z'-(EWG')-C($R^b$)=CHR$^c$ where EWG' is —CH(haloalkyl), —NR'—, —S(O$_2$), —S(O), —CO—, —NR'CO—, —NR'SO$_2$

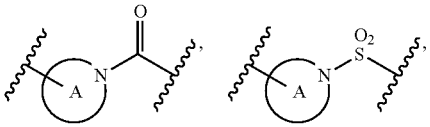

heteroaryl, or aryl; wherein each R' is independently hydrogen, alkyl, substituted alkyl, cycloalkyl; ring A is heterocycloamino where the carbonyl and sulfonyl groups are attached to —C($R^b$)=CHR$^c$; and heterocycloamino, aryl and heteroaryl are substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

18. The compound of any of the previous embodiments 1-11, wherein E and $E^2$ are —Z'-(EWG')-C($R^b$)=CHR$^c$ where EWG' is —NR'CO— or —NR'SO$_2$—, preferably —NHCO— and Z is a bond, methylene or ethylene, preferably a bond.

19. The compound of any of the previous embodiments 1-11, wherein E and $E^2$ are —C($R^b$)=CHR$^c$.

20. The compound of the previous embodiment 19, wherein —C($R^b$)=CHR$^c$ is attached to carbon ring atom that is adjacent to nitrogen ring atom in $Ar^1$ or $Ar^3$.

21. The compound of any of the previous embodiments 17-20, wherein $R^c$ is cyano.

22. The compound of any of the previous embodiments 1-11 and 17-21, wherein $R^c$ is tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl,1-methylaminocycloprop-1-ylene, or 1-dimethylaminocycloprop-1-ylene.

23. The compound of any of the previous embodiments 1-11, wherein E and $E^2$ is a group of formula (a);

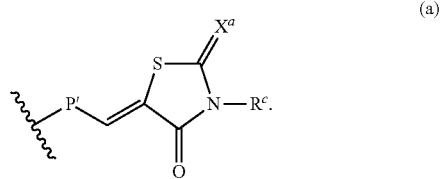

(a)

24. The compound of previous embodiment 23 wherein P' is alkylene, preferably methylene and $R^c$ is hydrogen, methyl, or cyclopropyl.

25. The compound of any of the previous embodiments 1-11, wherein E and $E^2$ is a group of formula (b);

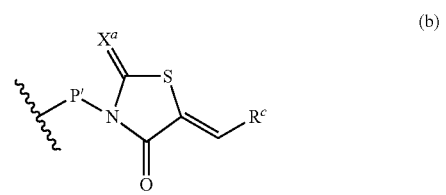

(b)

P is bond or alkylene, preferably methylene. Preferably, $R^c$ is tert-butyl, cyclopropyl, trifluoromethyl, 2,2,2-trifluoroethyl, 1-methyl-1-methylaminoethyl, 1-methyl-1-dimethylaminoethyl, 1-methyl-1-aminoethyl,1-methylaminocycloprop-1-ylene, or 1-dimethylaminocycloprop-1-ylene.

26. The compound of any of the previous embodiments 1-25, wherein $Ar^1$, $Ar^2$ and $Ar^3$ are phenyl.

27. The compound of the previous embodiment 26, wherein E, $E^1$ and $E^2$ are attached to the 3 or 4, preferably 3-position of the phenyl ring, the carbon attached to L, $L^1$ or azaindole ring being C-1.

28. The compound of any of the previous embodiment 26 or 27 wherein $R^5$, $R^6$, $R^7$, $R^8$, $R^9$ and $R^{10}$ are independently hydrogen, methyl, methoxy, trifluoromethyl, fluoro, chloro, cyano, or cyclopropyl, preferably hydrogen, methyl, methoxy, trifluoromethyl, cyano, fluoro or chloro, more preferably hydrogen, chloro, fluoro, methyl or methoxy. More preferably, $R^5$, $R^7$, and $R^9$ are hydrogen and $R^6$, $R^8$, and $R^{10}$ are at carbon ortho or para, preferably ortho, to carbon substituted with E, $E^1$ or $E^2$ respectively.

29. The compound of any of the previous embodiments 1-25, wherein $Ar^1$, $Ar^2$ and $Ar^3$ are heteroaryl, preferably pyridinyl, pyrimidinyl, or indolyl, preferably, pyrimidin-2-yl, pyridine-3-yl, pyridine-4-yl or indol-6-yl, even more preferably pyridine-3-yl or pyridine-4-yl.

30. The compound of the previous embodiment 29 wherein, E, $E^1$ and $E^2$ are attached to the 4-position of pyrimidin-2-yl, 2-position of pyridine-4-yl, 6-position of pyridine-3-yl, or 4-position of indol-6-yl, the ring nitrogen atom of the enumerated rings being position 1.

31. The compound of any of the previous embodiment 29 or 30 wherein $R^5$, $R^6$, $R^7$, $R^8$, $R^9$ and $R^{10}$ are independently hydrogen, methyl, methoxy, trifluoromethyl, fluoro, chloro, cyano, or cyclopropyl, preferably hydrogen, methyl, trifluoromethyl, cyano, fluoro or chloro, even more preferably hydrogen, fluoro, chloro, or methyl. More preferably, $R^5$, $R^7$, and $R^9$ are hydrogen and $R^6$, $R^8$, and $R^{10}$ are at carbon ortho or para to carbon substituted with E, $E^1$ or $E^2$ respectively.

32. The compound of any of the previous embodiments 1-25, wherein $Ar^1$, $Ar^2$ and $Ar^3$ are heterocyclyl, preferably piperidinyl, pyrrolidinyl, or 2,3-dihydroindolyl, preferably, pyrrolidin-3-yl, piperidin-3-yl, or 2,3-dihydroindol-6-yl.

33. The compound of the previous embodiment 32 wherein, E, $E^1$ and $E^2$ are attached to the ring nitrogen atom of pyrrolidin-3-yl, piperidin-3-yl or 2,3-dihydroindol-6-yl.

34. The compound of the previous embodiment 33 wherein $R^5$, $R^6$, $R^7$, $R^8$, $R^9$ and $R^{10}$ are independently hydrogen, methyl, trifluoromethyl, fluoro, chloro, cyano, or cyclopropyl, preferably hydrogen, methyl, trifluroromethyl, cyano, fluoro or chloro. More preferably, $R^5$, $R^7$, and $R^9$ are hydrogen and $R^6$, $R^8$, and $R^{10}$ are at carbon ortho or para to carbon substituted with E, $E^1$ or $E^2$ respectively. Within this group of compounds in one group of compounds E, $E^1$ or $E^2$ are —COC($R^b$)=CHR$^c$ where $R^b$ is preferably cyano, and $R^c$ is tert-butyl, isopropyl or cyclopropyl.

Embodiment (VIII)

VIII. In a further embodiment, the compound of Formula (IA) has the structure:

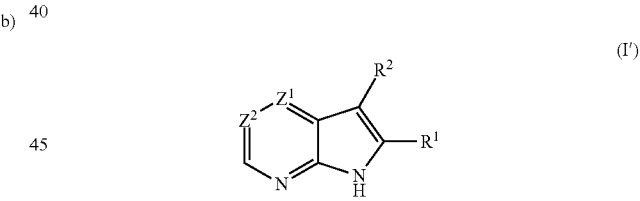

(I')

where:
 $Z^1$ is N or CR$^3$;
 $Z^2$ is N or CR$^4$ provided that at least one of $Z^1$ and $Z^2$ is N and both $Z^1$ and $Z^2$ are not simultaneously N;
 $R^1$ is hydrogen, alkyl, halo, haloalkyl, haloalkoxy, cyano or cycloalkyl; and
 (i) when $Z^1$ is CR$^3$ where is a ring of formula (A):

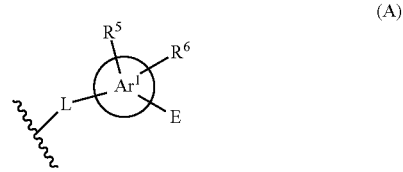

(A)

then, $R^2$ is hydrogen, alkyl, halo, haloalkyl, haloalkoxy, cyano, or cycloalkyl; and (ii) when $Z^2$ is $CR^4$ where $R^4$ a ring of formula (C):

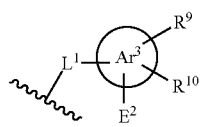

(C)

then, $R^2$ is hydrogen, alkyl, cycloalkyl, halo, cyano, acyl, or aminocarbonyl; and wherein:

L and $L^1$ are independently bond, —$CH_2$—, —NR—, —O—, CO, —S(O)n- (where n is 0-2), —NRCO—, —CONR—, or heteroalkylene (where R is hydrogen, alkyl or cycloalkyl);

$Ar^1$, $Ar^2$ and $Ar^3$ are independently aryl, heteroaryl, cycloalkyl or heterocyclyl;

$R^5$ and $R^9$ are independently hydrogen, alkyl, alkoxy, halo, haloalkyl, haloalkoxy, cyano, cycloalkyl;

$R^6$ and $R^{10}$ are independently hydrogen, alkyl, alkoxy, halo, haloalkyl, haloalkoxy, cyano or cycloalkyl, hydroxyalkyl, alkoxyalkoxy, aminoalkoxy, or alkylsulfonylalkoxy;

E and $E^2$ are independently:

(i) —P—CH=C($R^b$)(EWG) where P is a bond, $NR^a$ (where $R^a$ is hydrogen or alkyl), —O—, S, SO, $SO_2$, alkylene or heteroalkylene, $R^b$ is cyano, nitro, halo, haloalkyl, haloalkoxy, alkylthio, or alkylsulfonyl; or (ii) —Z'-(EWG')-C($R^b$)=$CHR^c$ where Z is bond, $NR^a$ (where $R^a$ is hydrogen or alkyl), —O—, S, SO, $SO_2$, alkylene, or heteroalkylene, $R^b$ is cyano, nitro, halo, haloalkyl, haloalkoxy, alkylthio, or alkylsulfonyl and $R^c$ is alkyl, substituted alkyl, haloalkoxy, cycloalkyl, cycloalkyleneNR$^d$R$^e$ where $R^d$ and $R^e$ are independently hydrogen, alkyl, or cycloalkyl; or (iii) a group of formula (a) or (b);

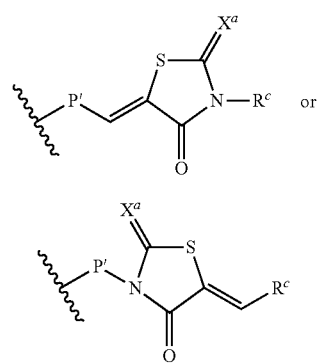

where P' is bond, alkylene or heteroalkylene, $X^a$ is O or N(H or alkyl) and $R^c$ is hydrogen, alkyl, substituted alkyl, haloalkoxy, cycloalkyl, or cycloalkyleneNR$^d$R$^e$ where $R^d$ and $R^e$ are independently hydrogen, alkyl, or cycloalkyl;

EWG is —$S(O_2)R'$, —$S(O)R'$, —$C(O)NH_2$, —$C(O)NHR^g$, —$C(O)NR^fR^g$, —$S(O_2)NH_2$, —$SO_2NHR^i$, —$SO_2NR^hR^i$, —$PO(OR')_2$, —$PO_3H_2$, —$PO(NR'_2)_2$, —CN, —CH(haloalkyl), —C(O)X', —COOH, —COOR', —C(O)R', —C(O)H, —P(O)(OR')OR", halo, heteroaryl, or aryl; wherein X' is independently halogen, R', R", $R^f$, $R^g$, $R^h$, and $R^i$ are independently hydrogen, alkyl, substituted alkyl, cycloalkyl, cycloalkyleneNR$^d$R$^e$ (where $R^d$ and $R^e$ are independently hydrogen, alkyl, or cycloalkyl) or $R^f$ and $R^g$ and/or $R^h$ and $R^i$ together with the nitrogen atom to which they are attached form heterocycloamino; and heterocycloamino, aryl and heteroaryl are optionally substituted with one, two or three substituents independently selected from alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl; and EWG' is bond, —CH(haloalkyl), —NR'—, —$S(O_2)$, —S(O), —CO—, —NR'CO—, —$NR'SO_2$

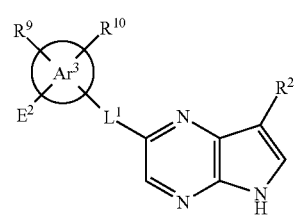

heteroaryl, or aryl; wherein each R' is independently hydrogen, alkyl, substituted alkyl, cycloalkyl; ring A is heterocycloamino where the carbonyl and sulfonyl groups are attached to —C($R^b$)=$CHR^c$; and heterocycloamino, aryl and heteroaryl are optionally substituted with one, two or three substituents independently selected from alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

Embodiment (aa)

(aa) Within embodiment (VIII), in one group of compounds $R^5$, $R^6$, $R^9$ and $R^{10}$ are independently hydrogen, alkyl, alkoxy, halo, haloalkyl, haloalkoxy, cyano, cycloalkyl; and L and $L^1$ are independently bond, —NR—, —O—, CO, —S(O) n- (where n is 0-2), —NRCO—, —CONR—, or heteroalkylene (where R is hydrogen, alkyl or cycloalkyl).

Embodiment (bb)

(bb) Within embodiments (VIII) and (aa), in one group of compounds, the compound of Formula (I') has the structure (Id):

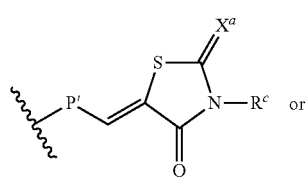

where $E^2$ is —P—CH=C($R^b$)(EWG) or a group of formula (a) or (b);

(a)

-continued

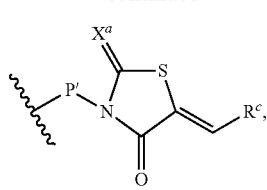
(b)

L$^1$ is a bond, —NR—, —O—, or —S(O)n- (where n is 0-2), preferably a bond, O or NH, more preferably NH, and Ar$^3$ is phenyl or heteroaryl.

(i) Within the groups in embodiment (bb) i.e, (VII,bb) and (aa,bb) and groups contained therein, in one group of compounds E$^2$ is —CH=C(R$^b$)(EWG).

(ii) Within the groups in embodiment (bb), in another group of compounds E$^2$ is

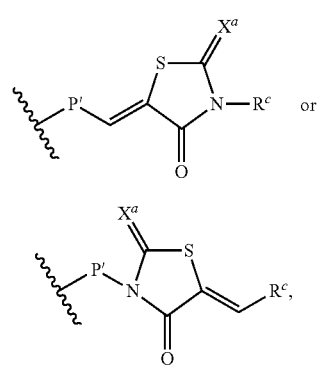

preferably

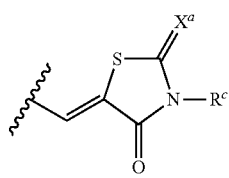

Preferably in group (a), R$^c$ is hydrogen, alkyl, substituted alkyl, or cycloalkyl, preferably R$^e$ is hydrogen, alkyl, or substituted alkyl, more preferably R$^c$ is hydrogen, methyl, ethyl, 2-dimethylaminoethyl, or 2-aminoethyl and X$^a$ is O.

Embodiment (cc)

(cc) Within the groups in embodiment (bb) above (VII,bb) and (aa,bb) and groups contained therein, in one group of compounds, the compound of Formula (I') has the structure (Ie):

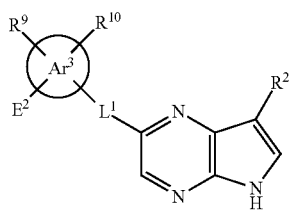

where L$^1$ is a bond, —NR—, —O—, or —S(O)n- (where n is 0-2), preferably L$^1$ is a bond and E$^2$ is —C(R$^b$)=CHR$^c$ where R$^c$ is alkyl, alkyl substituted with alkoxy, amino or dialkylamino, or cycloalkyl, preferably tert-butyl, isopropyl, or cyclopropyl.

Embodiment (dd)

(dd) Within embodiments (VIII), (aa), (bb) and (cc) above and groups contained therein, in one group of compounds, R$^2$ is acyl, preferably —COR where R is alkyl or cycloalkyl wherein cycloalkyl is optionally substituted with alkyl. Preferably R is 1-methylcyclohex-1-yl, isopropyl, isobutyl or tert-butyl, more preferably R is isopropyl or tert-butyl.

Embodiment (ee)

(ee) Within embodiments (VIII), (aa), (bb) and (cc) above and groups contained therein, in one group of compounds, R$^2$ is aminocarbonyl, preferably —NHCOR where R is alkyl or alkyl substituted with hydroxy. Preferably, R is ethyl, isopropyl, isobutyl, tert-butyl, —CH(CH$_3$)C(CH$_3$)$_3$, 2-methyl-2-hydroxymethylprop-1-yl, 3-hydroxy-3-methylbut-2-yl, more preferably R is isopropyl or tert-butyl.

Embodiment (ff)

(ff) Within embodiment (VIII) above, in one group of compounds, the compound of Formula (I') has the structure (If):

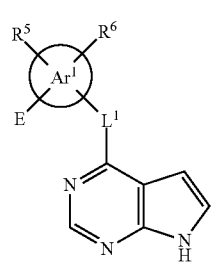

where L is a bond, —NR—, —O—, or —S(O)n- (where n is 0-2), preferably a bond, O or NH, more preferably NH, and Ar is phenyl or heteroaryl.

Within embodiment (ff), and groups contained therein, in one group of compounds E is —CH=C(R$^b$)(EWG).

Embodiment (gg)

(gg) With embodiment (VIII), (aa)-(ff) and groups contained therein, in one group of compounds R$^b$ is cyano.

Embodiment (hh)

(hh) With embodiment (VIII), (aa), (bb), (dd)-(gg) and groups contained therein, in one group of compounds EWG is —CO—NR$^f$R$^g$, —SO$_2$NR$^h$R$^i$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and/or R$^h$ and R$^i$ together with the nitrogen atom to which they are attached form heterocycloamino), aryl or heteroaryl wherein said heterocycloamino, aryl and heteroaryl are optionally substituted with one, two or three substituents independently selected from alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl. Preferably, EWG is pyridine-2-yl, pyridine-3-yl, pyridine-4-yl, pyrrol-1-yl, pyrazol-1-yl, thiazol-2-yl, dimethylaminocarbonyl, methylaminocarbonyl, isopropylaminocarbonyl, tert-butylaminocarbonyl, 3-hydroxy-1-methylpropylaminocarbonyl, azetidin-1-ylcarbonyl, 4-hydroxyazetidin-1-ylcarbonyl, pyrrolidin-1-ylcarbonyl, 4-ethylpiperazin-1-ylcarbonyl, or 2,6-dimethylmorpholin-4-ylcarbonyl.

Embodiment (ii)

(ii) With embodiment (VIII), (aa), (bb), (dd)-(gg) and groups contained therein, in one group of compounds EWG is —C(O)NR$^f$R$^g$, —SO$_2$NR$^h$R$^i$, —COOR', —SO$_2$R' or 5-membered heteroaryl; wherein R' is alkyl, R$^f$ and R$^i$ are independently hydrogen or alkyl, and R$^g$ and R$^h$ are independently alkyl, alkyl substituted with hydroxy, alkoxy, amino, alkylamino or dialkylamino, or R$^f$ and R$^g$ together with the nitrogen atom to which they are attached form heterocycloamino; said heterocycloamino and 5-membered heteroaryl are optionally substituted with one, two or three substituents independently selected from alkyl, alkoxy, hydroxyl, cyano, halo, haloalkyl, haloalkoxy, alkylsulfonyl, carboxy, or alkoxycarbonyl. Preferably, EWG is —CONH$_2$, —CONHtert-butyl, —CONHethyl, —CON(CH$_3$)$_2$, methoxycarbonyl, ethoxycarbonyl, methylsulfonyl, azetidin-1-ylcarbonyl, morpholin-4-ylcarbonyl, piperazin-1-ylcarbonyl, 4-methylpiperazin-1-ylcarbonyl, piperidin-1-ylcarbonyl, thiazol-2-yl, oxazol-2-yl, 1,2,4-triazol-1-yl, dimethylaminosulfonyl, or isoxazol-5-yl, more preferably morpholin-4-ylcarbonyl.

Embodiment (jj)

(jj) With embodiment (VIII) and (aa)-(ii), and groups contained therein, in one group of compounds, Ar$^1$ and Ar$^3$ are independently phenyl or six membered heteroaryl, preferably phenyl or pyridinyl. Within these groups of compounds in one group of compounds, Ar$^1$ is:

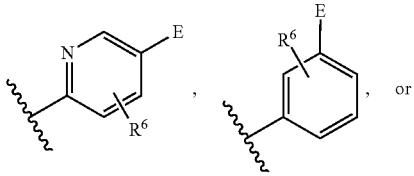

preferably

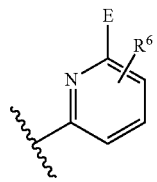

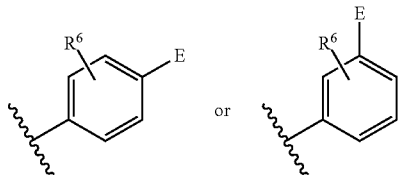

more preferably

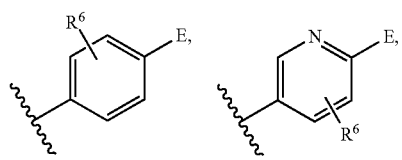

Within these groups of compounds in another group of compounds, Ar$^3$ is:

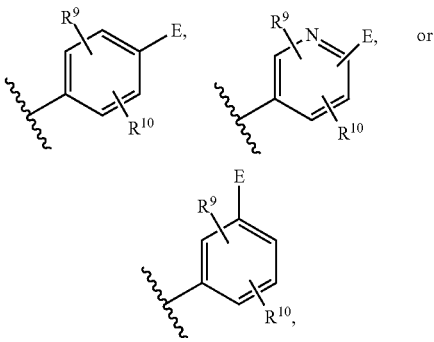

preferably,

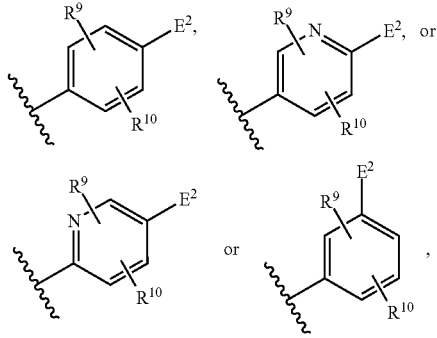

more preferably,

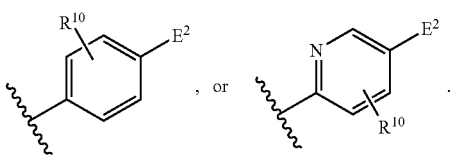

Embodiment (kk)

(kk) Within the groups above in embodiments (jj), in one group of compounds $R^5$ and $R^9$ are independently hydrogen, alkyl, alkoxy, halo, cyano, haloalkyl, or haloalkoxy and $R^6$ and $R^{10}$ are independently hydrogen, alkyl, alkoxy, halo, haloalkyl, haloalkoxy, cyano, cycloalkyl, hydroxyalkoxy, alkoxyalkyl, aminoalkoxy, or alkylsulfonylalkoxy; preferably $R^5$ and $R^9$ are hydrogen, methyl, methoxy, chloro, fluoro, trifluoromethyl, or cyano and $R^6$ and $R^{10}$ are independently hydrogen, methyl, methoxy, chloro, fluoro, trifluoromethyl, cyano, 2-methoxyethyloxy, 3-methoxypropyloxy, 2-aminoethyloxy, 3-aminopropyloxy, 2-methylaminoethyloxy, 3-methylaminopropyloxy, 2-dimethylaminoethyloxy, 3-dimethylaminopropyloxy, 2-diethylaminoethyloxy, 3-diethylaminopropyloxy, 2-piperidin-1-ylethyloxy, 3-piperidin-1-ylpropyloxy, 2-piperazin-1-ylethyloxy, 3-piperazin-1-ylpropyloxy, 2-(4-methylpiperazin-1-yl)ethyloxy, 3-(4-methylpiperazin-1-yl)propyloxy, 2-(4-ethylpiperazin-1-yl)ethyloxy, 3-(4-ethylpiperazin-1-yl)propyloxy, 2-morpholin-4-ylethyloxy, 3-morpholin-4-ylpropyloxy, 2-methylsulfonylethyloxy, 3-methylsulfonylpropyloxy, 2-hydroxyethyloxy, or 3-hydroxypropyloxy, more preferably $R^5$ and $R^9$ are hydrogen and $R^6$ and $R^{10}$ are hydrogen, methyl, methoxy, chloro, fluoro, trifluoromethyl, cyano, 2-methoxyethyloxy, 3-methoxypropyloxy, 2-aminoethyloxy, 3-aminopropyloxy, 2-methylaminoethyloxy, 3-methylaminopropyloxy, 2-dimethylaminoethyloxy, 3-dimethylaminopropyloxy, 2-diethylaminoethyloxy, 3-diethylaminopropyloxy, 2-piperidin-1-ylethyloxy, 3-piperidin-1-ylpropyloxy, 2-piperazin-1-ylethyloxy, 3-piperazin-1-ylpropyloxy, 2-(4-methylpiperazin-1-yl)ethyloxy, 3-(4-methylpiperazin-1-yl)propyloxy, 2-(4-ethylpiperazin-1-yl)ethyloxy, 3-(4-ethylpiperazin-1-yl)propyloxy, 2-morpholin-4-ylethyloxy, 3-morpholin-4-ylpropyloxy, 2-methylsulfonylethyloxy, 3-methylsulfonylpropyloxy, 2-hydroxyethyloxy, or 3-hydroxypropyloxy and are located at carbon ortho to the carbon substituted with E or $E^2$.

General Synthetic Schemes

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula (I) where $Z^1$ is $CR^3$ where $R^3$ is a ring of formula (A), $Z^2$ is nitrogen, L is NR, O or S, and E, $Ar^1$, $R^1$, $R^2$, $R^5$ and $R^6$, are as defined above can be prepared as illustrated and described in Schemes A and B below.

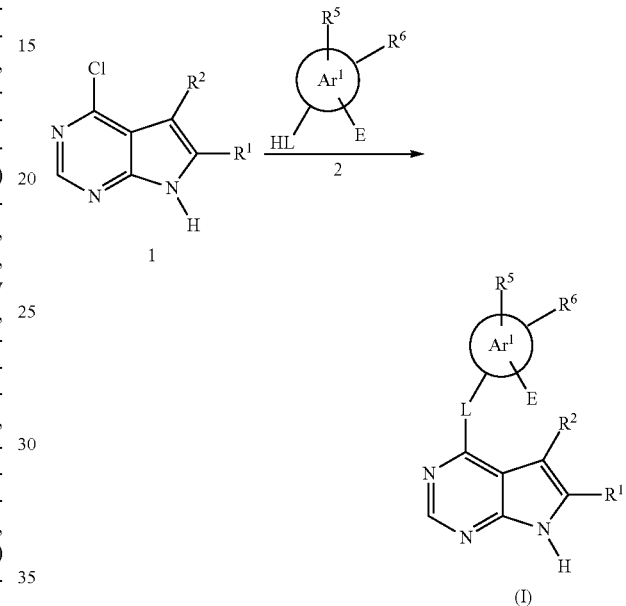

Scheme A

For compounds of Formula (I) where L is an NR, O or S, as a first step, coupling of pyrrolopyrimidines of formula 1 by nucleophilic aromatic substitution of the chlorine in the 4-position of the pyrrolopyrimidines with an amine, alcohol or thiol of formula 2 where LH is $NH_2$, NHR, OH or SH respectively and $Ar^1$ and $R^5$, $R^6$ and E are as defined above, provides a compound of Formula (I). The nucleophilic aromatic substitutions can be carried out under standard methods from the literature run neat or in common solvents, such as toluene, N,N-dimethylformamide (DMF), tetrahydrofuran (THF), N-methyl pyrroline (NMP) and the like, using a base such as pyridine, diisopropyl ethyl amine (DIPEA), potassium t-butoxide (KOtBu), sodium hydride, lithium hydroxide (LiOH), potassium carbonate ($K_2CO_3$) or cesium carbonate ($Cs_2CO_3$) or an acid such as HCl or a Lewis acid such as zinc chloride ($ZnCl_2$). The reactions are carried out at room temperature to 150° C. Coupling reactions can also be performed under standard microwave conditions. Compounds of formula 1 and formula 2 are either commercially available or can be readily prepared by methods well known in the art. The NH of pyrrolopyrimidine compounds of Formula 1 can be optionally protected with protecting groups such groups as trimethylsilylethoxymethyl (SEM) or tetrahydropyranyl (THP) and the like, and can be removed following coupling reactions with compounds of formula 2 under standard deprotection conditions such as acetic acid in THF or trifluoroacetic acid in methanol or tetrabuylammonium fluoride (TBAF) in dichloromethane and the like at room temperature, to provide compounds of Formula (I).

Compounds of Formula (I) with L as sulfoxide or sulfone can be prepared by oxidation of compounds of Formula (I) where L is sulfide. The oxidation can occur under standard conditions using oxidizing agents such as MCPBA or oxone at room temperature in solvents such as methylene chloride, methanol and the like, utilizing one equivalent of oxidizing reagent to prepare sulfoxides and two equivalents for sulfones.

For compounds of Formula (I) where L is a bond, coupling of pyrrolopyrimidines of formula 1 with a boronic acid or boronate ester compound of formula 2 with HL equals $B(OH)_2$ or $B(OR')_2$ and $Ar^1$ and $R^5$, $R^6$ are as defined above, under Suzuki coupling reaction conditions provides a compound of Formula (I). The Suzuki coupling reaction can be carried out neat or in organic solvents (such as toluene, benzene, N,N-dimethylformamide (DMF), tetrahydrofuran, methanol, ethanol, acetonitrile, dimethoxyethane, dioxane, acetone and the like) or water in the presence of base (such as sodium ethylate, sodium hydroxide, potassium hydroxide, sodium bicarbonate, potassium bicarbonate, potassium carbonate, sodium carbonate, triethylamine, and the like) and a palladium catalyst (such as tetrakis(triphenylphosphine)palladium, dichlorobis(triphenylphosphine)palladium, palladium acetate, and the like). The reaction is carried out at room temperature to 120° C. Suzuki coupling reactions can also be carried out under standard microwave conditions. Compounds of formula 1, formula 2, including boronic acids and boronate esters of formula 2, are either commercially available or can be readily prepared by methods well known in the art.

It will be recognized by a person skilled in the art that precursors to group E can be substituted at any step in the synthetic procedure illustrated in Scheme A above and converted to the E group as defined above at alternate stages in the synthetic process based on feasibility of the transformations. Some such examples are described below:

1. Synthesis of compounds of Formula (I) when E=—P—CH=C($R^b$)(EWG) and where E is a group of formula

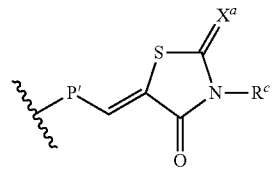

or a group of formula

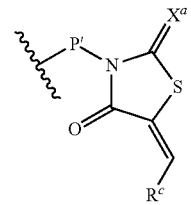

are illustrated and described below in Methods (a)-(f).

Method (a)

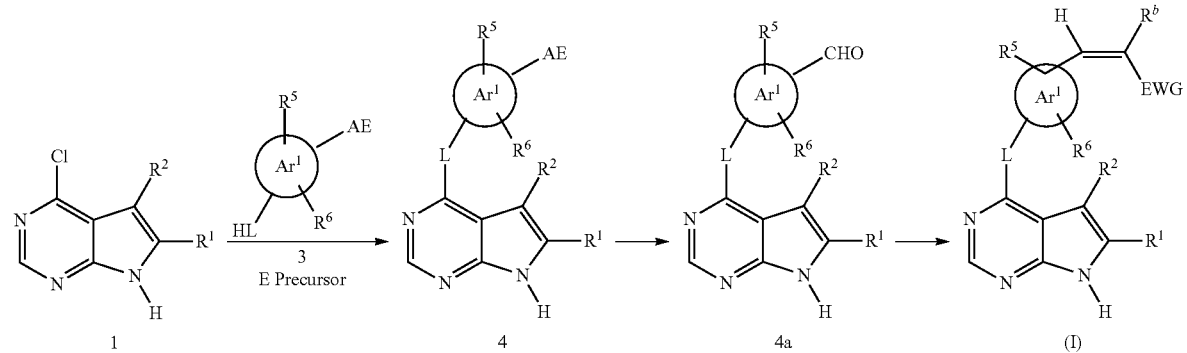

Method (b)

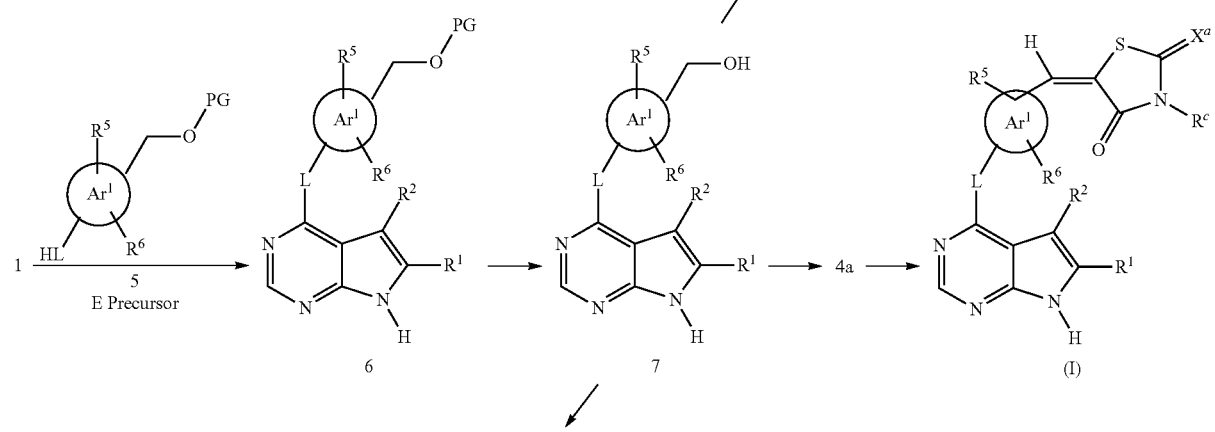

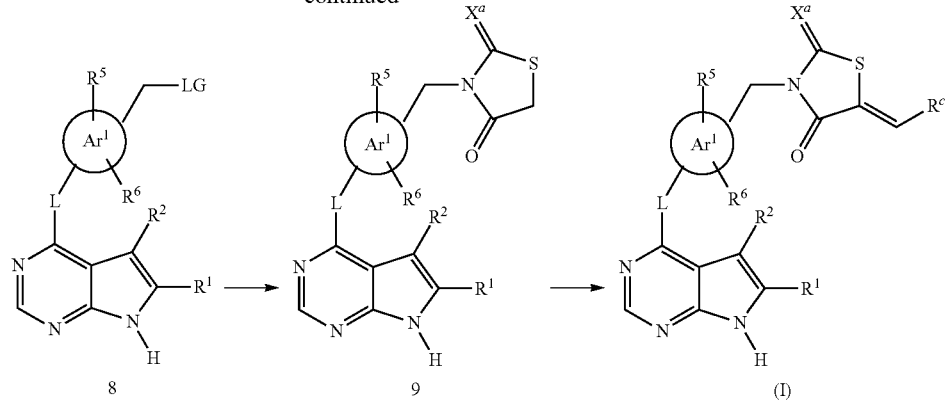

Method (a)

Coupling of a compound of formula 1 with an E precursor of formula 3 bearing a suitable aldehyde equivalent (AE) under the various nucleophilic aromatic substitution conditions or Suzuki conditions as described in Scheme A, provides a compound of formula 4, where $R^1$, $R^2$, $R^5$ and $R^6$, $Ar^1$ and L are as defined above. The aldehyde equivalent (AE) is presented as a functional group that can be converted to the aldehyde in a simple transformation. Examples include: an acetal which can release the aldehyde under acidic conditions; a thioacetal which can release the aldehyde using mercuric or silver salts; incorporation of an alkene which can be oxidized with a mixture of osmium tetroxide and sodium periodate; cleavage of an alkene with ozone; deprotection of a primary alcohol and subsequent oxidation to the aldehyde. Several literature examples are known for generation of an aldehyde and selection of the appropriate aldehyde precursor is dependent on stability to other synthetic sequence transformations. Conversion of AE in formula 4 to the aldehyde compound of formula 4a can be achieved by any number of methods dependent on the form of AE as described above. Condensation of the aldehyde group in compound 4a with a compound of formula $R^bCH_2EWG$, where $R^b$ and EWG are as defined above, under standard condensation reaction conditions such as using a base such as piperidine and the like, in the presence or absence of acetic acid and the like in solvents such as ethanol and the like at temperatures ranging from room temperature to reflux then provides a compound of Formula (I) where $E=CH=C(R^b)(EWG)$. Compounds of formula $R^bCH_2EWG$ are either commercially available or they can be prepared by methods well known in the art. For example, 2-cyano-N,N-dimethylacetamide and 2-trifluoromethyl-N,N-dimethylacetamide are commercially available.

Method (b):

Alternatively, an E precursor bearing a hydroxyl protected derivative of formula 5 can be used in lieu of compound of formula 3, to provide compounds of formula 6. Protecting groups consist of such groups as t-butyldimethylsilyl and THP and can be removed under standard deprotection conditions such as acetic acid in THF and the like at room temperature, to provide compounds of formula 7. Oxidation of the alcoholic group of compounds of formula 7 provides the corresponding aldehyde of formula 4a. The oxidation reaction can be carried out with oxalyl chloride, DMSO followed by triethyl amine at temperatures ranging from −78° C. to room temperature in solvents such as dichloromethane and the like (Swern oxidation conditions) or by Dess-Martin periodinane (DMP) and the like. Compound 4a can be converted to a compound of Formula (I) where E is —CH=C($R^b$)(EWG) as described in Method (a) above.

Alternatively, aldehyde of formula 4a can be condensed with 2,4-thiazolidenedione in the presence of ammonium acetate and acetic acid at temperatures ranging from room temperature to 120° C. to yield compounds of Formula (I) where E is a group of formula (a) as defined above.

Alternatively, the hydroxyl group in the compound of formula 7 can be converted into a leaving group (LG) such as halo, tosylate, mesylate or triflate, and the like to provide a compound of formula 8 by methods well known in the art. For example, a compound of formula 8 where the leaving group is tosylate or mesylate can be prepared by reacting a compound of formula 7 with toluenesulfonyl chloride or methanesulfonyl chloride respectively in the presence of a base such as pyridine, and the like and in an organic solvent such as dichloromethane, and the like, at temperatures from −20° C. to reflux. Alkylation of compounds of formula 8 with 2,4-thiazolidenedione in the presence of a base such as sodium hydride or potassium tert-butoxide, and the like in an organic solvent such as toluene or dimethylformamide, THF, and the like, at temperatures from 0° C. to 10° C. provides a compound of formula 9. Condensation of compound 9 with an aldehyde of formula $R^cCHO$, such as cyclopropyl aldehyde or t-butyl aldehyde, and the like in an organic solvent such as ethanol and at temperatures ranging from 0° C. to reflux yield compounds of Formula (I) where E is a group of formula (b).

Method (c)

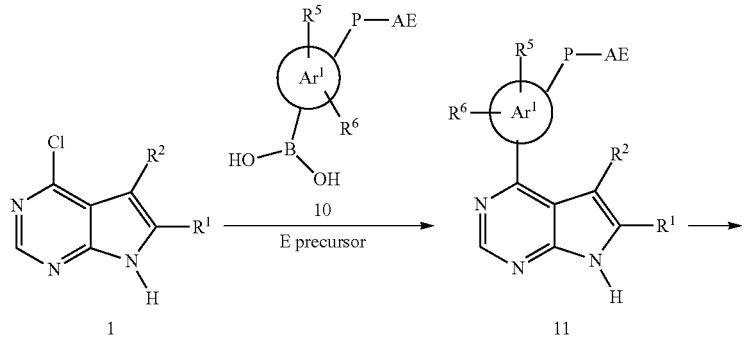

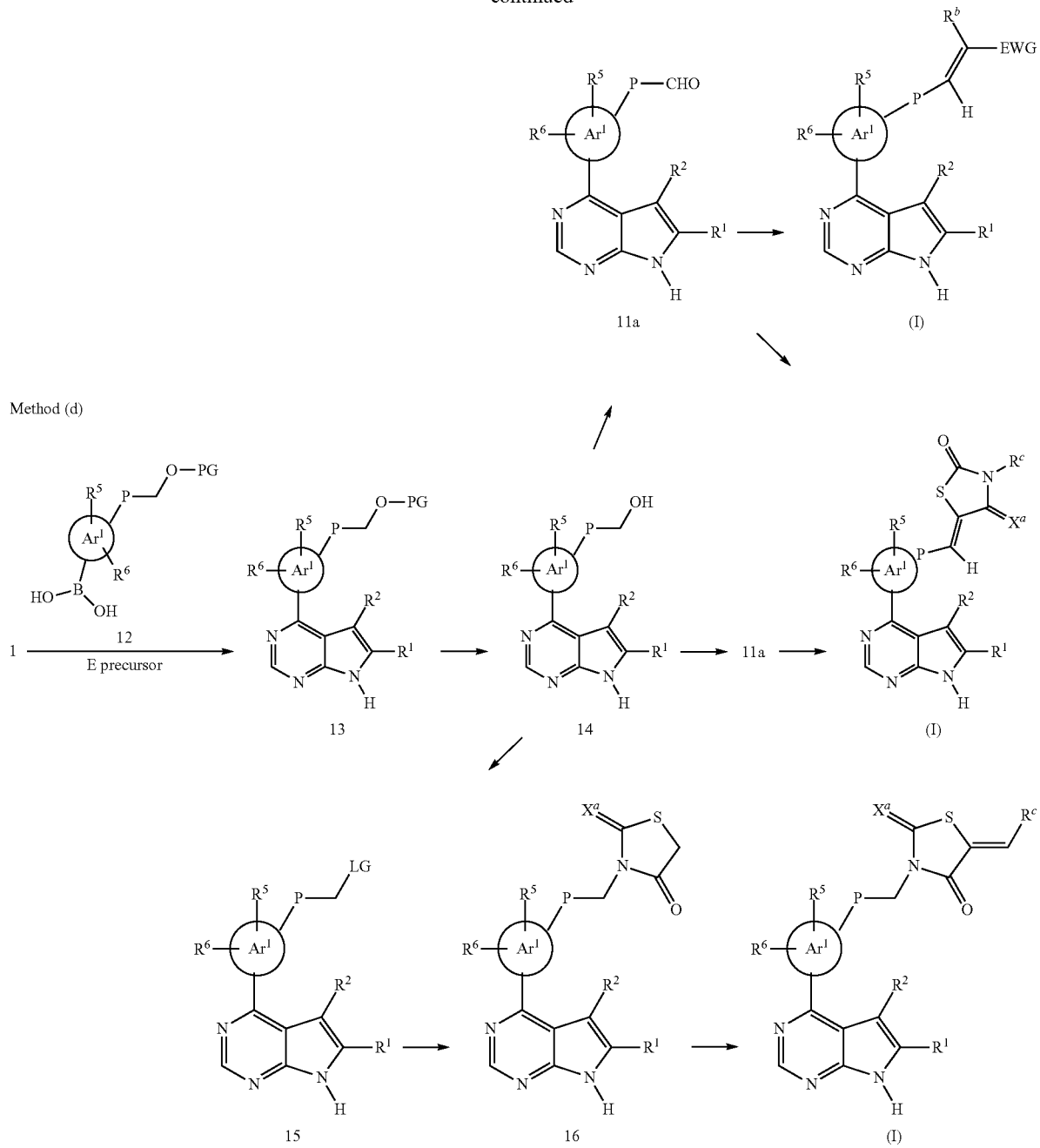

Method (c):

In a more general example of Method (a), cross coupling of a compound of formula 1 with an E precursor compound of formula 10 bearing a suitable aldehyde equivalent (AE) as described in method (a) under Suzuki conditions as described in Scheme A, provides a compound of formula 11 where $R^1$, $R^2$, $R^5$, $R^6$, $Ar^1$, L and P are as defined above. Conversion of AE in formula 11 to the aldehyde 11a can be achieved by any number of methods dependent on the form of AE as described previously. In analogy to Method (a), compounds of formula 11a can be converted to compounds of Formula (I) where E=—P—CH=C($R^b$)(EWG). The NH of pyrrolopyrimidine compounds of formula 1 can be optionally protected with protecting groups such groups as trimethylsilylethoxymethyl (SEM) or tetrahydropyranyl (THP) and the like and can be removed in the scheme above at the appropriate step under standard deprotection conditions such as acetic acid in THF or trifluoroacetic acid in methanol or fluoride anion such as tetrabuylammonium fluoride (TBAF) and the like in dichloromethane and the like at room temperature, to provide compounds of formula (I).

Method (d):

In a more general example of Method (b), an E precursor bearing a hydroxyl protected derivative 12 can be used in lieu of compound of formula 10, to provide compounds of formula 13. In analogy to Method (b), compounds of formula 13 can be converted to compounds of Formula (I) where E=—P—CH=C($R^b$)(EWG) and compounds of Formula (I) where E is a group of formula (a) and formula (b) as defined above.

Synthesis of compounds of Formula (I) when precursors to E is Z'-(EWG')-C($R^b$)=CHR$^c$ where Z' and EWG' are as defined above is illustrated and described below as methods (e) and (f).

Method (e)

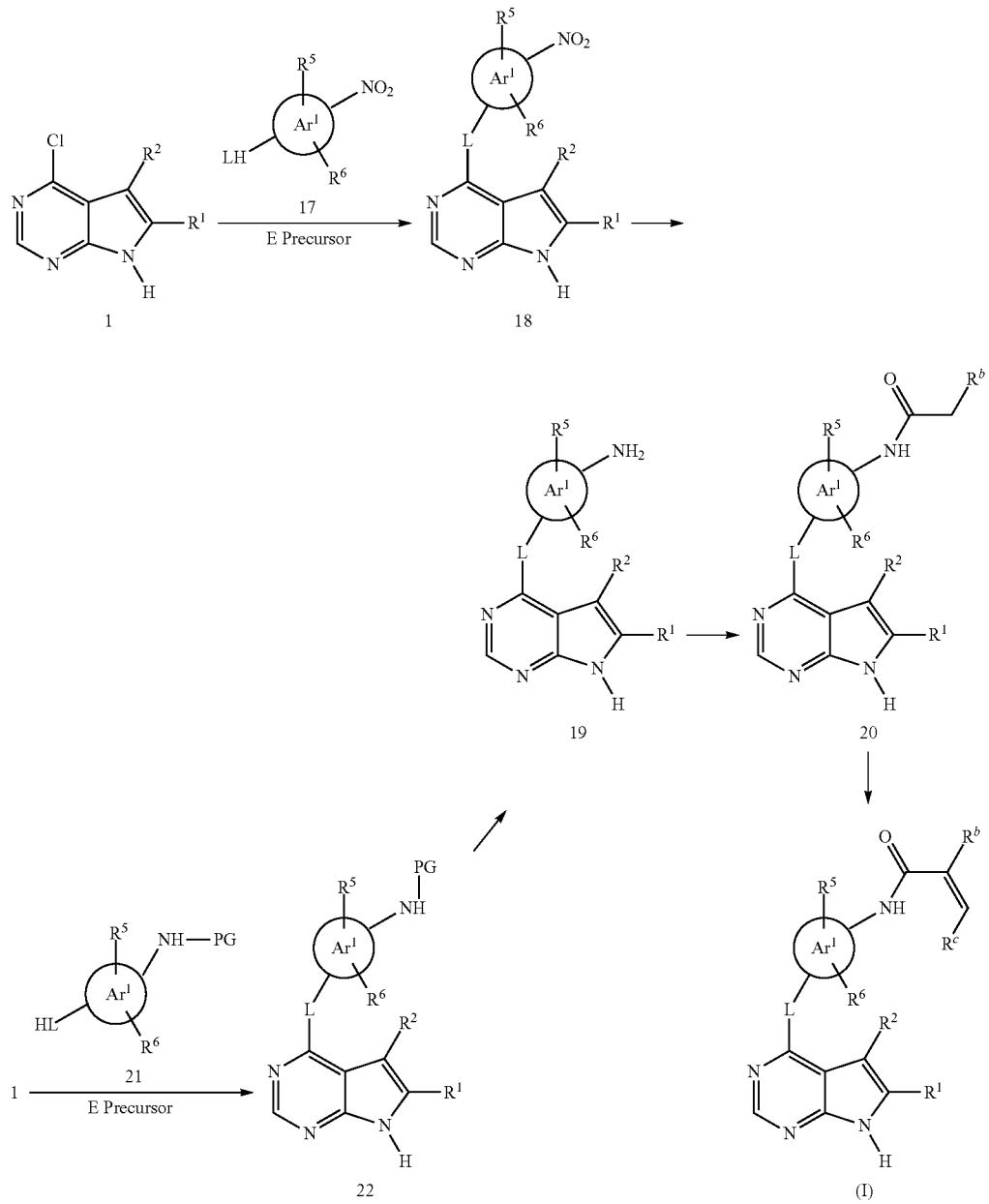

in a suitable solvent such as acetic acid and the like, or with catalytic palladium on charcoal under a hydrogen atmosphere in suitable solvents such as methanol, ethanol and the like to provide a compound of formula 19. Coupling of compounds of formula 19 with a compound of formula R$^b$CH$_2$CO$_2$H such as 2-cyanoacetic acid or 2-trifluoromethylacetic acid, under standard amide coupling conditions such as carbon diimidazole (CDI) and the like or an acid derivative thereof provides a compound of formula 20. Subsequent condensation of a compound of formula 20 with aldehydes of formula R$^c$CHO where R$^c$ is as defined above e.g., t-butyl or cyclopropyl aldehyde, in an organic solvent such as ethanol and the like in the presence of bases such as piperadine and the like at temperatures ranging from 0° C. to reflux provides a compound of Formula (I). It will recognized by a person of ordinary skill Method (e)

Coupling of a compound of formula 1 with an E precursor compound of formula 17 under the various nucleophilic aromatic substitution conditions or Suzuki conditions as described in Scheme A, provides compounds of formula 18 where Ar$^1$, R$^1$, R$^2$, R$^5$, —R$^6$ and L are as defined above. Reduction of nitro substituent of compound 18 may be accomplished by treatment with a reducing agent such as zinc in the art that the EWG' moiety can be assembled at multiple points throughout the synthetic scheme and standard protecting group (PG) strategies can be employed as required.

Alternatively, coupling of a compound of formula 1 with an E precursor compound of formula 21, containing a protected amine (suitable nitrogen protecting groups (PG) include t-butyloxycarbonyl (BOC), carbobenzyloxy (Cbz), or 2-trimethylsilyl-ethoxymethyl (SEM)) and bearing an alcohol, under Suzuki conditions as described in Scheme A, provides a compound of formula 22 where $Ar^1$, $R^1$, $R^2$, $R^5$, —$R^6$ and L are as defined above. Removal of the amino protecting group can be effected using strong acid (TFA or HCL in the case of a Boc group, hydrogenolysis in the case of Cbz, or fluoride anion to remove the SEM), to provide the amine of formula 19, which can be carried onto compounds of Formula (I) as described above.

Method (f)

In a more general example of Method (e), cross coupling of a compound of formula 1 with an E precursor compound of formula 23 under Suzuki conditions as described in Scheme A, provides a compound of formula 24 where Z', $Ar^1$, $R^1$, $R^2$, $R^5$, —$R^6$, and L are as defined above. In analogy to Method (e), compounds of formula 24 can be converted to compounds of Formula (I) where E is Z'-(EWG')-C($R^b$)=CH$R^c$ and $R^b$, $R^c$ and EWG' are as defined above.

Alternatively, an E precursor compound bearing a protected amine derivative of formula 27 can be used in lieu of compound of formula 23, providing a compound of formula 28 where Z, $Ar^1$, $R^1$ $R^2$, $R^5$, —$R^6$ and L are as defined above. Removal of the amino protecting group of compounds of formula 28 provides a compound of formula 25, which can be carried onto compounds of Formula (1) as described above.

Method (f)

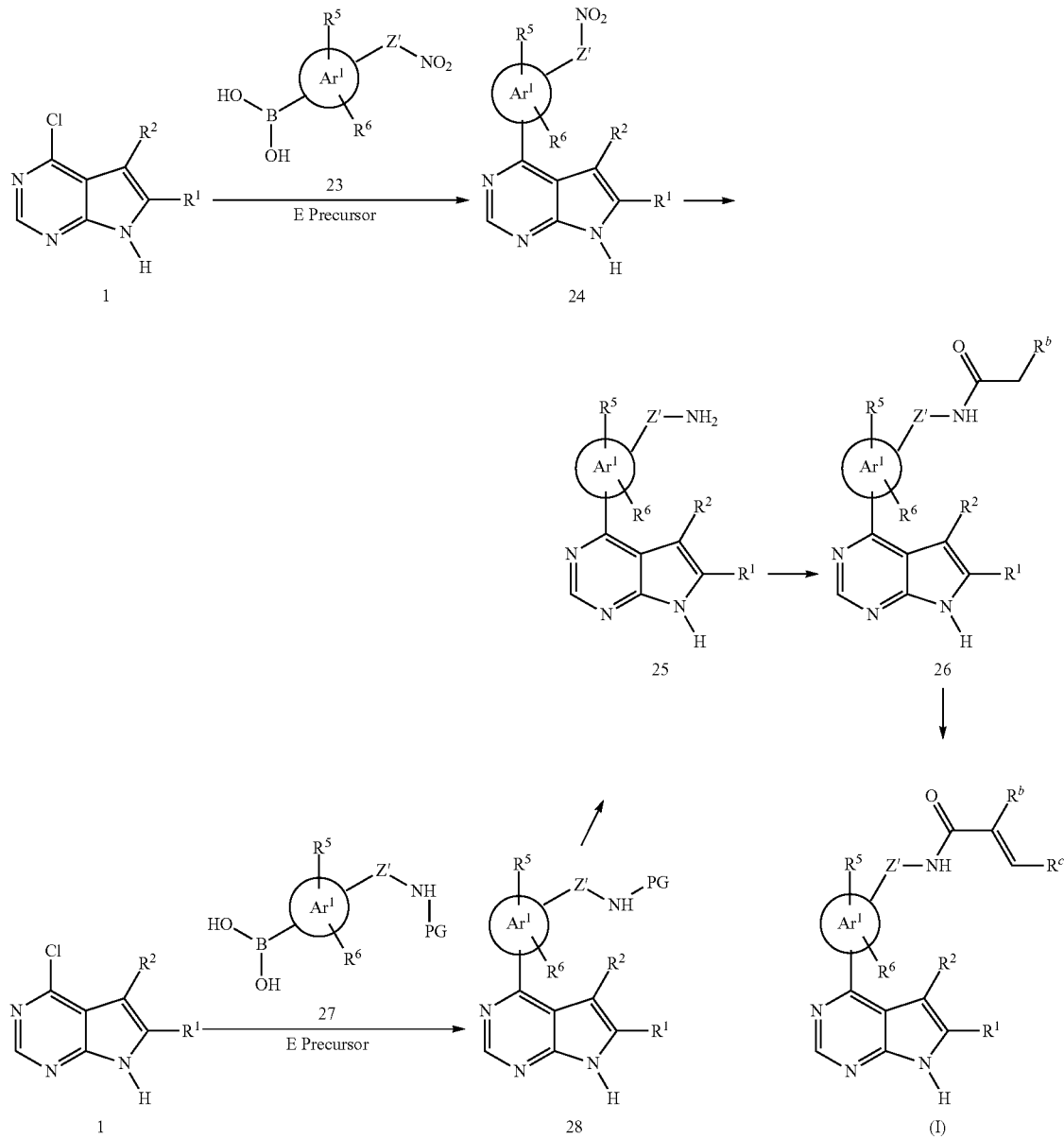

Compounds of Formula (I) where $L^1$ is an NH or NR and $Ar^3$, $R^1$, $R^2$, $R^9$, $R^{10}$ and $E^2$ are as defined above can be prepared as described in Scheme B below.

Scheme B

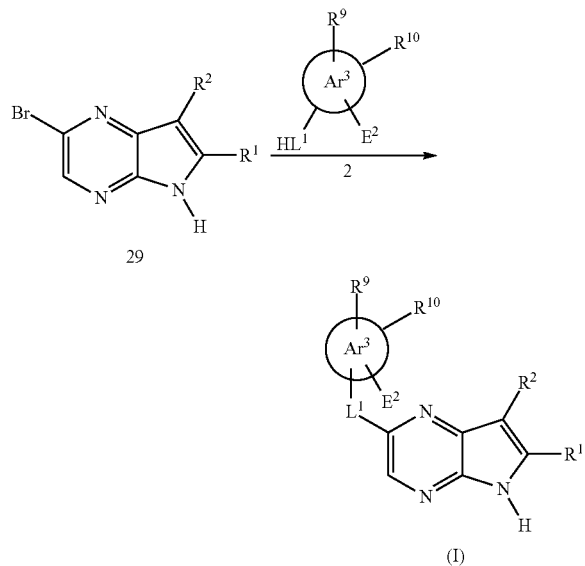

For compounds of Formula (I) where $L^1$ is an amine, coupling of pyrrolopyrimidines of formula 29 by copper catalyzed coupling of the bromine in the 5-position of the pyrrolopyrimidines with an amine of formula 2 where L'H is $NH_2$ or NHR respectively and Ar, $R^1$, $R^2$, $R^9$, $R^{10}$ and $E^2$ are as defined above, provides a compound of formula (I). The copper catalyzed coupling reactions can be carried out under standard methods from the literature with or without solvents, such as dimethylsulfoxide (DMSO), N,N-dimethylformamide (DMF), tetrahydrofuran (THF), N-Methyl Pyrroline (NMP), toluene and the like, using a base such as potassium carbonate ($K_2CO_3$) or cesium carbonate ($Cs_2CO_3$) and the like in the presence of proline and copper (I) iodide. The reactions are carried out at room temperature to 150° C. Coupling reactions can also be performed under standard microwave conditions. The coupling reactions between compounds of formula 1 and amines of formula 2 can be alternatively accomplished using palladium catalyzed Buchwald or Hartwig conditions commonly reported in the literature. By example, the amine of formula 2 can be combined with base such as cesium carbonate, potassium carbonate and the like with palladium catalysts such as palladium acetate and the like and BINAP and the like in solvents such as THF, dioxane, toluene and the like at temperatures from room temperature to reflux. Alternatively, direct nucleophilic aromatic substitution of the amine with the bromide of formula 1 as described in scheme A can form compounds of Formula (I). Compounds of formula 1 and formula 2 are either commercially available or can be readily prepared by methods well known in the art. The NH of pyrrolopyrimidine compounds of formula 1 can be optionally protected with protecting groups such groups as trimethylsilylethoxymethyl (SEM) or tetrahydropyranyl (THP) and the like and can be removed following coupling reactions with compounds of formula 2 under standard deprotection conditions such as acetic acid in THF or trifluoroacetic acid in methanol or tetrabuylammonium fluoride (TBAF) in dichloromethane and the like at room temperature, to provide compounds of formula (I).

For compounds of Formula (I) where $L^1$ is an O, coupling of pyrrolopyrimidines of formula 29 by nucleophilic aromatic substitution of the bromine in the 5-position of the pyrrolopyrimidines with an alcohol of formula 2 as described in Scheme A where $L^1H$ is OH and $Ar^3$, $R^1$, $R^2$, $R^9$-$R^{10}$ and $E^2$ are as defined above, provides a compound of formula (I). Alternatively, the coupling of the alcohol of formula 2 with bromides of formula 29 can be accomplished via palladium catalyzed coupling conditions using potassium phosphate and the like and di-tert-butylphosphino-2'-(N,N-dimethylamino)biphenyl and the like and palladium acetate and the like in solvents such as toluene and the like at temperatures from room temperature to reflux to provide a compound of formula (I). Coupling reactions can also be performed under typical microwave conditions.

For compounds of Formula (I) where $L^1$ is S, coupling of pyrrolopyrimidines of formula 29 by nucleophilic aromatic substitution of the bromine in the 5-position of the pyrrolopyrimidines with thiols of formula 2 can be accomplished as described in Scheme A where $L^1H$ is SH and $Ar^3$, $R^1$, $R^2$, $R^9$-$R^{10}$ and $E^2$ are as defined above, to provide a compound of formula (I). Alternatively, the coupling of the thiol of formula 2 with bromides of formula 1 can be accomplished via copper catalyzed coupling conditions to provide a compound of formula (I). Coupling reactions can also be performed under typical microwave conditions.

For Compounds of Formula (I) with $L^1$ as sulfoxide or sulfone can be prepared by oxidation of compounds of Formula (I) where L is sulfide. The oxidation can occur under standard conditions using oxidizing agents such as MCPBA or ozone at room temperature in solvents such as methylene chloride, methanol and the like, utilizing one equivalent of oxidizing reagent to prepare sulfoxides and two equivalents for sulfones.

Alternatively, for compounds of Formula (I) where $L^1$ is a bond, coupling of pyrrolopyrimidines of formula 29 with a boronic acid or boronate ester compound of formula 2 with $L^1H$ equals $B(OH)_2$ or $B(OR')_2$ and $Ar^3$, $R^1$, $R^2$, $R^9$-$R^{10}$ and $E^2$ are as defined above, under Suzuki coupling reaction conditions provides a compound of Formula (I). The Suzuki coupling reaction can be carried out neat or in organic solvents (such as toluene, benzene, N,N-dimethylformamide (DMF), tetrahydrofuran, methanol, ethanol, acetonitrile, dimethoxyethane, dioxane, acetone and the like) or water in the presence of base (such as sodium ethylate, sodium hydroxide, potassium hydroxide, sodium bicarbonate, potassium bicarbonate, potassium carbonate, sodium carbonate, triethylamine, and the like) and a palladium catalyst (such as tetrakis(triphenylphosphine)-palladium, dichlorobis(triphenylphosphine)palladium, palladium acetate, and the like). The reaction is carried out at room temperature to 120° C. Suzuki coupling reactions can also be carried out under standard microwave conditions. Compounds of formula 1, formula 2, including boronic acids and boronate esters of formula 2, are either commercially available or can be readily prepared by methods well known in the art.

It will be recognized by a person skilled in the art that precursors to group $E^2$ can be substituted at any step in the synthetic procedure illustrated in Scheme A above and converted to the $E^2$ group as defined above at alternate stages in the synthetic process based on feasibility of the transformations. Some such examples are described below:

Synthesis of compounds of Formula (I) when $E^2$=—P—CH=C($R^b$)(EWG) and where $E^2$=a group of formula
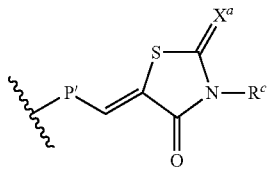
or a group of formula
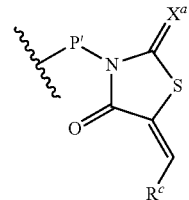
are illustrated and described below in Methods (g)-(l), using the preparation of $E^2$ as examples.
Method (g)
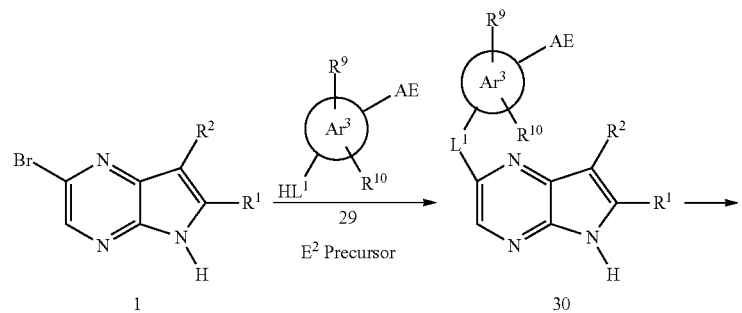
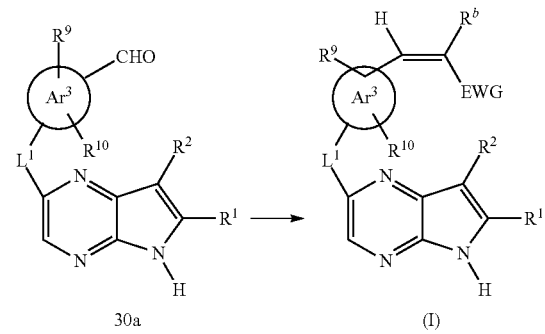
Method (h)
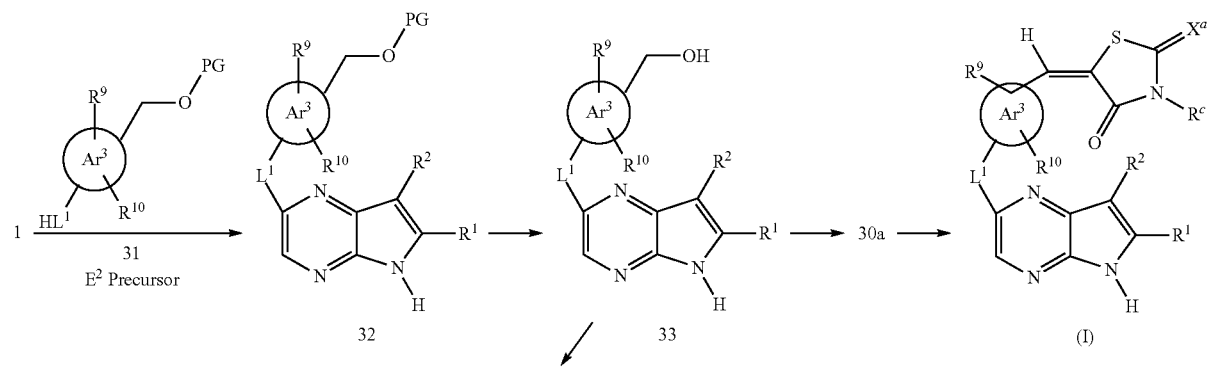

-continued

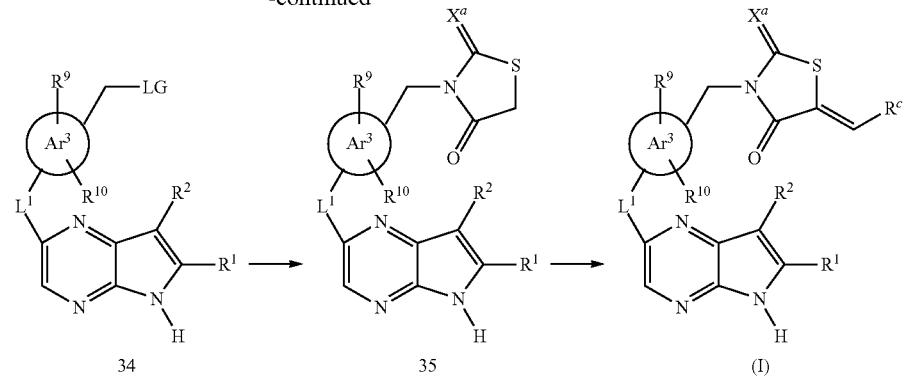

Method (g)

Coupling of a compound of formula 1 with an $E^2$ precursor of formula 29 bearing a suitable aldehyde equivalent (AE) as described in method (a) under the various nucleophilic aromatic substitution conditions, or copper catalyzed, or palladium catalyzed conditions including Suzuki conditions as described in Scheme B, provides a compound of formula 30, where $Ar^3$, $R^1$, $R^2$, $R^9$-$R^{10}$ and $L^1$ are as defined above. Conversion of AE in formula 30 to the aldehyde 30a can be achieved by any number of methods dependent on the form of AE as described previously. Condensation of the aldehyde group in compound 30a with a compound of formula $R^bCH_2EWG$, where $R^b$ and EWG are as defined above, under standard condensation reaction conditions such as using a base such as piperidine and the like, in the presence or absence of acetic acid and the like in solvents such as ethanol and the like at temperatures ranging from room temperature to reflux then provides a compound of Formula (I) where $E^2$ is CH=C($R^b$)(EWG). Compounds of formula $R^bCH_2EWG$ are either commercially available or they can be prepared by methods well known in the art. For example, 2-cyano-N,N-dimethylacetamide and 2-trifluoromethyl-N,N-dimethylacetamide are commercially available.

Method (h):

Alternatively, an $E^2$ precursor bearing a protected hydroxyl derivative of formula 31 can be used in lieu of compound of formula 29, to provide compounds of formula 32. Protecting groups consist of such groups as t-butyldimethylsilyl and THP and can be removed under standard deprotection conditions such as acetic acid in THF and the like at room temperature, to provide compounds of formula 33. Oxidation of the alcoholic group of compounds of formula 33 provides the corresponding aldehyde of formula 30a. The oxidation reaction can be carried out with oxalyl chloride, DMSO followed by triethyl amine at temperatures ranging from −78° C. to room temperature in solvents such as dichloromethane and the like (Swern oxidation conditions) or by Dess-Martin periodinane (DMP) and the like. Compound 30 can be converted to a compound of Formula (I) where $E^2$ is —CH=C($R^b$)(EWG) as described in Method (a) above.

Alternatively, aldehyde of formula 30a can be condensed with 2,4-thiazolidenedione in the presence of ammonium acetate and acetic acid at temperatures ranging from room temperature to 120° C. to yield compounds of formula (I) where E is a group of formula (c) as defined above.

Alternatively, the hydroxyl group in the compound of formula 33 can be converted into a leaving group (LG) such as halo, tosylate, mesylate or triflate, and the like to provide a compound of formula 34 by methods well known in the art. For example, a compound of formula 34 where the leaving group is tosylate or mesylate can be prepared by reacting a compound of formula 33 with toluenesulfonyl chloride or methanesulfonyl chloride respectively in the presence of a base such as pyridine, and the like and in an organic solvent such as dichloromethane, and the like, at temperatures from −20° C. to reflux. Alkylation of compounds of formula 34 with 2,4-thiazolidenedione in the presence of a base such as sodium hydride or potassium tert-butoxide, and the like in an organic solvent such as toluene or dimethylformamide, THF, and the like, at temperatures from 0° C. to 10° C. provides a compound of formula 35. Condensation of compound 35 with an aldehyde of formula $R^cCHO$, such as cyclopropyl aldehyde or t-butyl aldehyde, and the like in an organic solvent such as ethanol and at temperatures ranging from 0° C. to reflux yield compounds of Formula (I) where $E^2$ is a group of formula (a).

Method (i)

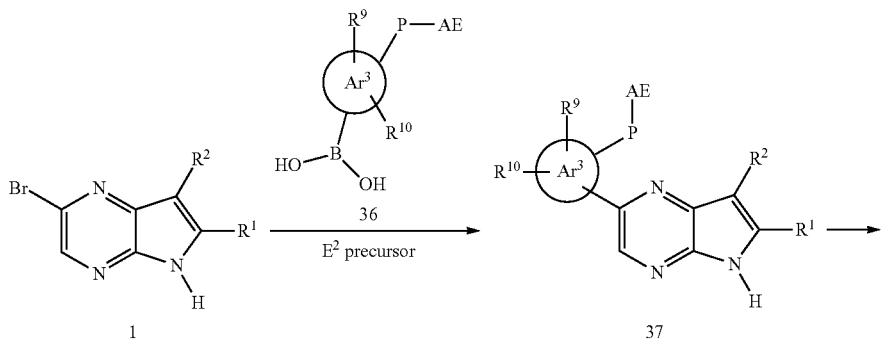

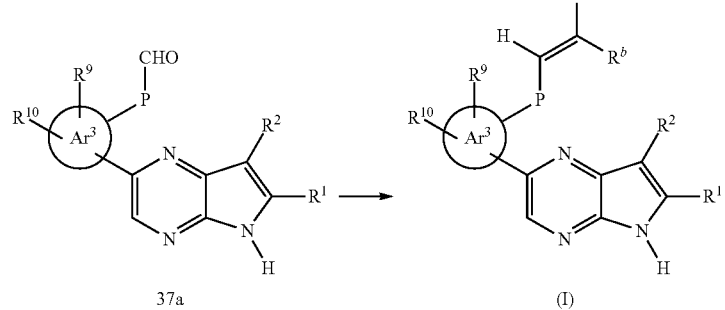

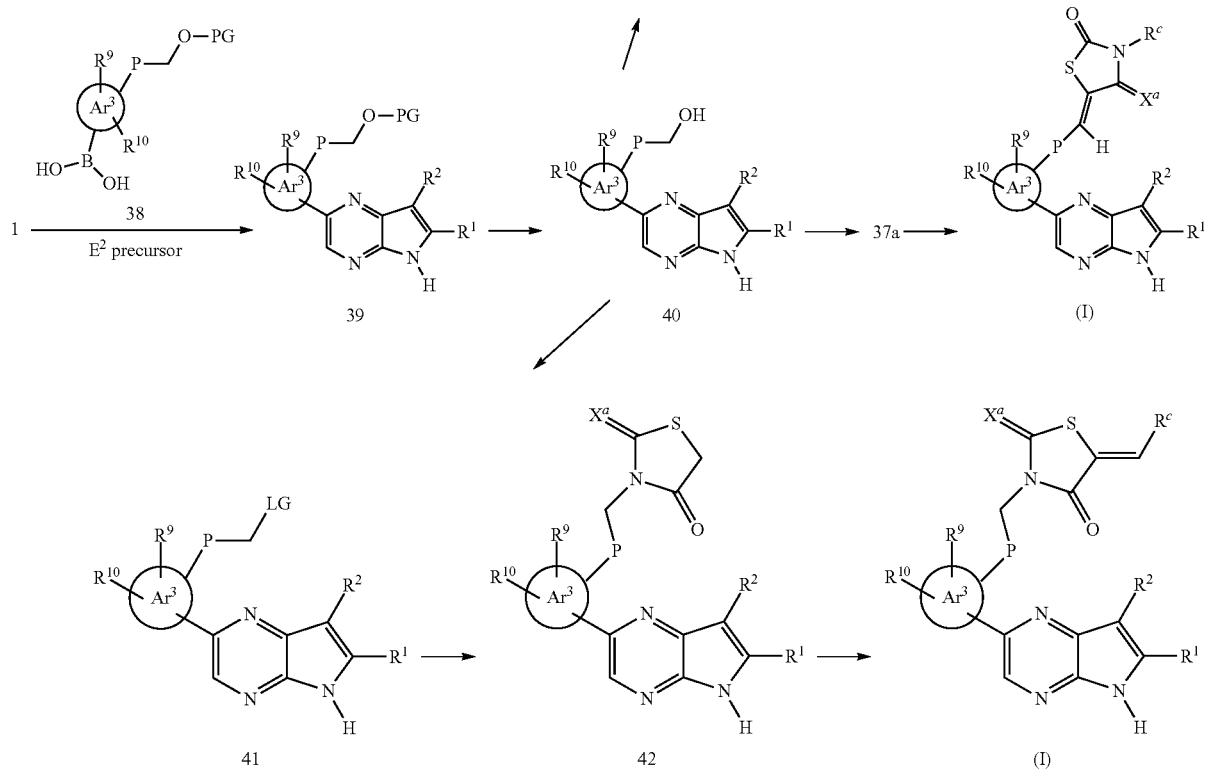

Method (i):

In a more general example of Method (g), cross coupling of a compound of formula 1 with an $E^2$ precursor compound bearing a suitable aldehyde equivalent (AE) as described in method (a), of formula 36 under Suzuki conditions as described in Scheme A, provides a compound of formula 37 where P, $Ar^3$, $R^1$, $R^2$, $R^9$-$R^{10}$ and $L^1$ are as defined above. Conversion of AE in formula 37 to the aldehyde 37a can be achieved by any number of methods dependent on the form of AE as described previously. In analogy to method (g), compounds of formula 37a can be converted to compounds of Formula (I) where $E^2$=—P—CH=C($R^b$)(EWG). The NH of pyrrolopyrimidine compounds of formula 1 can be optionally protected with protecting groups such groups as trimethylsilylethoxymethyl (SEM) or tetrahydropyranyl (THP) and the like and can be removed in the scheme above at the appropriate step under standard deprotection conditions such as acetic acid in THF or trifluoroacetic acid in methanol or with fluoride anion such as tetrabuylammonium fluoride (TBAF) in dichloromethane and the like at room temperature, to provide compounds of formula (I).

Method (j):

In a more general example of Method (h), an $E^2$ precursor bearing a hydroxyl protected derivative 38 can be used in lieu of compound of formula 36, to provide compounds of formula 39. In analogy to Method (h), compounds of formula 39 can be converted to compounds of Formula (I) where $E^2$=—P—CH=C($R^b$)(EWG) and compounds of Formula (I) where $E^2$ is a group of formula (a) and formula (b) as defined above.

Synthesis of compounds of Formula (I) when precursors to $E^2$ is Z'-(EWG')-C($R^b$)=CHR$^c$ where Z' and EWG' are as defined above is illustrated and described below as methods (e) and (f), using preparation of $E^2$ as an example.

Method (k)

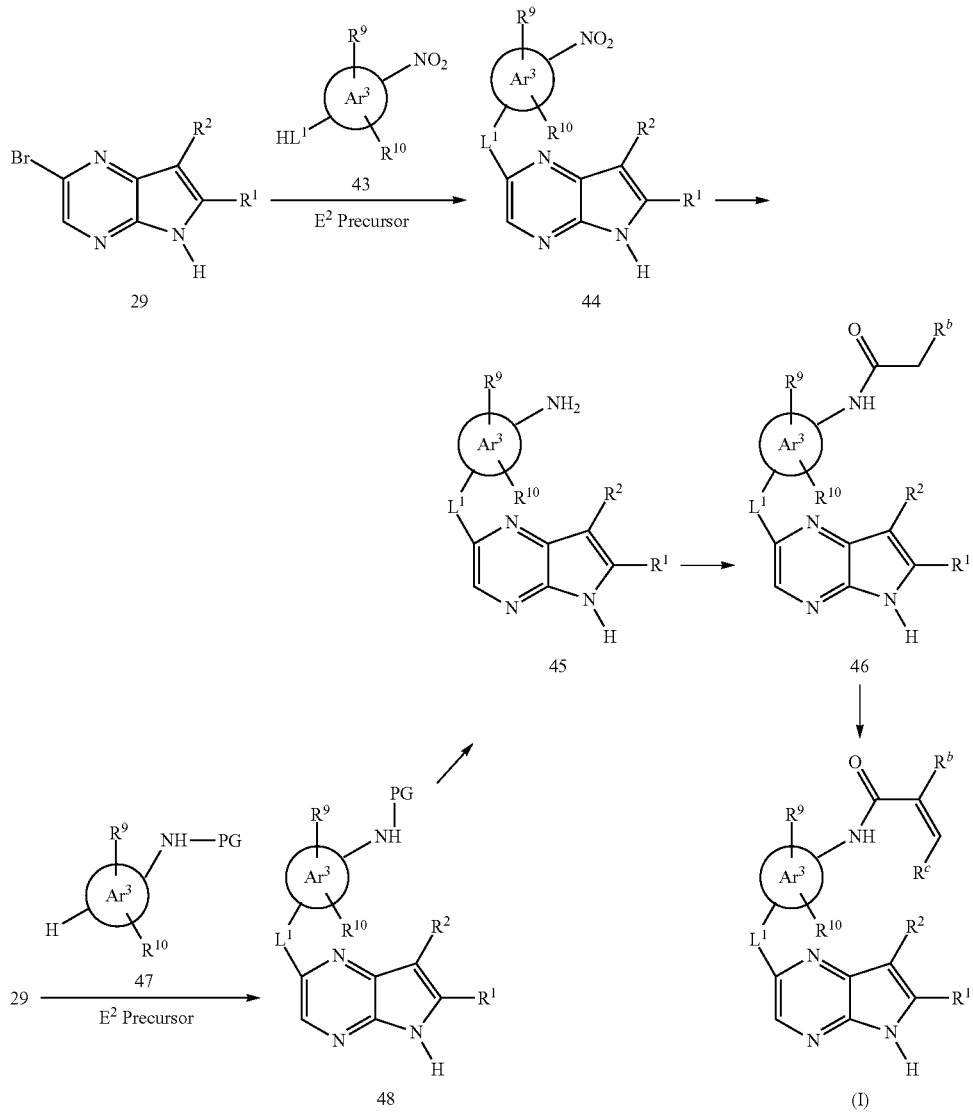

Method (k)

Coupling of a compound of formula 29 with an $E^2$ precursor compound of formula 43 bearing a nitro group with 29 under the various nucleophilic aromatic substitution conditions, or copper catalyzed, or palladium catalyzed conditions including Suzuki conditions as described in Scheme B, provides compounds of formula 44 where $Ar^3$, $R^1$, $R^2$, $R^9$-$R^{10}$ and $L^1$ are as defined above. Reduction of nitro substituent of compound 44 may be accomplished by treatment with a reducing agent such as zinc in a suitable solvent such as acetic acid and the like, or with catalytic palladium on charcoal under a hydrogen atmosphere in suitable solvents such as methanol, ethanol and the like to provide a compound of formula 45. Coupling of compounds of formula 45 with a compound of formula $R^bCH_2CO_2H$ such as 2-cyanoacetic acid or 2-trifluoromethylacetic acid, under standard amide coupling conditions such as carbon diimidazole (CDI) and the like or an acid derivative thereof provides a compound of formula 46. Subsequent condensation of a compound of formula 46 with aldehydes of formula $R^cCHO$ where $R^c$ is as defined above e.g., t-butyl or cyclopropyl aldehyde, in an organic solvent such as ethanol and the like in the presence of bases such as piperadine and the like at temperatures ranging from 0° C. to reflux provides a compound of Formula (I). It will recognized by a person of ordinary skill in the art that the EWG' moiety can be assembled at multiple points throughout the synthetic scheme and standard protecting group (PG) strategies can be employed as required.

Alternatively, coupling of a compound of formula 29 with an $E^2$ precursor compound of formula 47, containing a protected amine (Suitable nitrogen protecting groups (PG) include t-butyloxycarbonyl (BOC), carbobenzyloxy (Cbz), or 2-trimethylsilyl-ethoxymethyl (SEM)), under any of the various coupling conditions as described in Scheme B, provides a compound of formula 48. Removal of the amino protecting group under standard conditions such as HCl in ethyl acetate or trifluoroacetic acid in dichloromethane at 0° C. to room temperature for BOC and catalytic hydrogenation in ethyl alcohol for CBZ, provides a compound of formula 45, which can be carried onto compounds of Formula (I) as described above.

Method (l)

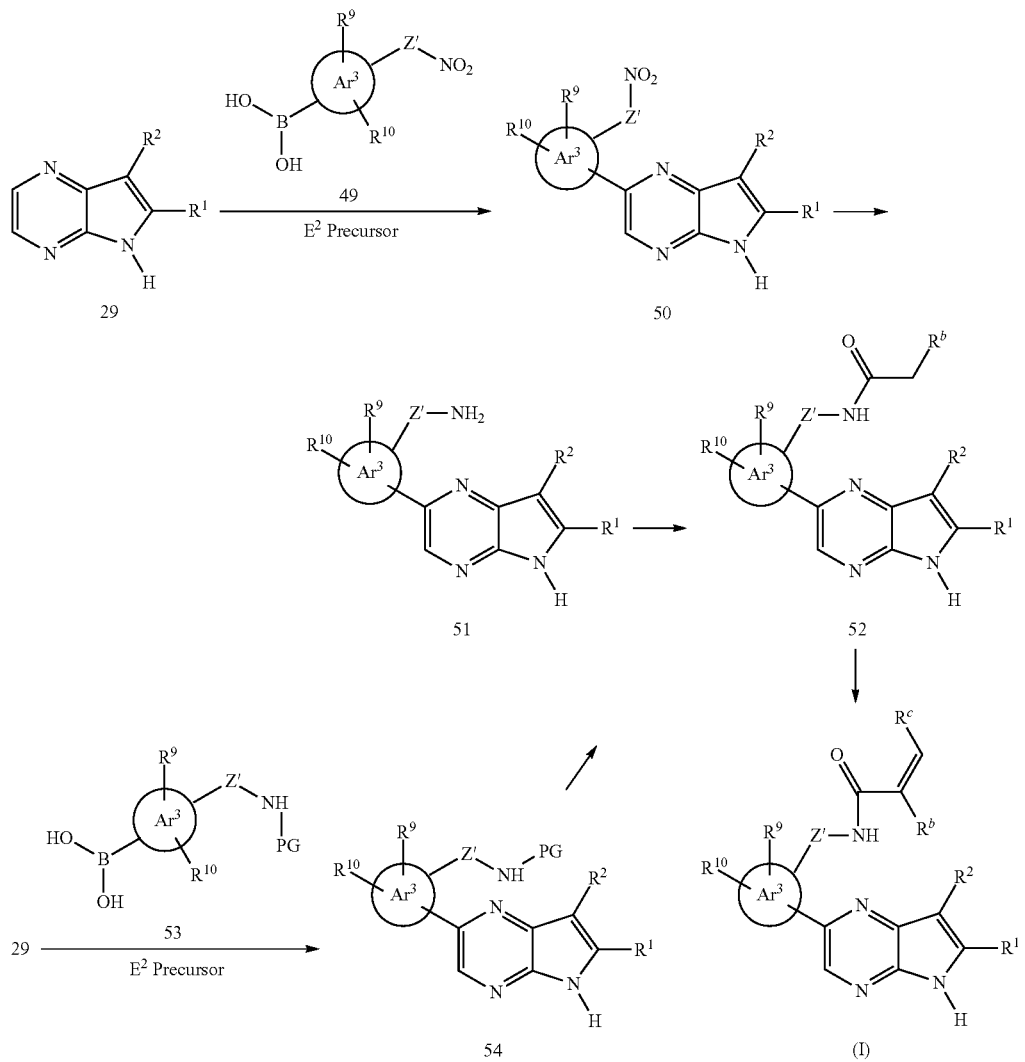

Method (l)

In a more general example of Method (k), cross coupling of a compound of formula 29 with an E² precursor compound of formula 49 under Suzuki conditions as described in Scheme B, provides a compound of formula 50 where $Ar^3$, $R^1$, $R^2$, $R^9$-$R^{10}$ and Z are as defined above. In analogy to Method (k), compounds of formula 50 can be converted to compounds of Formula (I) where $E^2$ is Z'-(EWG')-C($R^b$)=CH$R^c$ and $R^b$, $R^c$ and EWG' are as defined above.

Alternatively, an $E^2$ precursor compound bearing a protected amine derivative of formula 53 containing a protected amine (Suitable nitrogen protecting groups (PG) include t-butyloxycarbonyl (BOC), carbobenzyloxy (Cbz), or 2-tri-methylsilyl-ethoxymethyl (SEM)), can be used in lieu of compound of formula 49, providing a compound of formula 54 where $Ar^3$, $R^1$, $R^2$, $R^9$-$R^{10}$ and Z are as defined above. Removal of the amino protecting group of compounds of formula 54 as described previously provides a compound of formula 51, which can be carried onto compounds of Formula (1) as described above.

Compounds of Formula (I) where $Ar^2$, $R^1$, $R^3$, $R^7$, $R^8$ and $E^1$ are as defined above can be prepared as described in Scheme B below.

Scheme C

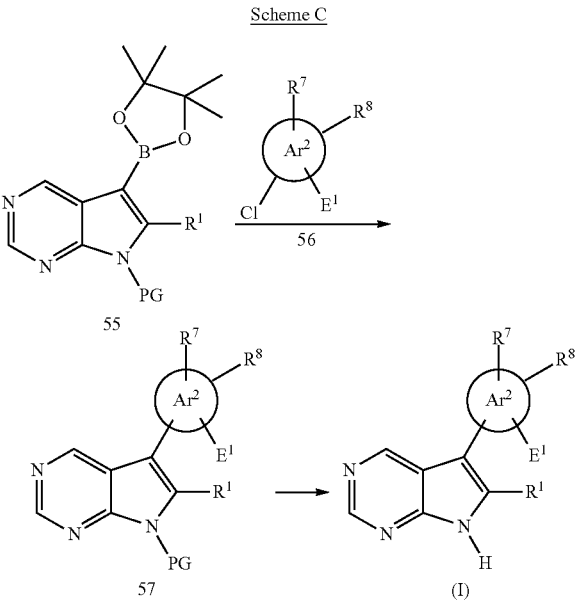

The synthesis of compounds of Formula (I) where $Ar^2$, $R^1$ is H, $R^7$, $R^8$ and $E^1$ are as defined above is outlined in Scheme C. The nitrogen at the 7 position of compounds of formula 55 can be protected with suitable groups such as toluenesulfonyl (Ts), 2,4-dinitrobenzenesulfonyl (Ns), triethylsilylethoxymethyl (SEM) and the like. The coupling of commercially available 7-tosyl-7H-pyrrolo[2,3-d]pyrimidine-5-boronic acid pinacol ester under Suzuki coupling reaction conditions as described in Scheme A provides a compound of Formula 57. The Suzuki coupling reactions can also be carried out under standard microwave conditions. Compounds of formula 56, including boronic acids and boronate esters of formula 55, are either commercially available or can be readily prepared by methods well known in the art. Removal of the tosyl protecting group of compound 57 under standard conditions including sodium methoxide in methanol or aqueous lithium hydroxide at temperatures ranging from room temperature to reflux generate compounds of Formula (I).

It will be recognized by a person skilled in the art that precursors to group $E^2$ can be substituted at any step in the synthetic procedure illustrated in Scheme C above and converted to the $E^1$ group as defined above at alternate stages in the synthetic process based on feasibility of the transformations. Some such examples are described below:

Synthesis of compounds of Formula (I) when $E^1$ is —P-Q-CH=C($R^b$)(EWG) or a group of formula (c) and (d) are illustrated and described below in Methods (m)-(n).

Method (m)

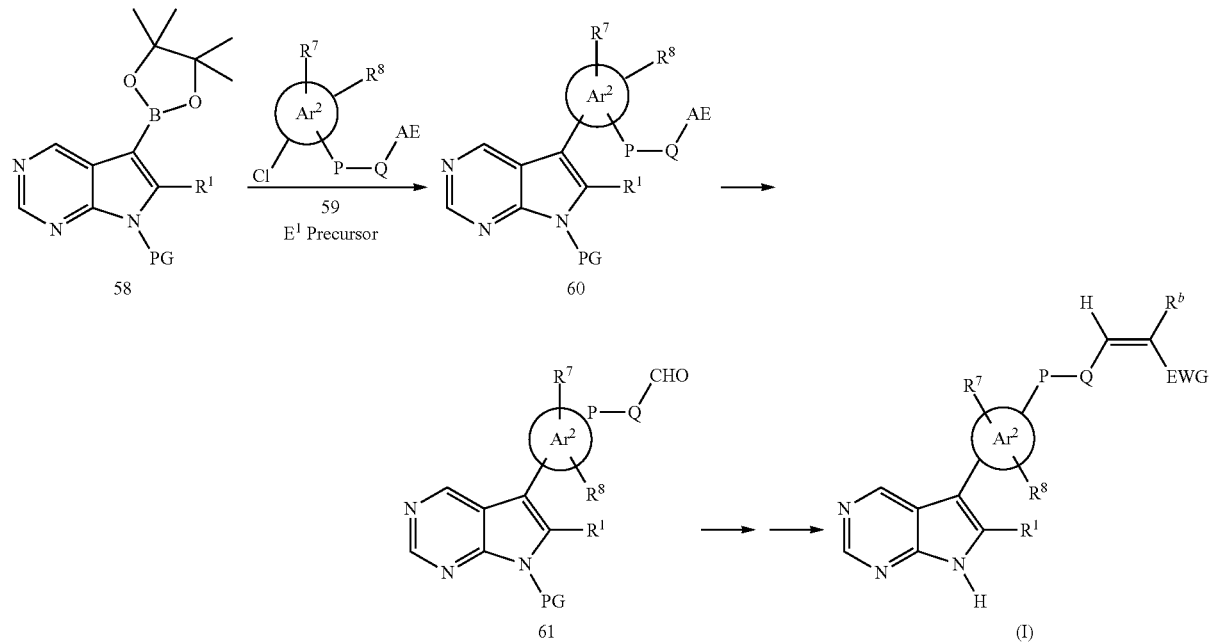

Method (n)

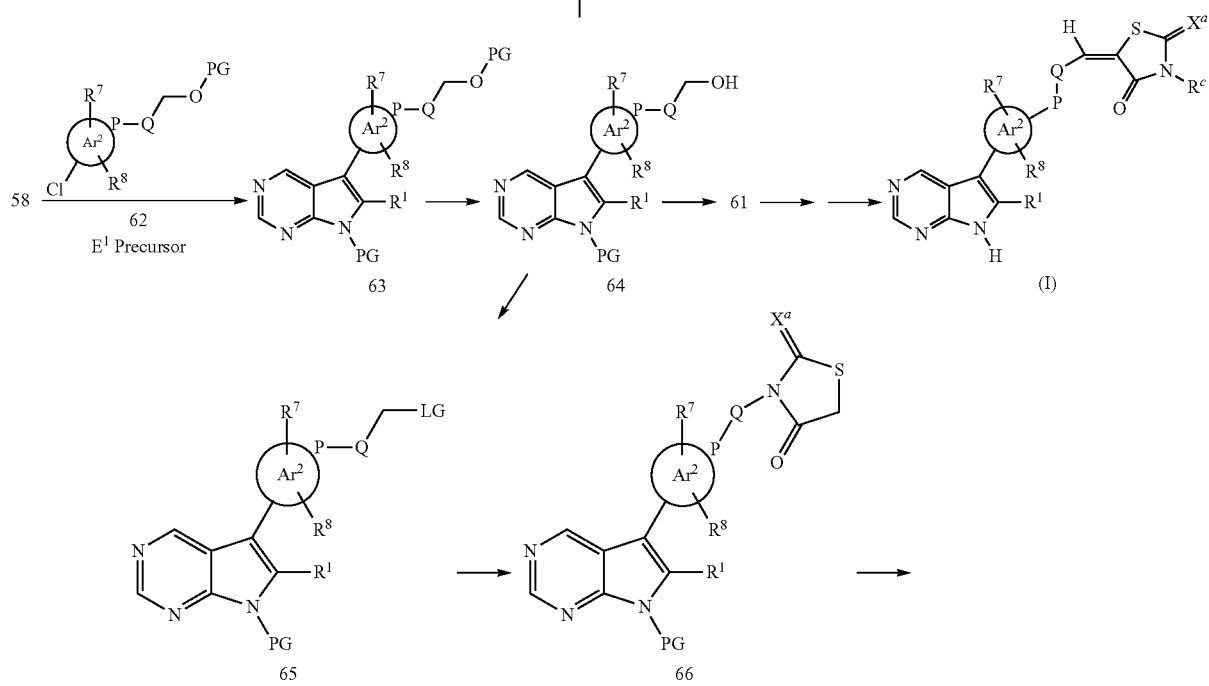

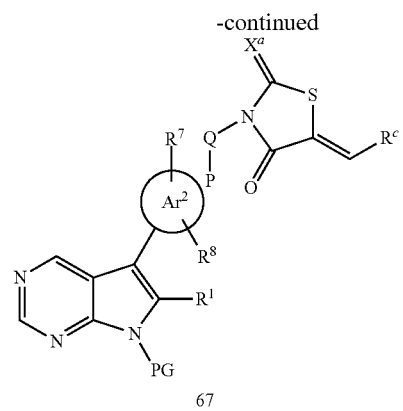

67

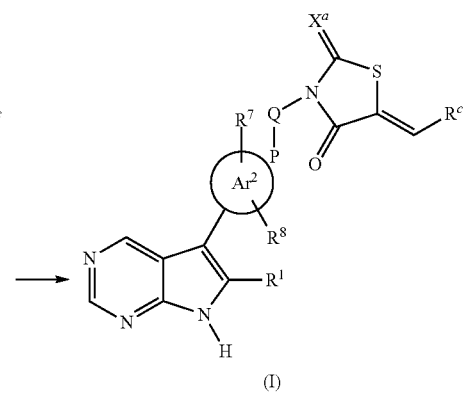

(I)

Method (m):

The coupling of a compound of formula 58 with a suitable nitrogen protecting group (PG), such as toluenesulfonyl as described in Scheme C with an $E^1$ precursor of formula 59 bearing a suitable aldehyde equivalent (AE) as described in method (a) under the Suzuki conditions as described in Scheme B, provides a compound of formula 60, where $Ar^2$, $R^b$, $R^c$, $R^7$-$R^8$, P and Q are as defined above. Conversion of AE in formula 60 to the aldehyde 61 can be achieved by any number of methods dependent on the form of AE as described previously. Condensation of the aldehyde group in compound 61 with a compound of formula $R^bCH_2EWG$, where $R^b$ and EWG are as defined above, under standard condensation reaction conditions such as using a base such as piperidine and the like, in the presence or absence of acetic acid and the like in solvents such as ethanol and the like at temperatures ranging from room temperature to reflux followed by removal of the protecting group of compound 57 under appropriate conditions including sodium methoxide in methanol or aqueous lithium hydroxide (for tosyl) or acetic acid in THF (for THP) or trifluoroacetic acid in methanol (for Boc) or with fluoride anion (for SEM) such as tetrabuylammonium fluoride (TBAF) in dichloromethane and the like at temperatures ranging from room temperature to reflux then provides a compound of Formula (I). Compounds of formula $R^bCH_2EWG$ are either commercially available or they can be prepared by methods well known in the art. For example, 2-cyano-N,N-dimethylacetamide and 2-trifluoromethyl-N,N-dimethylacetamide are commercially available.

Method (n):

In a more general example of Method (m), an $E^1$ precursor bearing a hydroxyl protected derivative 62 can be used in lieu of compound of formula 59, to provide compounds of formula 63. In analogy to Method (h), compounds of formula 63 can be converted to compounds of Formula (I) where $E^1$= P-Q-CH=C($R^b$)(EWG) and compounds of Formula (I) where $E^1$ is a group of formula (c) and formula (d) as defined above.

Method (o):

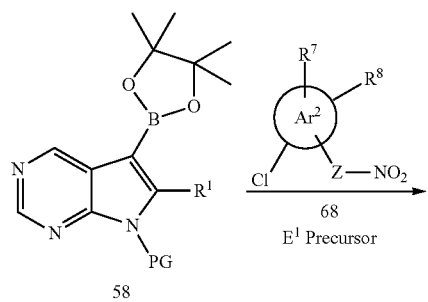

58

-continued

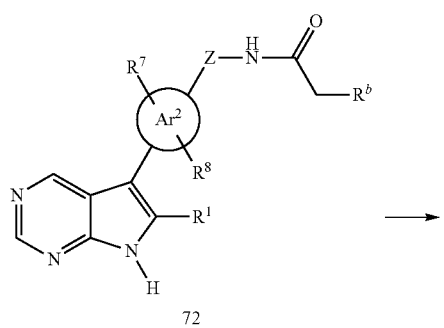

69

70

71

72

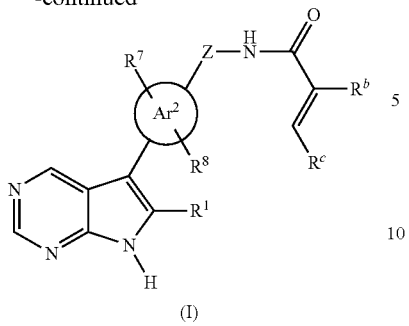

Method (o):

Coupling of a compound of formula 58 bearing a suitable nitrogen protecting group (PG), such as toluenesulfonyl as described in Scheme C with an $E^1$ precursor of formula 68 bearing a nitro group under the Suzuki conditions as described in Scheme B, provides a compound of formula 69, where $Ar^2$, $R^7$-$R^8$, and Z are as defined above. Reduction of nitro substituent of compound 69 may be accomplished by treatment with a reducing agent such as zinc in a suitable solvent such as acetic acid and the like, or with catalytic palladium on charcoal under a hydrogen atmosphere in suitable solvents such as methanol, ethanol and the like to provide a compound of formula 70. Reaction of compounds of formula 70 with a compound of formula $R^bCH_2CO_2H$ such as 2-cyanoacetic acid or 2-trifluoromethylacetic acid, under standard amide coupling conditions such as carbon diimidazole (CDI) and the like or an acid derivative thereof provides a compound of formula 71. Removal of the tosyl protecting group of compound 71 under appropriate conditions including sodium methoxide in methanol or aqueous lithium hydroxide (for tosyl) or acetic acid in THF (for THP) or trifluoroacetic acid in methanol (for Boc) or with fluoride anion (for SEM) such as tetrabuylammonium fluoride (TBAF) in dichloromethane and the like at temperatures ranging from room temperature to reflux generate compounds of formula 72.

Subsequent condensation of a compound of formula 72 with aldehydes of formula $R^cCHO$ where $R^c$ is as defined above e.g., t-butyl or cyclopropyl aldehyde, in an organic solvent such as ethanol and the like in the presence of bases such as piperadine and the like at temperatures ranging from 0° C. to reflux provides a compound of Formula (I). It will recognized by a person of ordinary skill in the art that the EWG' moiety can be assembled at multiple points throughout the synthetic scheme and standard protecting group (PG) strategies can be employed as required.

Method (p):

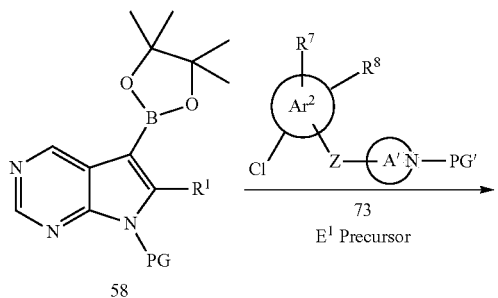

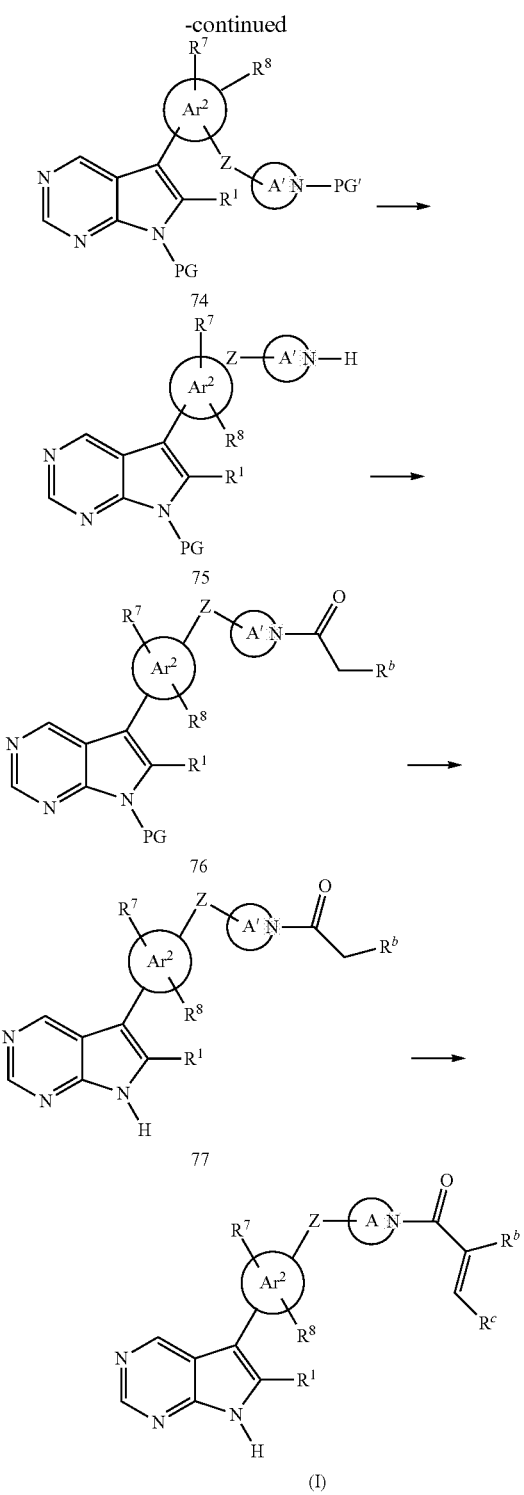

Method P:

Coupling of a compound of formula 58 bearing a suitable nitrogen protecting group (PG), such as toluenesulfonyl as described in Scheme C with an $E^1$ precursor of formula 73 where A' is heterocycloamino bearing a differentiated nitrogen protecting group PG', such as t-butylcarbonate (boc) under the Suzuki conditions as described in Scheme B, provides a compound of formula 74, where $Ar^2$, $R^7$-$R^8$, and Z are as defined above. Removal of the nitrogen protecting group PG' of compound 74, such as Boc, may be accomplished by treatment with trifluoroacetic acid and the like, in dichloromethane at 0° C. to reflux to generate a compound of formula 75. Coupling of compounds of formula 75 with a compound of formula $R^bCH_2CO_2H$ such as 2-cyanoacetic acid or 2-trifluoromethylacetic acid, under standard amide coupling conditions such as carbon diimidazole (CDI) and the like or an acid derivative thereof provides a compound of formula 76. Removal of the nitrogen protecting group (PG), such as the tosyl protecting group, of compound 76 under appropriate conditions including sodium methoxide in methanol or aqueous lithium hydroxide (for tosyl) or with fluoride anion (for SEM) such as tetrabuylammonium fluoride (TBAF) in dichloromethane and the like at temperatures ranging from room temperature to reflux generate compounds of formula 77. Subsequent condensation of a compound of formula 77 with aldehydes of formula $R^cCHO$ where $R^c$ is as defined above e.g., t-butyl or cyclopropyl aldehyde, in an organic solvent such as ethanol and the like in the presence of bases such as piperadine and the like at temperatures ranging from 0° C. to reflux provides a compound of Formula (I). It will recognized by a person of ordinary skill in the art that the EWG' moiety can be assembled at multiple points throughout the synthetic scheme and standard protecting group (PG) strategies can be employed as required.

Utility

The compounds of Formula (I) are tyrosine kinase inhibitors, in particular Jak3, and hence are useful in the treatment of autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. Preferably, the disease is rheumatoid arthritis. Preferably, the autoimmune disease is lupus.

The compounds of this Disclosure are also useful in the treatment of heteroimmune condition or disease, e.g., graft versus host disease, transplantation, transfusion, anaphylaxis, allergy, type I hypersensitivity, allergic conjunctivitis, allergic rhinitis, or atopic dermatitis.

The compounds of this Disclosure are also useful in the treatment of an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis. The compounds of this Disclosure are also useful in the treatment of dermatitis, contact dermatitis, eczema, urticaria, rosacea, and scarring psoriatic lesions in the skin, joints, or other tissues or organs.

Testing

The kinase inhibitory activity of the compounds of the present disclosure can be tested using the in vitro and in vivo assays described in Biological Examples 1-4 below.

Administration and Pharmaceutical Composition

In general, the compounds of this disclosure will be administered in a therapeutically effective amount by any of the accepted modes of administration for agents that serve similar utilities. Therapeutically effective amounts of compounds of Formula (I) may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the subject, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aid administration, and do not adversely affect therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore, contemporaneously or sequentially with a compound of the present disclosure. When a compound of the present disclosure is used contemporaneously with one or more other drugs, a pharmaceutical composition containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the subject is suffering from or at risk of suffering from an autoimmune disease, an inflammatory disease, or an allergy disease, a compound of Formula (I) can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α. binding proteins (e.g., infliximab, etanercept, or adalimumab), abatacept, anakinra, interferon-β., interferon-γ., interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subject can be treated with a compound of Formula (I) in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxy-cytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of Formula (I) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula (I) include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-la; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (I) include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula (I) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula (I) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula (I) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula (I) include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a compound of Formula (I) in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

EXAMPLES

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof. The ⌇ line in the compounds below denotes that compounds is isolated as an undefined mixture of (E) and (Z) isomers.

Reference A

Synthesis of 2-bromo-5H-pyrrolo[2,3-b]pyrazine

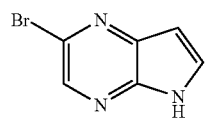

Step 1
To a 500 ml three necked round bottom flask, 3,5-dibromopyrazine-2-amine (25.0 g, 0.0988 mole) was taken in acetonitrile (250 ml). The reaction mixture was cooled to 0° C. and triethylamine (50.0 g, 0.4941 mole), copper (1) iodide (2.26 g, 0.0119 mole), and Pd(PPh$_3$)$_4$ (5.7 g, 0.0049 mole) were added under nitrogen atmosphere. The reaction mixture was stirred for 10 min at 0° C. followed by slow addition of trimethylsilylacetylene (10.7 g, 0.1089 mole) over 15 min at the same temperature. After completion of the addition, the reaction mixture was warmed up to RT and stirred for 90 min. The completion of the reaction was monitored on TLC using hexanes:ethyl acetate (5:5) as a mobile phase. After completion of the reaction, the reaction mixture was diluted by ethyl acetate and filtered through high flow. Filtrate was collected and washed with water. Layers were separated and aq. layer was re-extracted by ethyl acetate. Combined organic layer was dried over Na$_2$SO$_4$, filtered and concentrated to afford crude product which was subjected for the column purification. The crude compound was purified using column purification by eluting the compound with 7-10% ethyl acetate in hexanes to yield 20.0 g of 5-bromo-3-((trimethylsilyl)ethynyl)pyrazine-2-amine.

Step 2
To a 250 ml three necked round bottom flask, potassium tert-butoxide (4.2 g, 0.037 mole) was taken in THF (50 ml). To this, 5-bromo-3-((trimethylsilyl)ethynyl)pyrazine-2-amine (10.0 g, 0.037 mole) in THF (50 ml) was added dropwise at RT over 20 min under nitrogen atmosphere and the reaction mixture was stirred for 30 min at same temperature and 60 min at 65° C. The completion of the reaction was monitored by TLC using hexanes:ethyl acetate (8:2) as a mobile phase. After completion of the reaction, the reaction mixture was cooled to RT and diluted with ethyl acetate, filtered through high flow. Filtrate was collected and washed with water. The layers were separated and the aq. layer was re-extracted with ethyl acetate. The combined organic layer was dried over Na$_2$SO$_4$, filtered, and concentrated to afford crude product which was subjected for the column purification. The crude compound was purified using column purification by eluting the compound with 15-20% ethyl acetate in hexanes to yield 4.3 g of 2-bromo-5H-pyrrolo[2,3-b]pyrazine.

Reference B

Synthesis of 4-(7-pivaloyl-5-((2-(trimethylsilyl)ethoxy)methyl)-5H-pyrrolo[2,3-b]pyrazine-2-ylamino)benzaldehyde

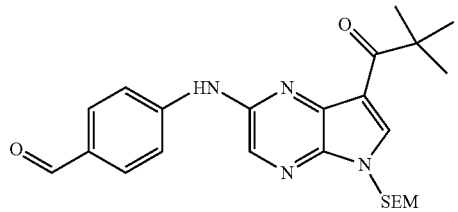 [SMILES: CC(C)(C)C(=O)c1cn(COCC[Si](C)(C)C)c2ncc(Nc3ccc(C=O)cc3)nc12]

Step 1
To a 500 ml three necked round bottom flask, 2-bromo-5H-pyrrolo[2,3-b]pyrazine (5.0 g, 0.0252 mole) was taken in CH$_2$Cl$_2$ (150 ml). The reaction mixture was cooled to 0° C. and diethylaluminiumchloride (1M solution in hexanes) (9.11 g, 0.0756 mole) was added drop wise at the same temperature under nitrogen atmosphere. The reaction mixture was stirred for 30 min at 0° C. followed by slow addition of pivoloyl chloride (29.45 g, 0.2444 mole) over 15 min at the same temperature. After completion of the addition, the reaction mixture was warmed up to RT and then up to 40° C. and stirred for 16 hrs. The completion of the reaction was monitored on TLC using hexanes:ethyl acetate (5:5) as a mobile phase. After completion of the reaction, the reaction mixture was poured in saturated NaHCO$_3$ solution with stirring at 10°

C., diluted with CH$_2$Cl$_2$ and filtered through high flow. The filtrate was collected and washed with brine solution. Layers were separated and the aq. Layer was extracted with CH$_2$Cl$_2$. The combined organic layer was dried over Na$_2$SO$_4$, filtered and concentrated to afford crude product which was subjected for the column purification. The crude compound was purified using column purification by eluting the compound with 10-25% ethyl acetate in hexanes to yield 5.3 g of 1-(2-bromo-5H-pyrrolo[2,3-b]pyrazine-7-yl)-2,2-dimethyl propan-1-one.

Step 2

To a 100 ml three necked round bottom flask, sodium hydride (60% in paraffin) (0.744 g, 0.0186 mole) was taken in DMF (10.0 ml). To this, 1-(2-bromo-5H-pyrrolo[2,3-b]pyrazine-7-yl)-2,2-dimethyl propan-1-one (5.0 g, 0.1773 mole) in DMF (15 ml) was slowly added at 0° C. over 15 min under nitrogen atmosphere. After addition was complete, the reaction mixture was stirred for 10 min at same temperature followed by dropwise addition of SEM chloride (3.1 g, 0.0186 mole) at 0° C. After completion of the addition, the reaction mixture was warmed up to RT and stirred for 30 min. After completion of the reaction, the reaction mixture was poured in water and the aq. Layer was extracted with ethyl acetate. Organic layers were combined, washed with brine solution, dried over Na$_2$SO$_4$, filtered and concentrated to afford crude product which was subjected for the column purification. The crude compound was purified using column purification by eluting the compound with 10-15% ethyl acetate in hexanes to yield 7.0 g of 1-(2-bromo-5-((2-(trimethylsilyl)ethoxy)methyl)-5H-pyrrolo[2,3-b]pyrazine-7-yl)-2,2-dimethylpropane-1-one.

Step 3

To a 35 ml sealed tube, 1-(2-bromo-5-((2-(trimethylsilyl)ethoxy)methyl)-5H-pyrrolo[2,3-b]pyrazine-7-yl)-2,2-dimethylpropane-1-one (2.0 g, 0.0048 mole) and (4-aminophenyl)methanol (0.78 g, 0.0063 mole) was taken in toluene (20.0 ml). The reaction mixture was purged with argon for 15 min at RT followed by Cs$_2$CO$_3$ (4.7 g, 0.0144 mole) was added and further purged for 30 min with argon. BINAP (0.06 g, 0.0001 mole) and Pd(OAc)$_2$ (0.021 g, 0.0001 mole) were added to reaction mixture and heated to 110° C. for 4 hr. After completion of the reaction, the reaction mixture was filtered through celite bed and washed with ethyl acetate. Filtrate was collected and concentrated to afford crude product which was subjected for the column purification. The reaction with repeated twice and the crude product from each reaction was mixed and then purified using column purification by eluting the compound with 25-30% ethyl acetate in hexanes to yield 4.7 g of 1-(2-(4-(hydroxymethyl)phenylamino)-5-((2-(trimethylsilyl)ethoxy)methyl)-5H-pyrrolo[2,3-b]pyrazin-7-yl)-2,2-dimethylpropan-1-one.

Step 4

To a 100 ml three necked round bottom flask 1-(2-(4-(hydroxymethyl)phenylamino)-5-((2-(trimethylsilyl)ethoxy)methyl)-5H-pyrrolo[2,3-b]pyrazin-7-yl)-2,2-dimethylpropan-1-one (2.3 g, 0.0051 mole) was taken in CH$_2$Cl$_2$ (25 ml). The reaction mixture was cooled to 5° C. and PCC (4.84 g, 0.0225 mole) was added at the same temperature under nitrogen atmosphere. The reaction mixture was warmed up to RT and then stirred for 2 hr. After completion of the reaction, the reaction mixture was poured into saturated NaHCO$_3$ solution (50 ml) under stirring at 10° C. and the aq. layer was extracted with CH$_2$Cl$_2$. The combined organic layer was dried over Na$_2$SO$_4$, filtered and concentrated to afford crude product which was purified using column purification by eluting the compound with 15-20% ethyl acetate in hexanes to yield 1.7 g of 4-(7-pivaloyl-5-((2-(trimethylsilyl)ethoxy)methyl)-5H-pyrrolo[2,3-b]pyrazin-2-ylamino)benzaldehyde.

Example 1

Synthesis of 2-cyano-3-(4-(7-pivaloyl-5H-pyrrolo[2,3-b]pyrazin-2-ylamino)phenyl)acrylamide

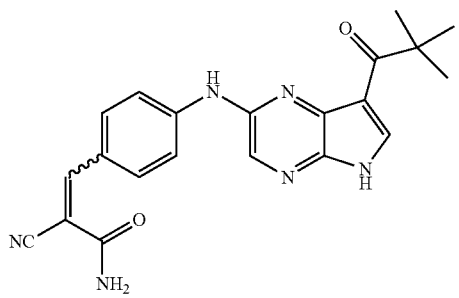 [SMILES: CC(C)(C)C(=O)c1c[nH]c2ncc(Nc3ccc(C=C(C#N)C(N)=O)cc3)nc12]

Step 1

To a 50 ml three necked round bottom flask 4-(7-pivaloyl-5-((2-(trimethylsilyl)-ethoxy)-methyl)-5H-pyrrolo[2,3-b]pyrazin-2-ylamino)benzaldehyde (0.25 g, 0.0005 mole) and 2-cyanoacetamide (0.094 g, 0.0011 mole) was taken in ethanol (20 ml). To this reaction mixture, piperidine acetate (3.3 M solution in water) (1.0 ml) was added drop wise at RT. After completion of the addition, reaction mixture was refluxed for 2 hr. After completion of the reaction, the ethanol was distilled out and water was added to residue. The aq. layer was extracted with ethyl acetate, the organic layers were combined, dried over Na$_2$SO$_4$, filtered and concentrated to afford crude product. The crude compound was purified by triturated with n-pentane, pentane layer was decanted and solid was dried under vacuum to yield 0.25 g of 2-cyano-3-(4-(7-pivaloyl-5-((2-(trimethylsilyl)ethoxy)-methyl)-5H-pyrrolo[2,3-b]pyrazin-2-ylamino)phenyl)acrylamide.

Step 2

To a 25 ml one necked round bottom flask 2-cyano-3-(4-(7-pivaloyl-5-((2-(trimethylsilyl)ethoxy)methyl)-5H-pyrrolo[2,3-b]pyrazin-2-ylamino)phenyl)acrylamide (0.1 g, 0.0002 mole) was taken in CH$_2$Cl$_2$ (10 ml). To this reaction mixture TFA (2.0 ml) was added dropwise at 0° C. After completion of the addition, the reaction mixture was warmed up to RT and then stirred for 16 hr. After completion of the reaction, CH$_2$Cl$_2$ was distilled out and the pH was adjusted to 8 to 9 using saturated NaHCO$_3$ solution at 5° C. The reaction mixture was stirred for 15 min, solid was filtered, washed with n-pentane and dried. In a 25 ml RBF, dried solid was taken in ethanol and NaOAc. 3H$_2$O (0.27 g, 0.002 mole) was added at RT. The reaction mixture was stirred for 20 hr at RT, diluted with ethyl acetate and distilled out under vacuum. To the resultant residual solid water was added, the mixture was stirred for 15 min, filtered, wash with water and n-pentane was added. The product was filtered and dried under vacuum to yield 20 mg of 2-cyano-3-(4-(7-pivaloyl-5H-pyrrolo[2,3-b]pyrazin-2-ylamino)phenyl)acrylamide.

Example 2

Synthesis of 2-cyano-N-methyl-3-(4-(7-pivaloyl-5H-pyrrolo[2,3-b]pyrazin-2-ylamino)phenyl)acrylamide

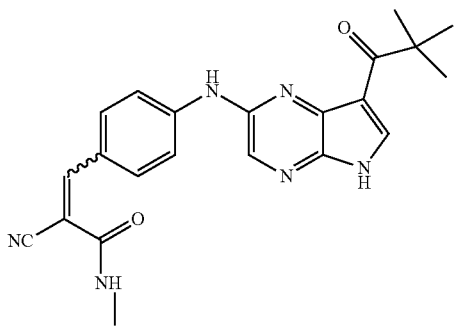 [SMILES: CNC(=O)C(C#N)=Cc1ccc(Nc2cnc3[nH]cc(C(=O)C(C)(C)C)c3n2)cc1]

To a 50 ml three necked round bottom flask, 4-(7-pivaloyl-5-((2-(trimethylsilyl)-ethoxy)methyl)-5H-pyrrolo[2,3-b]pyrazin-2-ylamino)benzaldehyde (0.25 g, 0.0005 mole) and 2-cyano-N-methylacetamide (0.22 g, 0.0022 mole) was taken in ethanol (20 ml). To this reaction mixture, piperidine acetate (1.0 ml) was added dropwise at RT. After completion of the addition, reaction mixture was refluxed for 2 hr. After completion of the reaction, ethanol was distilled out under vacuum and water was added to the residue. The aq. layer was extracted with ethyl acetate. Combined organic layer was dried over $Na_2SO_4$, filtered and concentrated to afford crude product. The crude compound was purified by triturated with n-pentane, the pentane layer was decanted and solid was dried under vacuum to yield 0.255 g of 2-cyano-N-methyl-3-(4-(7-pivaloyl-5-((2-(trimethylsilyl)methyl)methyl)-5H-pyrrolo[2,3-b]pyrazin-2-ylamino)phenyl)acrylamide which was converted to the title compound as described in Example 1, Step 2 above.

Example 3

Synthesis of 2-(azetidine-1-carbonyl)-3-(4-(7-pivaloyl-5H-pyrrolo[2,3-b]pyrazin-2-ylamino)phenyl)acrylonitrile

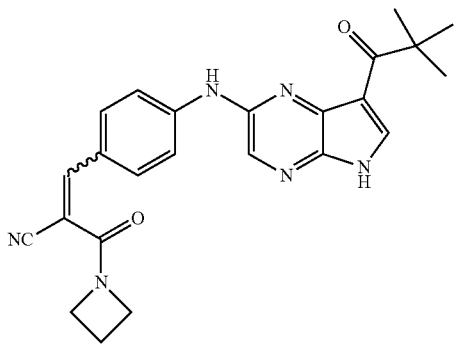 [SMILES: CC(C)(C)C(=O)c1c[nH]c2ncc(Nc3ccc(C=C(C#N)C(=O)N4CCC4)cc3)nc12]

Step 1

To a 50 ml three necked round bottom flask 4-(7-pivaloyl-5-((2-(trimethylsilyl)-ethoxy)methyl)-5H-pyrrolo[2,3-b]pyrazin-2-ylamino)benzaldehyde (0.13 g, 0.00029 mole) and 3-(azetidin-1-yl)-3-oxopropanenitrile (0.107 g, 0.00086 mole) was taken in ethanol (20 ml). To this reaction mixture, piperidine acetate (0.05 ml) was added drop wise at RT. After completion of the addition, the reaction mixture was refluxed for 2 hr. After completion of the reaction, ethanol was distilled out under vacuum and water was added to the residue. The aq. layer was extracted with ethyl acetate and the combined organic layer was dried over $Na_2SO_4$, filtered and concentrated to afford crude product. The crude compound was purified by triturated with n-pentane, pentane layer was decanted and solid was dried under vacuum to yield 0.14 g of 2-(azetidine-1-carbonyl)-3-(4-(7-pivaloyl-5-((2-(trimethylsilyl)ethoxy)-methyl)-5H-pyrrolo[2,3-b]pyrazin-2-ylamino)phenyl)acrylonitrile which was converted to the title compound as described in Example 1, Step 2.

Example 4

Synthesis of 2-(morpholine-4-carbonyl)-3-(4-(7-pivaloyl-5H-pyrrolo[2,3-b]pyrazin-2-yl amino)phenyl)acrylonitrile

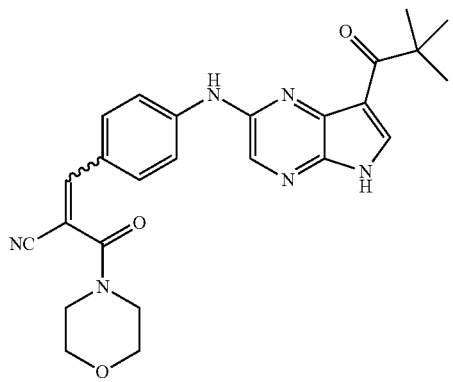

Step 1

To a 50 ml three necked round bottom flask 4-(7-pivaloyl-5-((2-(trimethylsilyl)-ethoxy)methyl)-5H-pyrrolo[2,3-b]pyrazin-2-ylamino)benzaldehyde (0.25 g, 0.00055 mole) and 3-morpholino-3-oxopropanenitrile (0.34 g, 0.0022 mole) was taken in ethanol (20 ml). To this reaction mixture, piperidine acetate (1.0 ml) was added drop wise at RT. After completion of the addition, reaction mixture was refluxed for 4 hr. After completion of the reaction, ethanol was distilled out under vacuum and water was added to the residue. The aq. layer was extracted with ethyl acetate and the combined organic layer was dried over $Na_2SO_4$, filtered and concentrated to afford crude product. The crude compound was purified using column purification by eluting the compound with 40-50% ethyl acetate in hexanes to yield 0.18 g of 2-(morpholine-4-carbonyl)-3-(4-(7-pivaloyl-5-((2-(trimethylsilyl)ethoxy)-methyl)-5H-pyrrolo[2,3-b]pyrazin-2-ylamino)phenyl)acrylonitrile which was converted to the title compound using the procedure described in Example 1, Step 2 above.

Example 5

Synthesis of 2-(4-methylpiperazine-1-carbonyl)-3-(4-(7-pivaloyl-5H-pyrrolo[2,3-d]pyrazin-2-ylamino)phenyl)acrylonitrile

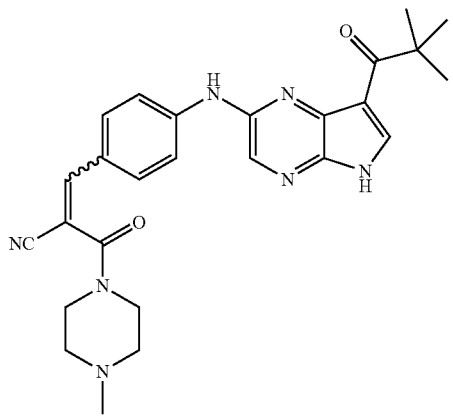

To a 35 ml reaction vial, 4-(7-pivaloyl-5-((2-(trimethylsilyl)ethoxy)methyl)-5H-pyrrolo[2,3-b]pyrazin-2-ylamino)benzaldehyde (0.200 g, 0.0004 mole) and 3-(4-methylpiperazin-3-oxopropanenitrile (0.211 g, 0.0013 mole) was taken in ethanol (10 ml). To this, piperidine acetate (3.3 M solution in water) (3 ml, 0.0099 mole) was added at RT and the reaction mixture was heated to 80° C. for 16 hr. After completion of the reaction, ethanol was evaporated under reduced pressure from the reaction mixture and then diluted with EtOAc (20 ml). The organic layer was washed with water, dried over $Na_2SO_4$ and evaporated to get product which was subjected for the column purification. The crude compound was purified using column purification using 60-120 mesh size neutral silica by eluting the compound with 2% MeOH in $CH_2Cl_2$ to yield 0.25 g of 2-(4-methylpiperazine-1-carbonyl)-3-(4-(7-pivaloyl-5-((2-(trimethylsilyl)ethoxy)methyl)-5H-pyrrolo[2,3-b]pyrazin-2-ylamino)phenyl)acrylonitrile.

Step 2

To a 35 ml vial, 2-(4-methylpiperazine-1-carbonyl)-3-(4-(7-pivaloyl-5-((2-(trimethylsilyl)ethoxy)methyl)-5H-pyrrolo[2,3-b]pyrazin-2-ylamino)phenyl)acrylonitrile (0.100 g, 0.0001 mole) was taken in $CH_2Cl_2$ (8 ml) and cooled to 0° C. under $N_2$ atm. TFA (2 ml, 0.0238 mole) was added drop wise at 0° C. and stirred for 16 h at room temperature. After completion of the reaction, the solvent was evaporated under reduced pressure from the reaction mixture and saturated $NaHCO_3$ solution was added dropwise to make pH basic. The solid which precipitated out was filtered and washed with water and pentane. The solid (0.050 g) was taken in ethanol (20 ml), $NaOAc.3H_2O$ (0.226 g, 0.0016 mole) was added and the reaction mixture and stirred at room temperature for 32 hr. Ethanol was evaporated under reduced pressure from the reaction mixture and obtained solid material was washed with water and pentane. The crude compound was purified by triturating with pentane to yield 0.017 g of 2-(4-methylpiperazine-1-carbonyl)-3-(4-(7-pivaloyl-5H-pyrrolo[2,3-b]pyrazin-2-ylamino)phenyl)acrylonitrile.

Example 6

Synthesis of 5-(4-(7-pivaloyl-5H-pyrrolo[2,3-b]pyrazin-2-ylamino)benzylidene)thiazolidine-2,4-dione

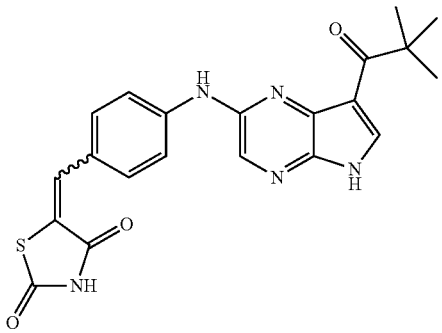

Step 1

To a 35 ml reaction vial 4-(7-pivaloyl-5-((2-(trimethylsilyl)ethoxy)methyl)-5H-pyrrolo[2,3-b]pyrazin-2-yl amino)benzaldehyde (0.200 g, 0.0004 mole) and thiazolidine-2,4-dione (0.155 g, 0.0105 mole) were taken in ethanol (10 ml). Piperidine acetate (3.3M solution in water) (3 ml) was added at RT. The reaction mixture was heated to 80° C. for 16 hrs. After completion of the reaction, ethanol was evaporated under reduced pressure and diluted with EtOAc. Organic layer was washed with water, dried over $Na_2SO_4$ and evaporated to get crude product which was purified using column purification by eluting the compound with 10-20% EtOAc in Hexanes to yield 0.170 g of 5-(4-(7-pivaloyl-5-((2-(trimethylsilyl)ethoxy)-methyl)-5H-pyrrolo[2,3-b]pyrazin-2-ylamino)benzylidene)thiazolidine-2,4-dione.

Step 2

In a 35 ml vial, 5-(4-(7-pivaloyl-5-((2-(trimethylsilyl)ethoxy)methyl)-5H-pyrrolo[2,3-b]pyrazin-2-ylamino)benzylidene)thiazolidine-2,4-dione (0.100 g, 0.0001 mole) was taken in 8 ml $CH_2Cl_2$ and cooled to 0° C. under $N_2$ atm. TFA (2 ml, 0.0268 mole) was added dropwise at 0° C. and the reaction mixture was stirred for 16 h at room temperature. After completion of the reaction, solvent was evaporated under reduced pressure from the reaction mixture and saturated $NaHCO_3$ solution was added dropwise to make Ph basic. The solid that precipitated out was washed with water and pentane and 0.050 g of the solid was taken up in ethanol (20 ml) and $NaOAc.3H_2O$ (0.246 g, 0.0018 mole) was added. The reaction mixture was stirred at room temperature for 16 hr. Ethanol was evaporated under reduced pressure and the solid was washed with water and pentane. The crude compound was purified by triturating with pentane to yield 0.018 g of the title compound.

Example 7

Synthesis of 2-cyano-3-(2-fluoro-4-(7-pivaloyl-5H-pyrrolo[2,3-b]pyrazin-2-ylamino)phenyl)-N,N-dimethylacrylamide

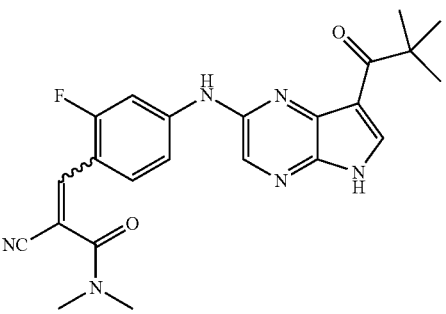

Step 1

To a 250 ml three necked round bottom flask, methyl 4-amino-2-fluorobenzoate (2.75 g, 0.0162 mole) was added in anhydrous THF (60 ml) under nitrogen atmosphere and cooled to 0-5° C. After 15 minutes, 2.0 M solutions of LAH in THF (24.3 ml, 0.0487 mole) was added dropwise and stirred for 10 min. The reaction mixture was allowed to warm up to room temperature and stirred at same temperature for 1 hr. After completion of the reaction, the reaction mixture was cooled to 5° C. and quenched with sat. NH$_4$Cl (25 ml) and diluted with water (100 ml) followed by extraction with ethyl acetate. The combined organics were washed with water, dried over sodium sulphate and evaporated to afford brown solid (crude) product which was purified using column purification by eluting the compound with 20% ethyl acetate in hexanes to yield 1.7 g of (4-amino-2-fluorophenyl)methanol.

Step 2

To a 35 ml seal tube was added 1-(2-bromo-5-((2-(trimethylsilyl)ethoxy)methyl)-5H-pyrrolo[2,3-b]pyrazin-7-yl)-2,2-dimethylpropan-1-one (1.00 g, 0.0024 mole), (4-amino-2-fluorophenyl)methanol (0.342 g, 0.0024 mole), Pd$_2$(dba)$_3$ (0.666 g, 0.0007 mole), Davephos (0.19 g, 0.0004 mole) in dioxane (10 ml) and purged with argon gas for 10 min. Cs$_2$CO$_3$ (2.37 g, 0.0072 mole) was added and the reaction mixture was heated at 100° C. for 2 hr. After completion of the reaction, the reaction mixture was poured in to saturated NaHCO$_3$ solution (30 ml) and extracted with CH$_2$Cl$_2$. The combined organics were washed with brine solution. The organic layer was separated and dried over sodium sulphate, concentrated to give the desired crude product which was purified using column purification by eluting the compound with 1% methanol in chloroform to yield 0.48 g of 1-(2-(3-fluoro-4-(hydroxymethyl)phenylamino)-5-((2-(trimethylsilyl)ethoxy)methyl)-5H-pyrrolo[2,3-b]pyrazin-7-yl)-2,2-dimethylpropan-1-one.

Step 3

To a 25 ml one necked round bottom flask was added Dess martin periodinane (1.29 g, 0.0030 mole) to a solution of 1-(2-(3-fluoro-4-(hydroxymethyl)phenylamino)-5-((2-(trimethylsilyl)ethoxy)methyl)-5H-pyrrolo[2,3-b]pyrazine-7-yl)-2,2-dimethylpropan-1-one (0.48 g, 0.0010 mole) in CH$_2$Cl$_2$ (10 ml) under argon atmosphere at 0° C.-5° C. and the reaction mixture was allowed to warm up to room temperature followed by stirred it at room temperature for 2 hr. After completion of the reaction, the reaction mixture was poured in to saturated NaHCO$_3$ solution and extracted with CH$_2$Cl$_2$. The combined organics were washed with brine solution. The organic layer was separated and dried over sodium sulphate, concentrated to give the desired crude product which was purified using column purification by eluting the compound with 15% ethyl acetate in hexanes to yield 0.28 g (in two lots, 0.15 g+0.13 g) of 2-fluoro-4-(7-pivaloyl-5-((2-(trimethylsilyl)ethoxy)methyl)-5H-pyrrolo[2,3-b]pyrazin-2-ylamino)benzaldehyde.

Step 4

To a 25 ml one necked round bottom flask was added 2-fluoro-4-(7-pivaloyl-5-((2-(trimethylsilyl)ethoxy)methyl)-5H-pyrrolo[2,3-b]pyrazin-2-ylamino)benzaldehyde (0.28 g, 0.000594 mole), 2-cyano-N,N-dimethyl acetamide (0.20 g, 0.001784 mole) and ethanol (10 ml) followed by addition of piperidineacetate (3.3M solution in water) (0.054 ml, 0.000178 mole) at RT & the reaction was heated at 80° C. for 4 hr. After completion of the reaction, the reaction mixture was concentrated, diluted with water and extracted with CH$_2$Cl$_2$. The combined organics were washed with water. The organic layer was separated and dried over sodium sulphate, concentrated to give the desired crude product which was purified using column purification by eluting the compound with 0.5-0.8% methanol in chloroform to yield 130 mg of 2-cyano-3-(2-fluoro-4-(7-pivaloyl-5-((2-(trimethylsilyl)ethoxy)methyl)-5H-pyrrolo[2,3-b]pyrazin-2-ylamino)-phenyl)-N,N-dimethylacrylamide.

Step 5

To a 25 ml one necked round bottom flask was added 2-cyano-3-(2-fluoro-4-(7-pivaloyl-5-((2-(trimethylsilyl)ethoxy)methyl)-5H-pyrrolo[2,3-b]pyrazin-2-ylamino)phenyl)-N,N-dimethylacrylamide (130 mg, 0.00023 mole) and CH$_2$Cl$_2$ (10 ml) followed by drop wise addition of TFA (3 ml) at 0-5° C. & the reaction was allowed to warm up to room temperature and stirred at same temperature for 4 hr. After completion of the reaction, reaction mixture was concentrated and azeotroped with toluene (20 ml). The resulting residue was dissolved in ethanol (10 ml); NaOAc.3H$_2$O (313 mg, 0.00230 mole) was added to it and stirred it at room temperature for 20 hr. The reaction mixture was diluted with water, followed by extraction with ethyl acetate. The combined organic layers were dried over sodium sulphate, concentrated to give the desired crude product which was purified using triturated with hexanes:diethyl ether (70:30) (8 ml) and resulting solid was dried to yield 79 mg of the title compound.

Proceeding as described in Example 7 above but substituting methyl 4-amino-2-fluorobenzoate with methyl4-amino-2-chlorobenzoate, 3-(2-chloro-4-(7-pivaloyl-5H-pyrrolo-[2,3-b]pyrazin-2-ylamino)phenyl)-2-cyano-N,N-dimethylacrylamide was prepared.

Proceeding as described in Example 7 above but substituting methyl 4-amino-2-fluorobenzoate with methyl 4-amino-3-fluorobenzoate, 2-cyano-3-(2-fluoro-4-(7-pivaloyl-5H-pyrrolo[2,3-b]pyrazin-2-ylamino)phenyl)-N,N-dimethylacrylamide was prepared.

Example 8

Synthesis of 2-cyano-N,N-dimethyl-3-(6-(7-pivaloyl-5H-pyrrolo[2,3-b]pyrazin-2-ylamino)pyridin-3-yl)acrylamide

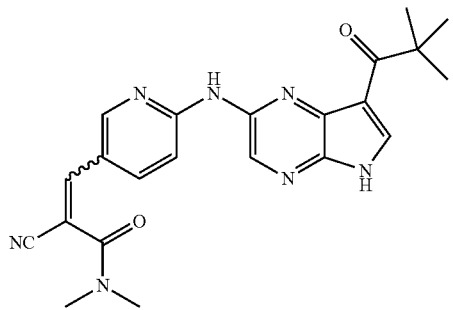

Step 1

To a 35 ml seal tube, 1-(2-bromo-5-((2-(trimethylsilyl)ethoxy)methyl)-5H-pyrrolo[2,3-b]pyrazine-7-yl)-2,2-dimethylpropane-1-one (1.0 g, 0.00242 mole) and (6-aminopyridin-3-yl)methanol (0.36 g, 0.00291 mole) was taken in toluene (10.0 ml). The reaction mixture was purged with argon for 15 min at RT followed by Cs$_2$CO$_3$ (3.1 g, 0.0097 mole) was added and further purged for 30 min with argon. BINAP (0.03 g, 0.000048 mole) and Pd(OAc)$_2$ (0.01 g, 0.000048 mole) were added and the reaction mixture was heated to 110° C. for 16 hrs. After completion of the reaction, the reaction mixture was filtered through celite bed and washed with ethyl acetate. Filtrate was collected and concentrated to afford crude product which was purified using column purification by eluting the compound with 20-25% ethyl acetate in hexanes to yield 0.5 g of 1-(2-(5-(hydroxymethyl)pyridin-2-ylamino)-5-((2-(trimethylsilyl)ethoxy)methyl)-5H-pyrrolo[2,3-b]pyrazin-7-yl)-2,2-dimethylpropan-1-one.

Step 2

To a 100 ml three necked round bottom flask 1-(2-(5-(hydroxymethyl)pyridin-2-ylamino)-5-((2-(trimethylsilyl)ethoxy)methyl)-5H-pyrrolo[2,3-b]pyrazin-7-yl)-2,2-dimethylpropan-1-one (0.5 g, 0.00109 mole) was taken in $CH_2Cl_2$ (20 ml). $MnO_2$ (1.9 g, 0.0219 mole) was added in one portion at room temperature under nitrogen atmosphere. The reaction mixture was stirred for 15 min. After completion of the reaction, the reaction mixture was filtered through celite bed and washed with $CH_2Cl_2$. The filtrate was collected and concentrated to afford crude product which was subjected for the column purification. The crude compound was purified using column purification by eluting the compound with 25-30% ethyl acetate in hexanes to yield 0.33 g of 6-(7-pivaloyl-5-((2-(trimethylsilyl)ethoxy)-methyl)-5H-pyrrolo[2,3-b]pyrazin-2-ylamino)nicotinaldehyde.

Step 3

To a 50 ml three necked round bottom flask 6-(7-pivaloyl-5-((2-(trimethylsilyl)-ethoxy)methyl)-5H-pyrrolo[2,3-b]pyrazin-2-ylamino)-nicotinaldehyde (0.33 g, 0.00072 mole) and 2-cyano-N,N-dimethylacetamide (0.245 g, 0.00218 mole) was taken in ethanol (10 ml). To this reaction mixture, piperidine acetate (3.3 M solution in water) (0.1 ml) was added drop wise at RT. After completion of the addition, reaction mixture was refluxed for 4 hrs. After completion of the reaction, the ethanol was distilled out and water was added to residue. The aqueous layer was extracted with ethyl acetate and organic layers were combined, dried over $Na_2SO_4$, filtered and concentrated to afford crude product. The crude compound was purified by triturated with n-pentane (10.0 ml), pentane layer was decanted and solid was dried under vacuum to yield 0.35 g of 2-cyano-N,N-dimethyl-3-(6-(7-pivaloyl-5-((2-(trimethylsilyl)ethoxy)methyl)-5H-pyrrolo[2,3-b]pyrazin-2-ylamino)pyridin-3-yl)acrylamide.

Step 4

To a 25 ml one necked round bottom flask 2-cyano-N,N-dimethyl-3-(6-(7-pivaloyl-5-((2-(trimethylsilyl)ethoxy)methyl)-5H-pyrrolo[2,3-b]pyrazin-2-ylamino)pyridin-3-yl)acrylamide (0.1 g, 0.000182 mole) was taken in $CH_2Cl_2$ (10 ml). To this reaction mixture TFA (2.0 ml) was added dropwise at 0° C. After completion of the addition, the reaction mixture was warmed up to RT and then stirred for 16 hrs. After completion of the reaction, $CH_2Cl_2$ was distilled out and set pH 8 to 9 using saturated $NaHCO_3$ solution (20.0 ml) at 5° C. Reaction mixture was stirred for 15 min. The solid was filtered, washed with methanol followed by n-pentane and dried under vacuum to yield 40 mg of 2-cyano-N,N-dimethyl-3-(6-(7-pivaloyl-5H-pyrrolo[2,3-b]pyrazin-2-ylamino)pyridin-3-yl)acrylamide.

Example 9

Synthesis of 2-cyano-N,N-dimethyl-3-(5-(7-pivaloyl-5H-pyrrolo[2,3-b]pyrazin-2-ylamino)pyridin-2-yl)acrylamide

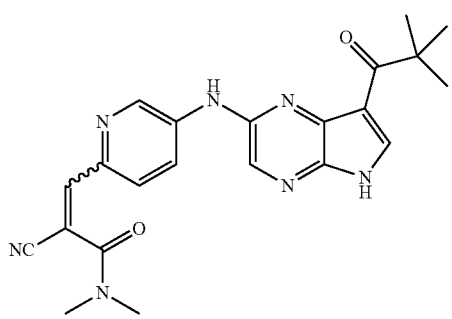

Step 1

To a 250 ml three necked round bottom flask was added methyl 5-aminopicolinate (2.0 g) in THF (40 ml) under nitrogen atmosphere and cooled to 0-5° C. After 15 min, 2.0 M solutions of $LiAlH_4$ (19.7 ml) was added under nitrogen atmosphere and allow it to warm up to room temperature and stirred at same temperature for 1 hr. After completion of the reaction, the reaction mixture was cooled to 5° C. and quenched with sat. $NH_4Cl$ solution (25 ml) and diluted with water, followed by extraction with ethyl acetate. The combined organics were washed with water, dried over $Na_2SO_4$ and evaporated to afford brown oil product. The aqueous layer was concentrated to give residue which was washed with 30% methanol in ethyl acetate. Resultant washing was concentrated to afford brown oil (crude). Both the crude material were combined and subjected for column purification using 8% methanol in chloroform to yield 1.3 g of (5-aminopyridin-2-yl)methanol.

Step 2

To a 35 ml seal tube, 1-(2-bromo-5-((2-(trimethylsilyl)ethoxy)methyl)-5H-pyrrolo[2,3-b]pyrazine-7-yl)-2,2-dimethylpropane-1-one (0.25 g, 0.000606 mole) and (5-aminopyridin-2-yl)methanol (0.09 g, 0.00728 mole) was taken in toluene (3.0 ml). The reaction mixture was purged with argon for 15 min at RT and NaOtBu (0.11 g, 0.00121 mole) was added and the reaction mixture was further purged for 30 min with argon. BINAP (0.037 g, 0.000060 mole) and $Pd_2(dba)_3$ (0.027 g, 0.000030 mole) were added and the reaction mixture was heated to 110° C. for 3 hrs. After completion of the reaction, the reaction mixture was filtered through celite bed and washed with ethyl acetate. Filtrate was collected and concentrated to afford crude product which was purified using column purification by eluting with 40-50% ethyl acetate in hexanes to yield 0.1 g of 1-(2-(6-(hydroxymethyl)pyridin-3-ylamino)-5-((2-(trimethylsilyl)ethoxy)methyl)-5H-pyrrolo[2,3-b]pyrazin-7-yl)-2,2-dimethylpropan-1-one.

Step 3

To a 100 ml three necked round bottom flask, 1-(2-(6-(hydroxymethyl)pyridin-3-ylamino)-5-((2-(trimethylsilyl)ethoxy)methyl)-5H-pyrrolo[2,3-b]pyrazin-7-yl)-2,2-dimethylpropan-1-one (0.32 g, 0.000702 mole) was taken in $CH_2Cl_2$ (20 ml) and cooled to 0° C. Dess Martin's reagent (1.11 g, 0.00245 mole) was added at 0° C. and the reaction was warmed to room temperature and stirred for 2 hrs under nitrogen atmosphere. After completion of the reaction, the reaction mixture was filtered through celite bed and washed with $CH_2Cl_2$. Filtrate was washed with water. Organic layers were combined, dried over $Na_2SO_4$, filtered and concentrated to afford crude product which was purified using column purification by eluting with 25-30% ethyl acetate in hexanes to yield 0.173 g of 5-(7-pivaloyl-5-((2-(trimethylsilyl)ethoxy)methyl)-5H-pyrrolo[2,3-b]pyrazine-2-yl-amino)-picolinaldehyde.

Step 4

In a 50 ml three necked round bottom flask, 5-(7-pivaloyl-5-((2-(trimethylsilyl)ethoxy)methyl)-5H-pyrrolo[2,3-b]pyrazin-2-ylamino)picolinaldehyde (0.17 g, 0.00037 mole) and 2-cyano-N,N-dimethylacetamide (0.084 g, 0.00075 mole) was taken in ethanol (5 ml). Piperidine acetate (3.3 M solution in water) (0.2 ml) was added dropwise at RT. After completion of the addition, reaction mixture was refluxed for 4 hrs and after completion of the reaction, the ethanol was distilled out and water was added to residue. Aqueous layer was extracted with ethyl acetate, organic layers were combined, dried over $Na_2SO_4$, filtered and concentrated to afford crude product. The crude compound was triturated with n-pentane, the pentane layer was decanted and solid was dried under vacuum to yield 0.152 g of 2-cyano-N,N-dimethyl-3-(5-(7-pivaloyl-5-((2-(trimethylsilyl)ethoxy)-methyl)-5H-pyrrolo[2,3-b]pyrazin-2-yl-amino)pyridin-2-yl)acrylamide which was converted to the title compound as described in Example 8 above.

Example 10

Synthesis of N-tert-butyl-2-(4-(2-cyano-3-(dimethylamino)-3-oxoprop-1-enyl)phenylamino)-5H-pyrrolo[2,3-b]pyrazine-7-carboxamide

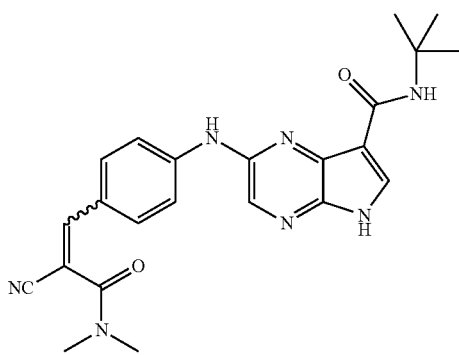

Step 1

To a reaction vial, 2-bromo-5H-pyrrolo[2,3-b]pyrazine (1 g, 0.00505 mol) was added in TFA (10 ml). Hexamine (1.06 g, 0.00757 mol) was added and reaction mixture was heated to 80° C. in microwave for 15 min. After completion of the reaction, the reaction mixture was poured into aq. Na$_2$CO$_3$ solution. Solid obtained was filtered, dried and purified using column purification by eluting with 3-5% EtOAc in Hexanes to yield 0.450 g of 2-bromo-5H-pyrrolo[2,3-b]pyrazine-7-carbaldehyde.

Step 2

To a 10 ml round bottom flask, 2-bromo-5H-pyrrolo[2,3-b]pyrazine-7-carbaldehyde (0.450 g, 0.00199 mol) and NaH (0.143 g, 0.00597 mol) were taken in DMF (5 ml) and stirred in cooling for 15 min. SEM-Cl (0.497 g, 0.00298 mol) was added dropwise and stirred at room temperature for 2 hr. After completion of the reaction, the reaction mixture was poured in to water and extracted with ethyl acetate. The combined organics were washed with brine solution. The organic layer was separated and dried over sodium sulphate, concentrated to give the crude product which was purified using column purification by eluting the compound with 10% ethyl acetate in hexanes to yield 150 mg of 2-bromo-5-((2-(trimethylsilyl)ethoxy)methyl)-5H-pyrrolo[2,3-b]pyrazine-7-carbaldehyde.

Step 3

To a 25 ml round bottom flask, 2-bromo-5-((2-(trimethylsilyl)ethoxy)methyl)-5H-pyrrolo[2,3-b]pyrazine-7-carbaldehyde (0.1 g, 0.00028 mol) and sulphamic acid (0.163 g, 0.00168 mol) were taken in dioxane (1 ml) and water (0.1 ml). A solution of NaClO$_2$ (0.032 g, 0.00036 mol) and KH$_2$PO$_4$ (0.458 g, 0.00336 mol) in water (0.9 ml) was added at 0° C. and the reaction mixture was stirred at room temperature for 2 hr. After completion of the reaction, the reaction mixture was partitioned between water and ethyl acetate. The combined organics were washed with brine solution. The organic layer was separated and dried over sodium sulphate, concentrated to give 0.07 g of 2-bromo-5-((2-(trimethylsilyl)ethoxy)-methyl)-5H-pyrrolo[2,3-b]pyrazine-7-carboxylic acid which was used as such in next step.

Step 3

To a 25 ml round bottom flask, 2-bromo-5-((2-(trimethylsilyl)ethoxy)methyl)-5H-pyrrolo[2,3-b]pyrazine-7-carboxylic acid (2.2 g, 0.00591 mol), EDC.HCl (1.35 g, 0.00709 mol), HOBt (0.958 g, 0.00709 mol), and DMAP (1.44 g, 0.0118 mol) were taken in DMF (20 ml) and stirred it for 15 min. tert-Butylamine (0.647 g, 0.00887 mol) was added dropwise and the reaction mixture was stirred at room temperature overnight. After completion of the reaction, the reaction mixture was poured into water and extracted with ethyl acetate. The combined organics were washed with brine solution. The organic layer was separated and dried over sodium sulphate, concentrated to give the desired crude product which was purified using column purification by eluting the compound with 10% ethyl acetate in hexanes to yield 2.2 g of 2-bromo-N-tert-butyl-5-((2-(trimethylsilyl)ethoxy)methyl)-5H-pyrrolo[2,3-b]pyrazine-7-carboxamide.

Step 4

To a 10 ml seal tube, 2-bromo-N-tert-butyl-5-((2-(trimethylsilyl)ethoxy)methyl)-5H-pyrrolo[2,3-b]pyrazine-7-carboxamide (0.05 g, 0.000117 mol) and (4-aminophenyl)methanol (0.017 g, 0.00014 mol) was taken in toluene (2.0 ml). The reaction mixture was purged with argon for 15 min at RT after which CS$_2$CO$_3$ (0.189 g, 0.000586 mol) was added and the reaction mixture was further purged for 30 min with argon. BINAP (0.0015 g, 0.0000023 mol) and Pd(OAc)$_2$ (0.0005 g, 0.0000023 mol) were added to reaction mixture and heated to 110° C. for 4 hr. After completion of the reaction, the reaction mixture was filtered through celite bed and washed with ethyl acetate. Filtrate was collected and concentrated to afford crude product which was purified using column purification by eluting the compound with 20-25% ethyl acetate in hexanes to yield 0.05 g of N-tert-butyl-2-(4-(hydroxymethyl)phenyl-amino)-5-((2-(trimethylsilyl)ethoxy)methyl)-5H-pyrrolo[2,3-b]pyrazine-7-carboxamide.

Step 5

To a 10 ml seal tube, N-tert-butyl-2-(4-formylphenylamino)-5-((2-(trimethylsilyl)-ethoxy)methyl)-5H-pyrrolo[2,3-b]pyrazine-7-carboxamide (0.038 g, 0.000081 mol) was taken in CH$_2$Cl$_2$ (1.0 ml). PCC (0.087 g, 0.000405 mol) was added at 0° C. under nitrogen atmosphere. The reaction mixture was stirred for 2 hr at room temperature. After completion of the reaction, the reaction mixture was filtered through celite bed and washed with CH$_2$Cl$_2$. Filtrate was collected and concentrated to afford crude product which was purified using column purification by eluting the compound with 20-30% ethyl acetate in hexanes to yield 0.022 g of N-tert-butyl-2-(4-formylphenylamino)-5-((2-(trimethylsilyl)ethoxy)methyl)-5H-pyrrolo[2,3-b]pyrazine-7-carboxamide.

Step 6

To a 25 ml three necked round bottom flask, N-tert-butyl-2-(4-formylphenylamino)-5-((2-(trimethylsilyl)ethoxy)methyl)-5H-pyrrolo[2,3-b]pyrazine-7-carboxamide (0.022 g, 0.000047 mol) and 2-cyano-N,N-dimethylacetamide (0.021 g, 0.000187 mol) was taken in ethanol (2 ml). Piperidine acetate (3.3 M solution in water) (0.2 ml) was added dropwise at RT. After completion of the addition, reaction mixture was refluxed overnight. After completion of the reaction, the ethanol was distilled out and water was added to the residue.

Aqueous was extracted with ethyl acetate, organic layers were combined, dried over Na$_2$SO$_4$, filtered and concentrated to afford crude product which was purified by triturated with n-pentane. The solid was filtered and dried under vacuum to yield 0.015 g of N-tert-butyl-2-(4-(2-cyano-3-(dimethylamino)-3-oxoprop-1-enyl)phenylamino)-5-((2-(trimethylsilyl)ethoxy)-methyl)-5H-pyrrolo[2,3-b]pyrazine-7-carboxamide.

Step 7

In a 25 ml one necked round bottom flask, N-tert-butyl-2-(4-(2-cyano-3-(dimethylamino)-3-oxoprop-1-enyl)phenylamino)-5-((2-(trimethylsilyl)ethoxy)methyl)-5H-pyrrolo[2,3-b]pyrazine-7-carboxamide (0.1 g, 0.00019 mol) was taken in CH$_2$Cl$_2$ (10 ml) followed by dropwise addition of TFA (2.0 ml) at 0°-5° C. and the reaction was allowed to stir at room temperature for 24 hr. After completion of the reaction, the pH of the solution was adjusted to neutral by the addition of saturated sodium bicarbonate solution and extracted with CH$_2$Cl$_2$ and the combined organic layer was dried over anhy. sodium sulphate and concentrated to obtain crude mixture which was dissolved in ethanol (10 ml). NaOAc.3H$_2$O (0.242 g, 0.00178) was added and the reaction mixture was stirred at room temperature for 20 hr. Ethanol was distilled out and the reaction mixture was diluted with water and extracted with ethyl acetate. The combined organic layers were dried over sodium sulphate, concentrated to afford crude product which was purified using column purification by eluting the compound with 50% ethyl acetate in hexanes to yield 14.0 mg of N-tert-butyl-2-(4-(2-cyano-3-(dimethylamino)-3-oxoprop-1-enyl)phenylamino)-5H-pyrrolo[2,3-b]pyrazine-7-carboxamide.

Proceeding as described above but substituting tert-butylamine with isopropylamine, N-isopropyl-2-(4-(2-cyano-3-(dimethylamino)-3-oxoprop-1-enyl)phenylamino)-5H-pyrrolo[2,3-b]pyrazine-7-carboxamide was prepared.

Proceeding as described above but substituting 2-cyano-N,N-dimethylacetamide with tert-butyl 4-(2-cyanoacetyl)piperazine-1-carboxylate, N-(tert-butyl)-2-((4-(2-cyano-3-oxo-3-(piperazin-1-yl)prop-1-en-1-yl)phenyl)amino)-5H-pyrrolo[2,3-b]pyrazine-7-carboxamide was prepared.

Proceeding as described above but substituting 2-cyano-N,N-dimethylacetamide with tert-butyl 4-(2-cyanoacetyl)piperazine-1-carboxylate and substituting tert-butyl amine with isopropylamine, 2-((4-(2-cyano-3-oxo-3-(piperazin-1-yl)prop-1-en-1-yl)phenyl)amino)-N-isopropyl-5H-pyrrolo[2,3-b]pyrazine-7-carboxamide was prepared.

Proceeding as described above but substituting 2-cyano-N,N-dimethylacetamide with 3-(4-methylpiperazin-1-yl)-3-oxopropanenitrile, N-(tert-butyl)-2-((4-(2-cyano-3-(4-methylpiperazin-1-yl)-3-oxoprop-1-en-1-yl)phenyl)amino)-5H-pyrrolo[2,3-b]pyrazine-7-carboxamide was prepared.

Proceeding as described above but substituting 2-cyano-N,N-dimethylacetamide with 2-morpholino-2-oxoacetyl cyanide, N-(tert-butyl)-2-((4-(2-cyano-3-morpholino-3-oxoprop-1-en-1-yl)phenyl)amino)-5H-pyrrolo[2,3-b]pyrazine-7-carboxamide Proceeding as described above but substituting 2-cyano-N,N-dimethylacetamide with 3-(4-methylpiperazin-1-yl)-3-oxopropanenitrile and substituting tert-butyl amine with isopropylamine, 2-((4-(2-cyano-3-(4-methylpiperazin-1-yl)-3-oxoprop-1-en-1-yl)phenyl)amino)-N-isopropyl-5H-pyrrolo[2,3-b]pyrazine-7-carboxamide was prepared.

Example 11

Synthesis 2-cyano-N,N-dimethyl-3-(5-(7-pivaloyl-5H-pyrrolo[2,3-b]pyrazin-2-ylamino)-thiophen-2-yl)acrylamide

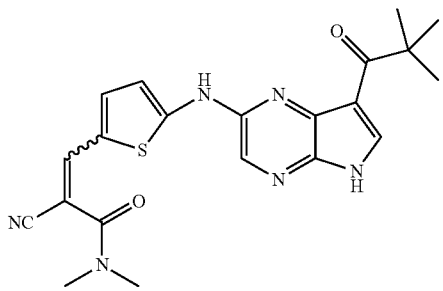 [SMILES: CN(C)C(=O)C(C#N)=Cc1ccc(Nc2cnc3[nH]cc(C(=O)C(C)(C)C)c3n2)s1]

Step 1

To a 250 ml three necked round bottom flask, 5-nitro 2-thiophenecarbaldehyde (1.25 g, 0.00795 mol) was added in methanol (26.7 ml) and water (8.9 ml). Conc.HCl (0.8 ml) was added followed by addition of Fe powder (2.22 g, 0.04 mol) and ammonium chloride (2.12 g, 0.04 mol). The reaction mixture was heated to 70°-80° C. After completion of reaction, the reaction mixture methanol was distilled out and sodium bicarbonate solution was added until the pH was neutral and the product was extracted with ethyl acetate. The combined organic layer were washed with water, dried over sodium sulphate and evaporated to afford brown solid which was purified using column purification by eluting the compound with 20% ethyl acetate in hexanes to yield 0.28 g of 5-amino 2-thiophene carbaldehyde.

Step 2

To a 10 ml seal tube, 1-(2-bromo-5-((2-(trimethylsiilyl)ethoxy)methyl)-5H-pyrrolo[2,3-b]pyrazin-7-yl)-2,2-dimethylpropan-1-one (0.400 g, 0.000969 mole), 5-amino 2-thiophenecarbaldehyde (0.147 g, 0.001162 mole) was added in toluene (5 ml) and the reacting mixture was purged with argon gas for 10 min. Cesium carbonate (0.947 g, 0.002907 mole) was added and again purged with argon gas for 10 min. Davephos (0.057 g, 0.000145 mole), Pd$_2$(dba)$_3$ (0.065 g, 0.000072 mole) were added and the reaction mixture was heated at 100° C. for 4 hr. After completion of the reaction, the reaction mixture was poured in to water and extracted with ethyl acetate. The combined organics were washed with brine solution. The organic layer was separated and dried over sodium sulphate, concentrated to give the desired crude product which was purified using column purification by eluting the compound with 35% ethyl acetate in hexane to yield 150 mg of 5-(7-pivaloyl-5-((2-trimethylsilyl)ethoxy)-methyl)-5H-pyrrolo[2,3-b]pyrazin-2-ylamino)thiophene-2-carbaldehyde.

Step 3

To a 10 ml seal tube was added 5-(7-pivaloyl-5-((2-trimethylsilyl)ethoxy)methyl)-5H-pyrrolo[2,3-b]pyrazin-2-ylamino)thiophene-2-carbaldehyde (0.150 g, 0.000327 mole), 2-cyano-N,N-dimethylacetamide (0.183 g, 0.00163 mole) and ethanol (5 ml) followed by addition of piperidine acetate (3.3 M solution in water) (1.5 ml, 0.00495 mole) at RT. The tube was sealed and the reaction mixture was heated at 80° C. for 24 hr. After completion of reaction, ethanol was distilled out, the reaction mixture was diluted with ethyl acetate. The organic layer was separated and washed with water, dried over sodium sulphate and concentrated to give the desired crude product which was purified using column purification by eluting the compound with 35% ethyl acetate in hexane to yield 110 mg of 2-cyano-N,N-dimethyl-3-(5-(7-pivaloyl-5-((2-trimethylsilyl)ethoxy)methyl)-5H-pyrrolo[2,3-b]pyrazin-2-ylamino)thiophen-2-yl)acrylamide.

Step 4

To a 25 ml one necked round bottom flask was added 2-cyano-N,N-dimethyl-3-(5-(7-pivaloyl-5-((2-trimethylsilyl)ethoxy)methyl)-5H-pyrrolo[2,3-b]pyrazin-2-ylamino)thiophen-2-yl)acrylamide (110 mg, 0.00019 mole) and $CH_2Cl_2$ (10 ml) followed by dropwise addition of TFA (2.2 ml) at 0°-5° C. The reaction mixture was allowed to stir at room temperature for 24 hr. After completion of the reaction, sodium bicarbonate solution added until pH was neutral and organics were distilled out. The crude compound was purified using column purification by eluting the compound with 70% ethyl acetate in hexane to yield a reddish brown solid which was dissolved in ethanol (10 ml). $NaOAc.3H_2O$ (0.264 g, 0.00190) was added and the reaction mixture was stirred at room temperature for 20 hr. Ethanol was evaporated and the reaction mixture was diluted with water and extracted with ethyl acetate. The combined organic layers were dried over sodium sulphate, concentrated to give the 34.0 mg of 2-cyano-N,N-dimethyl-3-(5-(7-pivaloyl-5H-pyrrolo[2,3-b]pyrazin-2-ylamino)thiophen-2-yl)acrylamide.

Example 12

Synthesis of 3-ethyl-5-(4-(7-pivaloyl-5H-pyrrolo[2,3-b]pyrazin-2-ylamino)benzylidene)thiazolidine-2,4-dione

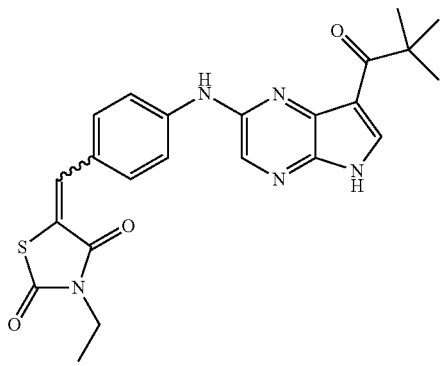 [SMILES: CCN1C(=O)SC(=Cc2ccc(Nc3cnc4[nH]cc(C(=O)C(C)(C)C)c4n3)cc2)C1=O]

To a 100 ml three necked round bottom flask, sodium hydride (60% in paraffin) (0.188 g, 0.00470 mole) was taken in DMF (2.0 ml). Thiazolidine-2,4-dione (0.5 g, 0.00427 mole) in DMF (3 ml) was slowly added at 0° C. over 15 min under nitrogen atmosphere. After addition was complete, the reaction mixture was stirred for 1 hr at 50° C. The reaction was then cooled to 0° C., followed by drop wise addition of ethyl iodide (0.41 ml, 0.00512 mole) at 0° C. The reaction mixture was warmed up to RT and stirred for 1 hr. After completion of the reaction, the reaction mixture was poured in water and aq. layer was extracted with ethyl acetate. Organic layers were combined and washed with brine solution, dried over $Na_2SO_4$, filtered and concentrated to afford crude product which was purified using column purification by eluting the compound with 5% ethyl acetate in hexanes to yield 0.5 g of 3-ethylthiazolidine-2,4-dione.

Step 2

To a 50 ml three necked round bottom flask, 4-(7-pivaloyl-5-((2-(trimethylsilyl)-ethoxy)methyl)-5H-pyrrolo[2,3-b]pyrazine-2-ylamino)benzaldehyde (0.104 g, 0.00023 mole) and 3-ethylthiazolidine-2,4-dione (0.067 g, 0.00046 mole) was taken in ethanol (3 ml). Piperidine acetate (3.3 M solution in water) (0.1 ml) was added dropwise at RT. The reaction mixture was refluxed for 6 hrs. After completion of the reaction, ethanol was distilled out and water was added to residue. Aq. layer was extracted with ethyl acetate, the combined organic layers were dried over $Na_2SO_4$, filtered and concentrated to afford crude product which was purified by triturated with n-pentane. The solid was filtered and dried under vacuum to yield 0.070 g of 3-ethyl-5-(4-(7-pivaloyl-5-((2-(trimethylsilyl)ethoxy)methyl)-5H-pyrrolo[2,3-b]pyrazin-2-ylamino)benzylidene)thiazolidine-2,4-dione which was converted to the title compounds as described in Example 6 above.

Example 13

Synthesis of ethyl 2-cyano-3-(4-(7-pivaloyl-5H-pyrrolo[2,3-b]pyrazin-2-ylamino)-phenyl)acrylate

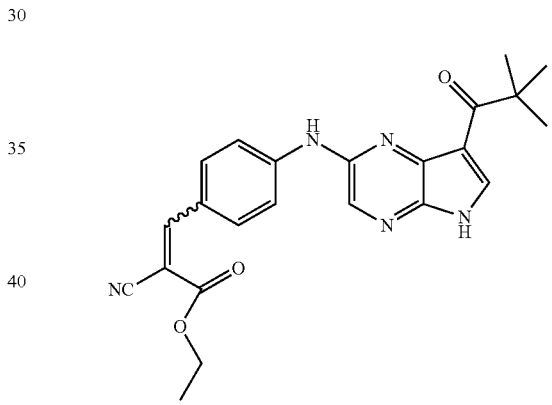

To a 25 ml one necked round bottom flask was added 4-(7-pivaloyl-5-((2-(trimethylsilyl)ethoxy)methyl)-5H-pyrrolo[2,3-b]pyrazin-2-ylamino)benzaldehyde (100 mg, 0.000221 mole), ethyl 2-cyano acetate (75 mg, 0.000663 mole) and ethanol (3 ml) followed by addition of piperidine acetate (3.3 M solution in water) (0.03 ml, 0.000663 mole) at RT and the reaction was heated at 80° C. for 2 hr. After completion of the reaction, the reaction mixture was concentrated, diluted with water and extracted with $CH_2Cl_2$. The combined organics were washed with water, dried over sodium sulphate, concentrated to give the desired crude product which was subjected for the purification. 30% Ethyl acetate in hexanes (5 ml) was added to a crude solid and resulting suspension was stirred for 30 minutes at room temperature. The suspension was filtered under vacuum; washed with hexanes and dried under vacuum to yield 100 mg of ethyl 2-cyano-3-(4-(7-pivaloyl-5-((2-(trimethyl-silyl)ethoxy)methyl)-5H-pyrrolo[2,3-b]pyrazin-2-ylamino)phenyl)acrylate which was converted to the title compound as described in Example 8 above.

Example 14

Synthesis of 2-(methylsulfonyl)-3-(4-(7-pivaloyl-5H-pyrrolo[2,3-b]pyrazin-2-ylamino)phenyl)acrylonitrile

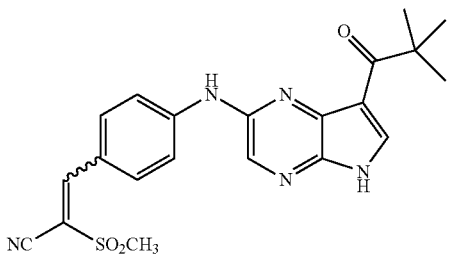 [SMILES: CC(C)(C)C(=O)c1c[nH]c2ncc(Nc3ccc(C=C(C#N)S(C)(=O)=O)cc3)nc12]

To a 10 ml seal tube, 4-(7-pivaloyl-5-((2-(trimethylsilyl)ethoxy)methyl)-5H-pyrrolo[2,3-b]pyrazin-2-ylamino)benzaldehyde (0.1 g, 0.00022 mol) and 2-(methylsulfonyl)acetonitrile (0.105 g, 0.00088 mol) were taken in ethanol (5 ml). Piperidine acetate (3.3 M solution in water) (1.0 ml) was added dropwise at RT. After completion of the addition, reaction mixture was refluxed for 24 hr. After completion of the reaction, ethanol was distilled out to obtain crude product. The crude product was purified by column chromatography using 30% ethyl acetate in hexanes to yield 0.078 g of 2-(methylsulfonyl)-3-(4-(7-pivaloyl-5-((2-(trimethylsilyl)ethoxy)methyl)-5H-pyrrolo[2,3-b]pyrazin-2-ylamino)phenyl)acrylonitrile which was converted to the title compound as described above.

Example 15

Synthesis of 3-(4-(7-pivaloyl-5H-pyrrolo[2,3-b]pyrazin-2-ylamino)phenyl)-2-(thiazol-2-yl)acrylonitrile

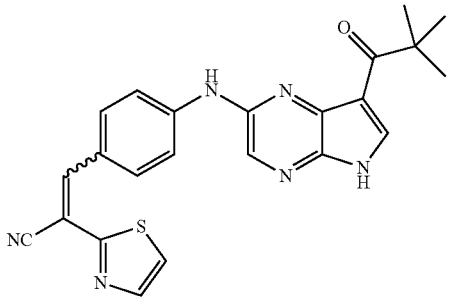 [SMILES: CC(C)(C)C(=O)c1c[nH]c2ncc(Nc3ccc(C=C(C#N)c4nccs4)cc3)nc12]

Step 1

To a 25 ml three necked round bottom flask, 4-(7-pivaloyl-5-((2-(trimethylsilyl)ethoxy)methyl)-5H-pyrrolo[2,3-b]pyrazin-2-ylamino)benzaldehyde (0.1 g, 0.000221 mol) and 2-(thiazol-2-yl)acetonitrile (0.082 g, 0.000663 mol) were taken in ethanol (5 ml). Piperidine acetate (3.3 M solution in water) (0.2 ml) was added dropwise at RT. After completion of the addition, reaction mixture was refluxed overnight and ethanol was distilled out and water was added to residue. The aqueous layer was extracted with ethyl acetate, the organic layers were combined, dried over Na$_2$SO$_4$, filtered and concentrated to afford crude product. The crude compound was triturated with n-pentane, the pentane layer was decanted and solid was dried under vacuum to yield 0.090 g of 3-(4-(7-pivaloyl-5-((2-(trimethylsilyl)ethoxy)methyl)-5H-pyrrolo[2,3-b]pyrazin-2-ylamino)phenyl)-2-(thiazol-2-yl)acrylonitrile.

Step 2

To a 25 ml one necked round bottom flask, 3-(4-(7-pivaloyl-5-((2-(trimethylsilyl)-ethoxy)methyl)-5H-pyrrolo[2,3-b]pyrazin-2-ylamino)phenyl)-2-(thiazol-2-yl)acrylonitrile (0.09 g, 0.000161 mol) was taken in CH$_2$Cl$_2$ (10 ml) followed by dropwise addition of TFA (2.0 ml) at 0°-5° C. and the reaction was allowed to stir at room temperature for 24 hr. After completion of the reaction, the pH of the solution was adjusted to neutral by the addition of saturated sodium bicarbonate solution and the product was extracted with CH$_2$Cl$_2$. The combined organic layer was dried over anhy. sodium sulphate and concentrated to obtain crude mixture which was dissolved in ethanol (10 ml) and NaOAc.3H$_2$O (0.219 g, 0.00161 moles) was added and the reaction mixture was stirred it at room temperature for 20 hr. Ethanol was removed and the reaction mixture was diluted with water, followed by extraction with ethyl acetate. The combined organic layers were dried over sodium sulphate, concentrated to afford crude product which was purified using column purification by eluting the compound with 50% ethyl acetate in hexanes to yield 35.0 mg of 3-(4-(7-pivaloyl-5H-pyrrolo[2,3-b]pyrazin-2-ylamino)phenyl)-2-(thiazol-2-yl)acrylonitrile.

Example 16

Synthesis of 3-[4-[[7-(2,2-dimethylpropanoyl)-5H-pyrrolo[2,3-b]pyrazin-2-yl]amino]phenyl]-2-(piperidine-1-carbonyl)prop-2-enenitrile

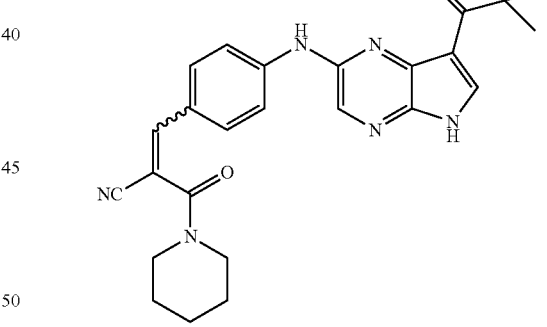

Step 1

To a 20 ml vial 4-[[7-(2,2-dimethylpropanoyl)-5-(2-trimethylsilylethoxymethyl)-pyrrolo[2,3-b]pyrazin-2-yl]amino]benzaldehyde (35 mg, 0.0800 mmol), 3-oxo-3-(1-piperidyl)propanenitrile (18.01 mg, 0.1200 mmol), piperdine (0.02 ml, 0.15 mmol) and 3-oxo-3-(1-piperidyl)propanenitrile (18.01 mg, 0.12 mmol), were taken in methanol (5 ml). To this reaction mixture, piperdine (0.02 ml, 0.15 mmol) was added drop wise at RT. After completion of the addition, the reaction mixture was stirred for 5 hrs. Ethanol was evaporated, the residue was loaded on silica gel column and elution with CH$_2$Cl$_2$ to MeOH 0-2, 3% yielded 28 mg of 3-[4-[[7-(2,2-dimethylpropanoyl)-5-(2-trimethylsilylethoxymethyl)pyrrolo[2,3-b]pyrazin-2-yl]amino]phenyl]-2-(piperidine-1-carbonyl)prop-2-enenitrile.

Step 2.

To a 20 ml vial, 3-[4-[[7-(2,2-dimethylpropanoyl)-5-(2-trimethylsilylethoxymethyl)-pyrrolo[2,3-b]pyrazin-2-yl]amino]phenyl]-2-(piperidine-1-carbonyl)prop-2-enenitrile (0.04 ml, 0.04 mmol) was dissolved in DCM (3 ml) and the reaction mixture was cooled to 0° C. TFA (2 ml, 0.0238 mole) was added drop wise at 0° C. and there reaction mixture was stirred for 3 h at room temperature. The solvent was evaporated and the residue was neutralized by NaHCO$_3$ to pH 7-8 and the aq. layer was extracted with EtOAc. The organic layer was evaporated and the residue was dissolved in methanol. HCl and water were added and the solution was stirred at RT overnight and then neutralized with NaHCO$_3$ to pH7-8. The crude product which precipitated was filtrated, washed with water and dried. The crude product was dissolved in a mixture of EtOAC and CH$_2$Cl$_2$, loaded on TLC plate and flashed with EtOAc:hexane=85:15 to yield 0.014 g of 3-[4-[[7-(2,2-dimethylpropanoyl)-5H-pyrrolo[2,3-b]pyrazin-2-yl]amino]phenyl]-2-(piperidine-1-carbonyl)prop-2-enenitrile.

Example 17

Synthesis of 2-cyano-3-[4-[[7-(2,2-dimethylpropanoyl)-5H-pyrrolo[2,3-b]pyrazin-2-yl]amino]phenyl]-N-ethyl-prop-2-enamide

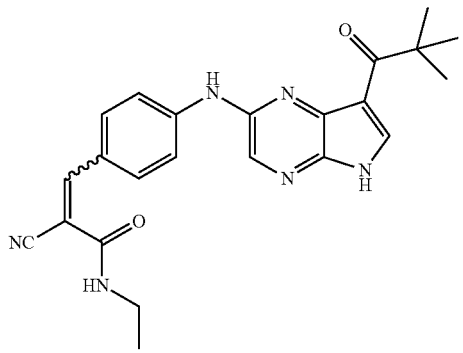 [SMILES: CCNC(=O)C(C#N)=Cc1ccc(Nc2cnc3[nH]cc(C(=O)C(C)(C)C)c3n2)cc1]

Step 1

To a 20 ml vial 4-[[7-(2,2-dimethylpropanoyl)-5-(2-trimethylsilylethoxymethyl)-pyrrolo[2,3-b]pyrazin-2-yl]amino]benzaldehyde (30 mg, 0.070 mmol) was dissolved in methanol (5 ml) and 2-cyano-N-ethyl-acetamide (11.38 mg, 0.1000 mmol) and piperdine (0.01 ml, 0.1300 mmol) were added. The reaction mixture was stirred at room temperature for 5 hr. The solvent was evaporated, the residue was loaded on a silica gel column and eluted with CH$_2$Cl$_2$ to MeOH 0-2, 3% to yield 37 mg of 2-cyano-3-[4-[[7-(2,2-dimethylpropanoyl)-5-(2-trimethylsilylethoxymethyl)pyrrolo[2,3-b]pyrazin-2-yl]amino]phenyl]-N-ethyl-prop-2-enamide.

Step 2

To a 20 ml vial 2-cyano-3-[4-[[7-(2,2-dimethylpropanoyl)-5-(2-trimethylsilylethoxy-methyl)-pyrrolo[2,3-b]pyrazin-2-yl]amino]phenyl]-N-ethyl-prop-2-enamide (37 mg, 0.07 mmol was dissolved in DCM (3 ml) and TFA (2.63 ml, 18.88 mmol) was added. The reaction mixture was stirred at room temperature for 3 hr. The solvent was evaporated, the residue was neutralized with NaHCO$_3$ to pH 7-8 and the aq. layer was extracted with EtOAc. The solvent was evaporated and the residue was dissolved in methanol (5 ml). HCl (4 drops) and water, were added and the reaction mixture was stirred at RT overnight. The reaction was neutralized with NaHCO$_3$ to pH 7-8. The product was precipitated, filtrated and washed by water to yield 20 mg 2-cyano-3-[4-[[7-(2,2-dimethylpropanoyl)-5H-pyrrolo[2,3-b]pyrazin-2-yl]amino]phenyl]-N-ethyl-prop-2-enamide as dark red brown solid.

Following the procedure above and replacing 2-cyano-N-ethyl-acetamide with 2-cyano-N-isopropyl-acetamide, 2-cyano-3-[4-[[7-(2,2-dimethylpropanoyl)-5H-pyrrolo[2,3-b]pyrazin-2-yl]amino]phenyl]-N-isopropyl-prop-2-enamide was prepared.

Following the procedure above and replacing 2-cyano-N-ethyl-acetamide with 2-cyano-N-n-propyl-acetamide 2-cyano-3-[4-[[7-(2,2-dimethylpropanoyl)-5H-pyrrolo[2,3-b]pyrazin-2-yl]amino]phenyl]-N-n-propylprop-2-enamide was prepared.

Example 18

Synthesis of 2-[4-(2-cyano-3-morpholino-3-oxo-prop-1-enyl)anilino]-N-isopropyl-5H-pyrrolo[2,3-b]pyrazine-7-carboxamide

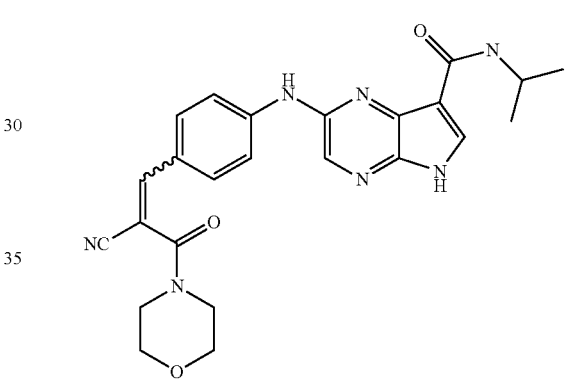

Step 1

To a 20 ml vial 2-(4-formylanilino)-N-isopropyl-5-(2-trimethylsilylethoxymethyl)-pyrrolo[2,3-b]pyrazine-7-carboxamide (50 mg, 0.11 mmol), 3-morpholino-3-oxopropanenitrile (33.99 mg, 0.22 mmol) and piperdine (0.02 ml, 0.22 mmol) were mixed and stirred overnight. The residues was dissolved in minimum CH$_2$Cl$_2$, loaded on silica gel column, and eluted with EtOAc:hexane, 0, 50, 80, 100% to get 60 mg of 2-[4-(2-cyano-3-morpholino-3-oxo-prop-1-enyl)anilino]-N-isopropyl-5-(2-trimethylsilylethoxymethyl)pyrrolo[2,3-b]pyrazine-7-carboxamide as a white solid.

Step 2

To a 20 ml vial 2-[4-(2-cyano-3-morpholino-3-oxo-prop-1-enyl)anilino]-N-isopropyl-5-(2-trimethylsilylethoxymethyl)pyrrolo[2,3-b]pyrazine-7-carboxamide (65 mg, 0.11 mmol was dissolved in DCM (3 ml) added TFA (3 ml, 0.11 mmol) was added. The reaction mixture was stirred overnight. HCl (1 ml, 0.11 mmol) and methanol (3 ml) were added and the reaction mixture was stirred at overnight and then neutralized to pH 6-7 with NaHCO$_3$. The organics were extracted with EtOAc, washed with water, dried with Na$_2$SO$_4$, filtered and evaporated solvent to give 45 mg of 2-[4-(2-cyano-3-morpholino-3-oxo-prop-1-enyl)anilino]-N-isopropyl-5H-pyrrolo[2,3-b]pyrazine-7-carboxamide as yellow solid.

Example 19

Synthesis of 2-(piperazine-1-carbonyl)-3-(4-((7-pivaloyl-5H-pyrrolo[2,3-b]pyrazin-2-yl)amino)phenyl)acrylonitrile

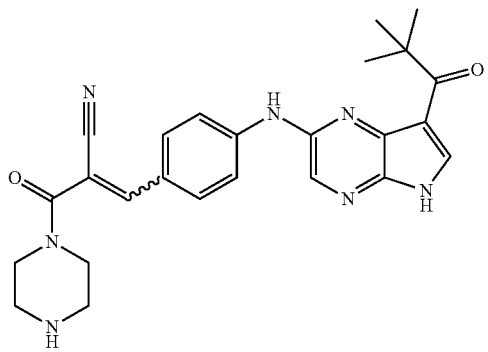 [SMILES: CC(C)(C)C(=O)c1c[nH]c2ncc(Nc3ccc(C=C(C#N)C(=O)N4CCNCC4)cc3)nc12]

Step 1

4-[[7-(2,2-Dimethylpropanoyl)-5-(2-trimethylsilylethoxymethyl)pyrrolo[2,3-b]pyrazin-2-yl]amino]benzaldehyde (90 mg, 0.2 mmol, tert-butyl 4-(2-cyanoacetyl)piperazine-1-carboxylate (60.44 mg, 0.24 mmol and piperdine (0.04 mL, 0.4 mmol were combined and stirred overnight. When the reaction was complete by TLC, the solvent was removed and the residue was dissolved in minimum of CH₂Cl₂, loaded on TLC plate, flashed it by EtOH:CH₂Cl₂ 4% to get tert-butyl 4-(2-cyano-3-((4-(7-pivaloyl-5-((2-(trimethylsilyl)ethoxy)methyl)-5H-pyrrolo[2,3-b]pyrazin-2-yl)amino)phenyl)acryloyl)piperazine-1-carboxylate.

Step 2

Tert-butyl 4-[2-cyano-3-[4-[[7-(2,2-dimethylpropanoyl)-5-(2-trimethylsilylethoxy-methyl)-pyrrolo[2,3-b]pyrazin-2-yl]amino]phenyl]prop-2-enoyl]piperazine-1-carboxylate (80 mg, 0.12 mmol) was dissolved in DCM (3 mL), cooled in an ice bath, and TFA (3 mL, 0.12 mmol) was added. The reaction mixture was stirred overnight, and then most of the solvent was removed in vacuo. The mixture was neutralized by Na₂HCO3 to pH 7-8, extracted by EtOAc, combined organic layer was evaporated. The residue was dissolved in methanol (15 mL), adding HCl (0.05 mL, 0.12 mmol, and a few of drops water, and the mixtured was stirred overnight. When the reaction was deemed complete by LCMS analysis, the solvent was removed, and the product precipitated from EtOAc/MeOH to get 21 mg of 2-(piperazine-1-carbonyl)-3-(4-((7-pivaloyl-5H-pyrrolo[2,3-b]pyrazin-2-yl)amino)phenyl)acrylonitrile.

Example 20

Synthesis of 3-(4-(7-pivaloyl-5H-pyrrolo[2,3-b]pyrazin-2-ylamino)phenyl)-2-(1H-1,2,4-triazol-1-yl)acrylonitrile

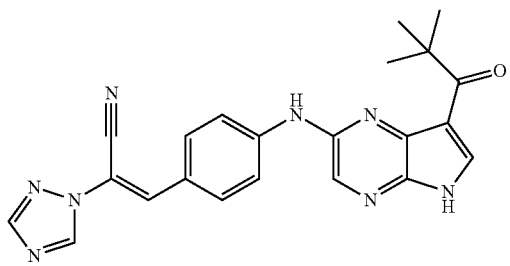 [SMILES: CC(C)(C)C(=O)c1c[nH]c2ncc(Nc3ccc(/C=C(\C#N)n4cncn4)cc3)nc12]

Step 1

To a 50 ml three necked round bottom flask, 4-(7-pivaloyl-5-((2-(trimethylsilyl)ethoxy)-methyl)-5H-pyrrolo[2,3-b]pyrazine-2-ylamino)benzaldehyde (0.1 g, 0.22 mmole) and 2-(1H-1,2,4-triazol-1-yl)acetonitrile (0.0716 g, 0.66 mmole) was taken in ethanol (5 mL). To this reaction mixture, piperidine (0.2 mL) was added drop wise at RT. After completion of the addition, the reaction mass was refluxed for 16 hrs and the completion of the reaction was monitored on TLC using ethyl acetate:hexane (5:5) as a mobile phase. After completion of the reaction, ethanol was distilled out and water was added to residue. Aqueous was extracted with ethyl acetate, organic layers were combined, dried over Na₂SO₄, filtered and concentrated to afford crude product. The crude compound was purified using column purification by eluting the compound with 40% ethyl acetate in hexanes triturated with n-pentane, pentane layer was decanted and solid was dried under vacuum to yield 0.052 g of 3-(4-(7-pivaloyl-5-((2-(trimethylsilyl)ethoxy)methyl)-5H-pyrrolo[2,3-b]pyrazin-2-ylamino)phenyl)-2-(1H-1,2,4-triazol-1-yl)acrylonitrile.

Step 2

To a 25 ml one necked round bottom flask, 3-(4-(7-pivaloyl-5-((2-(trimethylsilyl)ethoxy)methyl)-5H-pyrrolo[2,3-b]pyrazin-2-ylamino)phenyl)-2-(1H-1,2,4-triazol-1-yl)acrylonitrile (0.052 g, 0.95 mmole) was taken in CH₂Cl₂ (5 mL). TFA (1.5 mL) was added drop wise at 0° C. After completion of the addition, the reaction mass was warmed up to RT and stirred for 16 hrs at the same temperature. After completion of the reaction, CH₂Cl₂ was distilled out to get solid. The solid was taken in ethanol (10 mL) and sodium acetate trihydrate (0.130 g, 0.95 mmole) was added at RT. The reaction mixture was stirred for 20 hrs at RT. After completion of the reaction the ethanol was distilled out under vacuum. To the residue, water (20 mL) was added and stirred for 15 min, filtered and wash with water and n-pentane. The solid was dried under vacuum to yield 21 mg of 3-(4-(7-pivaloyl-5H-pyrrolo[2,3-b]pyrazin-2-ylamino)phenyl)-2-(1H-1,2,4-triazol-1-yl)acrylonitrile.

Example 21

Synthesis of 3-(2-(dimethylamino)ethyl)-5-(4-(7-pivaloyl-5H-pyrrolo[2,3-b]pyrazin-2-ylamino)benzylidene)-thiazolidine-2,4-dione

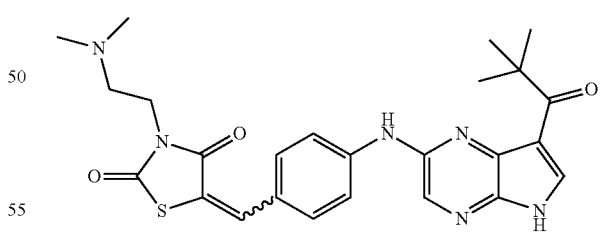

Step 1

To a 50 ml 3-neck flask, NaH (60% in mineral oil) (0.614 g, 25.6 mmole) was taken in DMF (20 mL) under N₂ atmosphere and cooled to 0° C. To this, thiazolidine-2,4-dione (2.0 g, 1.707 mmole) followed by dibromoethane (1.61 mL, 18.78 mmole) were added at 0° C. and the reaction mixture was stirred at room temperature for 2 hrs. After completion of the reaction, ice was added to the reaction mixture and product was extracted with EtOAc. The combined organic layer was washed with water, dried over Na2SO4 and evaporated to get the crude product which was subjected for the column purification. The crude compound was purified using column purification using 60-120 mesh size neutral silica by eluting the compound with 20-25% EtOAc in hexanes to yield 1.5 g of 3-(2-bromoethyl)thiazolidine-2,4-dione.

Step 2

To a 35 ml seal tube, 3-(2-bromoethyl)thiazolidine-2,4-dione (1.5 g, 0.6.69 mmole) was taken in DMF (1 mL) under $N_2$ atmosphere and dimethyl amine (2M solution in THF) (11 mL, 20.0 mmole) was added. The reaction mixture was heated to 50° C. for 16 hrs. After completion of the reaction, water was added to the reaction mixture and product was extracted with ethyl acetate. The combined organic layer was dried over $Na_2SO_4$ and evaporated to get the crude product which was purified using column purification using 60-120 mesh size neutral silica by eluting the compound with 2% MeOH in $CH_2Cl_2$ to yield 0.3 g of 3-(2-(dimethylamino) ethyl)thiazolidine-2,4-dione which was converted to 3-(2-(dimethylamino)-ethyl)-5-(4-(7-pivaloyl-5H-pyrrolo[2,3-b] pyrazin-2-ylamino)benzylidene)-thiazolidine-2,4-dione as described in Example 6 above.

Example 22

Synthesis of 3-(2-aminoethyl)-5-(4-((7-pivaloyl-5H-pyrrolo[2,3-b]pyrazin-2-ylamino)benzylidine)thiazolidine-2,4-dione

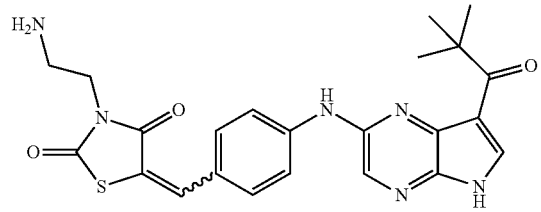 [SMILES: CC(C)(C)C(=O)c1c[nH]c2ncc(Nc3ccc(C=C4SC(=O)N(CCN)C4=O)cc3)nc12]

Step 1

To a 10 ml seal tube, thiazolidine-2,4-dione (0.25 g, 2.13 mmole), tert-butyl 2-bromoethylcarbamate (0.715 g, 3.19 mmole) were taken in acetone (4 mL) and $K_2CO_3$ (0.353 g, 2.56 mmole) and tetrabutylammonium iodide (TBAI) (0.078 g, 0.213 mmole) were added to it. The reaction mixture was heated at reflux temperature for 3 hr. After completion of the reaction, the reaction mixture was concentrated at reduced pressure, water was added and extracted with ethyl acetate. The combined organics were washed with water followed with brine solution. The organic layer was separated and dried over sodium sulphate, concentrated to give crude product which was purified using column purification by eluting the compound with 5% ethyl acetate in hexanes to yield 0.55 g of tert-butyl-2,(2,4-dioxothiazolidin-3-yl)ethyl carbamate. Tert-butyl-2,(2,4-dioxothiazolidin-3-yl)ethyl carbamate was converted to 3-(2-aminoethyl)-5-(4-(7-pivaloyl-5H-pyrrolo[2,3-b]pyrazin-2-ylamino)benzylidine)thiazolidine-2,4-dione as described in Example 6 above.

Biological Examples

Example 1

JAK3 Caliper Peptide Phosphorylation Assay

Phosphorylation of the appropriate peptide substrate (fluorescently labeled Srctide) by recombinant JAK3 (catalytic domain, aa 781-1124) was measured in the presence and absence of different concentrations of test compounds. Test compound, enzyme, fluorescently labeled substrate, and cofactors (ATP and $Mg^{2+}$) were combined in a well of a microtiter plate and incubated for 2 hours at 25° C. The composition of the reaction buffer was 100 mM HEPES pH 7.5, 5 mM $MgCl_2$, 0.01% Triton-X 100, 0.1% Bovine Serum Albumin, and 1% DMSO. Enzyme concentration in the final reaction mixture was 0.5 nM while peptide substrate was at 1 uM. ATP was used at 1×Km concentration corresponding to 2 uM. Serial dilutions (3-fold steps) of compounds were prepared in DMSO. At the end of the incubation, the reaction was stopped by the addition of 20 mM EDTA. Substrate and product (i.e. phosphorylated substrate) were separated electrophoretically and both were quantified by fluorescence intensity using the microfluidics-based LabChip 3000 Drug Discovery System from Caliper Life Sciences. Conversion for each well was calculated and plotted as function of test compound concentration. $IC_{50}$ value was determined by fitting the data to a 4-parameter logistic model by non-linear regression (XLfit model 205). In every assay, Staurosporine was tested in the same manner as reference compound. Selectivity for JAK3 was determined using commercially available kinase cross-screening services (DiscoveRx, San Diego, Calif.).

The $IC_{50}$ of a representative number of compounds of the disclosure is shown in Table below.

| CPD # | $IC_{50}$ um | CPD # | $IC_{50}$ um |
|---|---|---|---|
| 1 | 0.3049 | 66 | 0.0007 |
| 3 | 0.15 | 68 | 0.001 |
| 4 | >1 | 69 | 0.0005 |
| 6 | 0.58 | 70 | 0.0009 |
| 7 | >1 | 71 | 0.0002 |
| 11 | >1 | 73 | 0.21 |
| 12 | 0.28 | 76 | 0.001 |
| 15 | 2.2 | 77 | 0.001 |
| 16 | 1.27 | 78 | 0.0335 |
| 17 | 1.77 | 79 | 0.1 |
| 19 | >5 | 80 | 0.0007 |
| 27 | >1 | 81 | 0.0006 |
| 29 | >1 | 82 | 0.0383 |
| 31 | >1 | 83 | 0.0002 |
| 32 | 0.32 | 85 | 0.0055 |
| 37 | 0.19 | 86 | 0.0351 |
| 47 | 0.013 | 88 | 0.003 |
| 50 | 0.0002 | 89 | 0.003 |
| 51 | 1.153 | 96 | 0.6799 |
| 57 | 0.001 | 97 | 0.104 |
| 60 | 0.0004 | 100 | >5 |
| 62 | 0.0004 | 102 | 0.345 |
| 64 | 0.0002 | 65 | 0.004 |

JAK3 TR-FRET Assay

Inhibition of JAK3 enzymatic activity by compounds is measured using time-resolved fluorescence resonance energy transfer (TR-FRET). Here, a signal is observed only when a Europium-coupled phosphotyrosine antibody binds the phosphorylated peptide. Compounds are first prepared in 100% DMSO and serially diluted 10 times via 3-fold dilution. 2.5 ul of inhibitor at 4-fold the final assay concentration is next transferred to the 384-well assay plate (Corning Catalog #3676). A solution of 2-fold the final concentration of JAK3 enzyme (Invitrogen Catalog # PV3855) and Alexafluor 647-coupled peptide substrate (Invitrogen Catalog #5693) is next prepared in advance in a kinase buffer of 50 mM Hepes pH 7.5, 10 mM MgCl2, and 1 mM EGTA. For this solution, the final concentration of JAK3 and peptide is typically 1 nM and 100 nM, respectively. 5 uL of this 2-fold mix of JAK3 and peptide is added as the second step of the procedure to the 384-well assay plate. To initiate the enzymatic reaction, 2.5 ul of a 4-fold excess ATP solution in kinase buffer is added to the 384-well assay plate. Final ATP concentration is typically set to the Km for ATP. The reaction is allowed to proceed for 60 minutes. During the kinase reaction, a stop solution consisting of EDTA and a Europium-containing phosphotyrosine antibody (Invitrogen Catalog #5692) is prepared in TR-FRET dilution buffer (Invitrogen Catalog #3574). The stop solution contains an EDTA concentration of 20 mM and an antibody concentration of 4 nM. After the 60 minute reaction, 10 ul of the stop solution is added to all wells. Each well is mixed and incubated for 30 minutes at room temperature. Plates are read on a Perkin Elmer Envision TR-FRET plate reader under LanthaScreen settings. Excitation wavelength is 337 nm and Emission wavelengths are 620 nm and 665 nm. Data are acquired as the ratio of emission at 665 nm/emission at 620 nm and plotted as a function of compound concentration to ascertain compound potency. Selectivity for JAK3 will be determined using commercially available kinase cross-screening services (DiscoveRx, San Diego, Calif.).

Example 2

Cellular JAK3 Activity Measured by Stat6 Reporter Assay in Ramos Cells

The beta lactamase-based select-screen reporter assay was used to measure JAK3 cell-based activity (3). 32 µL of STAT6-bla RA1 (Invitrogen) cells diluted in Assay Media (OPTI-MEM, 0.5% dialyzed FBS, 0.1 mM NEAA, 1 mM Sodium Pyruvate, 100 U/ml/100 µg/ml Pen/Strep, 550 ng/ml CD40L) to appropriate cell density were added to the Poly-D-Lysine assay plate containing 4 µL of a 10× serial dilution of a JAK3 control compound or test compounds. Pre-incubation at 37° C./5% CO2 in a humidified incubator with compounds and control inhibitor titration was for 30 minutes. 4 µL of 10× control activator IL-4 at the predetermined EC80 concentration was added to wells containing the control inhibitor or compounds. The plate was incubated for 5 hours at 37° C./5% CO2 in a humidified incubator. 8 µL of 1 µM Substrate Loading Solution was added to each well and the plate was incubated for 2 hours at room temperature. The plate was read on a fluorescence plate reader and the data was analyzed. A response ratio was calculated from the emissions of cleaved and uncleaved substrate. The response ratio of wells with compound dilutions was compared with wells that contain only DMSO to calculate the percent inhibition at each compound concentration. A dose response curve was constructed and an $IC_{50}$ was calculated.

Example 3

Blockade of Stat5 Phosphorylation in Whole Blood or Peripheral Blood Mononuclear Cell (PBMC)

Activation of the IL-2 receptor leads to increased JAK3 activity, Stat5 phosphorylation and T cell activation (see O'Shea J. J, et al. A new modality for immunosuppression: targeting the JAK/STAT pathway. *Nat Rev Drug Discov.* 3:555-64. 2004). JAK3 inhibitors have been shown to block T cell activation as measured by Stat5 phosphorylation (see Lin et al. Selective functional inhibition of Jak-3 is sufficient for efficacy in collagen-induced arthritis in mice. *Arthritis & Rheumatism* 62:2283-2293. 2010). Peripheral blood mononuclear cells (PBMC) were prepared from human whole blood by centrifugation on a ficoll gradient. Aliquots of PBMC were pre-incubated with serial dilutions of test compound for 30 minutes followed by activation with IL-2 (pre-determined EC80 concentration). Samples were incubated for 15 minutes and then fixed with 2% paraformaldehyde for PBMCs. Fixed cells were stained with Alexa647-labeled anti-phosphoStat5 pY694 antibodies (BD Biosciences) for 45 minutes. Stat5 phosphorylation was then analyzed by flow cytometry. The percent inhibition was calculated based on a DMSO control for no inhibition and plotted as a function of test compound concentration from which an $IC_{50}$ value was calculated.

Example 4

Inhibition of Mouse Collagen-Induced Arthritis

Inhibition of murine collagen-induced arthritis (mCIA) is a standard animal disease model for rheumatoid arthritis. Previous studies have demonstrated that inhibition of JAK3 is efficacious in blocking mCIA (see Milici A. J, et al. Cartilage preservation by inhibition of Janus kinase 3 in two rodent models of rheumatoid arthritis. *Arthritis Res Ther.* 10:R14 1-9. 2008). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by elisa at the end of the study (Bolder BioPath, Boulder, Colo.).

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
| --- | --- |
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
| --- | --- |
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/ml The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:
1. A compound of Formula (I') or a pharmaceutically acceptable salt thereof:

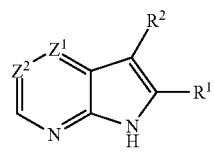

(I')

wherein:
$R^1$ is hydrogen, alkyl, halo, haloalkyl, haloalkoxy, cyano or cycloalkyl;
$R^2$ is hydrogen, alkyl, halo, haloalkyl, haloalkoxy, cyano, cycloalkyl, acyl, or aminocarbonyl;
$Z^1$ is N or $CR^3$ where $R^3$ is a ring of formula (A):

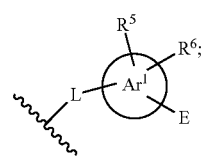

(A)

$Z^2$ is N or $CR^4$ where $R^4$ is a ring of formula (C):

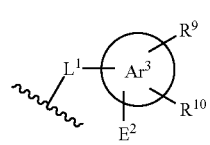

(C)

provided that (i) at least one of $Z^1$ and $Z^2$ is N, (ii) $Z^1$ and $Z^2$ are not simultaneously N; (iii) $R^2$ is hydrogen, alkyl, halo, haloalkyl, haloalkoxy, cyano, or cycloalkyl when $Z^1$ is $CR^3$; and (iv) $R^2$ is hydrogen, alkyl, cycloalkyl, halo, cyano, acyl, or aminocarbonyl when $Z^2$ is $CR^4$ and wherein:
L and $L^1$ are independently bond, $CH_2$, —NR—, —O—, CO, —S(O)n- (where n is 0-2), —NRCO—, —CONR—, or heteroalkylene (where R is hydrogen, alkyl or cycloalkyl);

$Ar^1$ and $Ar^3$ are independently aryl, heteroaryl, cycloalkyl or heterocyclyl;

$R^5$ and $R^9$ are independently hydrogen, alkyl, alkoxy, halo, haloalkyl, haloalkoxy, cyano, or cycloalkyl;

$R^6$ and $R^{10}$ are independently hydrogen, alkyl, alkoxy, halo, haloalkyl, haloalkoxy, cyano, cycloalkyl, hydroxyalkoxy, alkoxyalkoxy, aminoalkoxy, or alkylsulfonylalkoxy;

E and $E^2$ are independently:

(i) —P—CH═C($R^b$)(EWG) where P is a bond, $NR^a$ (where $R^a$ is hydrogen or alkyl), —O—, S, SO, $SO_2$, alkylene or heteroalkylene, $R^b$ is cyano, nitro, halo, haloalkyl, haloalkoxy, alkylthio, or alkylsulfonyl; and EWG is —S($O_2$)R', —S(O)R', —C(O)$NH_2$, —C(O)NHR$^g$, —C(O)NR$^f$R$^g$, —S($O_2$)$NH_2$, —$SO_2$NHR$^h$, —$SO_2$NR$^h$R$^i$, —PO(OR')$_2$, —$PO_3H_2$, —PO(NR'$_2$)$_2$, —CN, —CH(haloalkyl), —C(O)X', —COOH, —COOR', —C(O)R', —C(O)H, —P(O)(OR')OR", heteroaryl, or aryl; wherein X' is independently halogen, R', R", R$^f$, R$^g$, R$^h$, and R$^i$ are independently hydrogen, alkyl, substituted alkyl, cycloalkyl, or cycloalkyleneNR$^d$R$^e$ (where R$^d$ and R$^e$ are independently hydrogen, alkyl, or cycloalkyl) or R$^f$ and R$^g$ and/or R$^h$ and R$^i$ together with the nitrogen atom to which they are attached form heterocycloamino; and heterocycloamino, aryl and heteroaryl are optionally substituted with one, two or three substituents independently selected from alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl; or (ii) a group of formula (a) or (b);

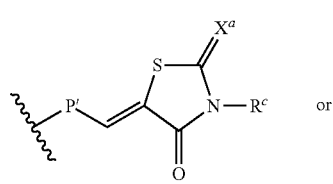

(a)

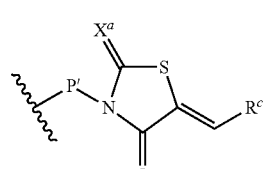

(b)

where P' is bond, alkylene or heteroalkylene, $X^a$ is O or N(H or alkyl) and R$^c$ is hydrogen, alkyl, substituted alkyl, haloalkoxy, cycloalkyl, or cycloalkyleneNR$^d$R$^e$ where R$^d$ and R$^e$ are independently hydrogen, alkyl, or cycloalkyl.

2. The compound or salt of claim 1 wherein the compound of Formula (I') has the structure (Id):

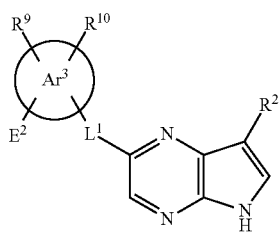

where L¹ is a bond, O or NH, Ar³ is phenyl or heteroaryl, and E² is —P—CH=C(R$^b$)(EWG) or a group of formula (a);

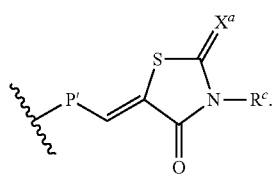

3. The compound or salt of claim 1 wherein the compound of Formula (I') has the structure (If):

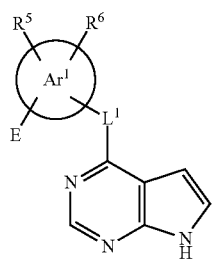

where L¹ is a bond, O or NH, Ar is phenyl or heteroaryl and E is —CH=C(R$^b$)(EWG).

4. The compound or salt of claim 2 wherein E² is a group of formula (a).

5. The compound or salt of claim 2 wherein E² is —P—CH=C(R$^b$)(EWG) where P is bond and EWG is —CO—NR$^f$R$^g$, —SO$_2$NR$^h$R$^i$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and/or R$^h$ and R$^i$ together with the nitrogen atom to which they are attached form heterocycloamino), aryl or heteroaryl wherein said heterocycloamino, aryl and heteroaryl are optionally substituted with one, two or three substituents independently selected from alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

6. The compound or salt of claim 2 wherein E² is —P—CH=C(R$^b$)(EWG) where P is bond and EWG is —C(O)NR$^f$R$^g$, —SO$_2$NR$^h$R$^i$, —COOR', —SO$_2$R' or 5-membered heteroaryl; wherein R' is alkyl, R$^f$ and R$^h$ are independently hydrogen or alkyl, and R$^g$ and R$^h$ are independently alkyl, alkyl substituted with hydroxy, alkoxy, amino, alkylamino or dialkylamino, or R$^f$ and R$^g$ together with the nitrogen atom to which they are attached form heterocycloamino; said heterocycloamino and 5-membered heteroaryl are optionally substituted with one, two or three substituents independently selected from alkyl, alkoxy, hydroxyl, cyano, halo, haloalkyl, haloalkoxy, alkylsulfonyl, carboxy, or alkoxycarbonyl.

7. The compound or salt of claim 3 wherein E is —P—CH=C(R$^b$)(EWG) where P is a bond and EWG is —CO—NR$^f$R$^g$, —SO$_2$NR$^h$R$^i$ (wherein R$^f$ and R$^h$ are independently hydrogen, alkyl, or cycloalkyl and R$^g$ and R$^i$ are independently hydrogen, alkyl, substituted alkyl, or cycloalkyleneNR$^d$R$^e$ (where R$^d$ and R$^e$ are independently hydrogen, alkyl, or cycloalkyl); or R$^f$ and R$^g$ and/or R$^h$ and R$^i$ together with the nitrogen atom to which they are attached form heterocycloamino), aryl or heteroaryl wherein said heterocycloamino, aryl and heteroaryl are optionally substituted with one, two or three substituents independently selected from hydrogen, alkyl, alkoxy, hydroxyl, cyano, nitro, halo, haloalkyl, haloalkoxy, alkylthio, alkylsulfonyl, carboxy, alkoxycarbonyl, aminocarbonyl or aminosulfonyl.

8. The compound or salt of claim 4 wherein R² is acyl.

9. The compound or salt of claim 8 wherein R² is —COR where R is isopropyl, isobutyl, or tert-butyl.

10. The compound or salt of claim 4 wherein R² is aminocarbonyl.

11. The compound or salt of claim 10 wherein R² is —CONHR' where R' is isopropyl, isobutyl, or tert-butyl.

12. The compound or salt of claim 4, wherein P' is a bond and R$^c$ is hydrogen, methyl, ethyl, 2-dimethylaminoethyl or aminoethyl.

13. The compound or salt of claim 6 wherein R² is acyl or aminocarbonyl.

14. The compound or salt of claim 13 wherein R² is —COR or —CONHR' where R and R' are isopropyl, isobutyl, or tert-butyl.

15. The compound or salt of claim 13 wherein R$^b$ is cyano, L¹ is NH, Ar³ is:

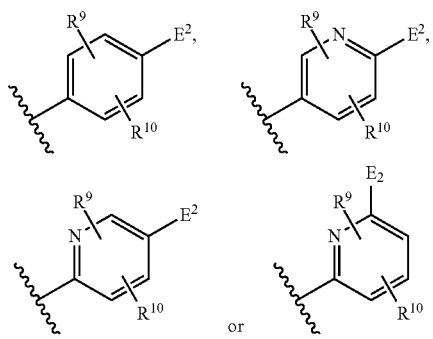

where R⁹ is hydrogen, alkyl, alkoxy, halo, cyano, haloalkyl, or haloalkoxy and R¹⁰ is hydrogen, alkyl, alkoxy, halo, haloalkyl, haloalkoxy, cyano, cycloalkyl, hydroxyalkoxy, alkoxyalkoxy, aminoalkoxy, or alkylsulfonylalkoxy.

16. The compound or salt of claim 15 wherein Ar³ is:

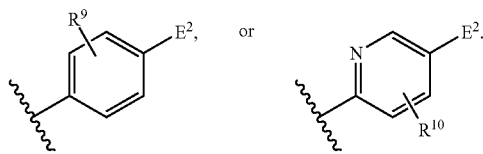

17. The compound or salt of claim 16 wherein R¹⁰ is hydrogen, methyl, methoxy, chloro, fluoro, trifluoromethyl, cyano, 2-methoxyethyloxy, 3-methoxypropyloxy, 2-aminoethyloxy, 3-aminopropyloxy, 2-methylaminoethyloxy, 3-methylaminopropyloxy, 2-dimethylaminoethyloxy, 3-dimethylaminopropyloxy, 2-diethylaminoethyloxy, 3-diethylaminopropyloxy, 2-piperidin-1-ylethyloxy, 3-piperidin-1-ylpropyloxy, 2-piperazin-1-ylethyloxy, 3-piperazin-1-ylpropyloxy, 2-(4-methylpiperazin-1-yl)ethyloxy, 3-(4-methylpiperazin-1-yl)propyloxy, 2-(4-ethylpiperazin-1-yl)ethyloxy, 3-(4-ethylpiperazin-1-yl)propyloxy, 2-morpholin-4-ylethyloxy, 3-morpholin-4-ylpropyloxy, 2-methylsulfonylethyloxy, 3-methylsulfonylpropyloxy, 2-hydroxyethyloxy, or 3-hydroxypropyloxy and is located at carbon ortho to the carbon substituted with E².

18. The compound or salt of claim 17 wherein EWG is —CONH₂, —CONHmethyl, —CONHethyl, —CON(CH₃)₂, isopropylaminocarbonyl, tert-butylaminocarbonyl, 3-hydroxy-1-methylpropylaminocarbonyl, methoxycarbonyl, ethoxycarbonyl, methylsulfonyl, azetidin-1ylcarbonyl, 4-hydroxyazetidin-1-ylcarbonyl, pyrrolidin-1-ylcarbonyl, morpholin-4-ylcarbonyl, 2,6-dimethylmorpholin-4-ylcarbonyl, piperazin-1-ylcarbonyl, 4-methylpiperazin-1-ylcarbonyl, 4-ethylpiperazin-1-ylcarbonyl, piperidin-1-ylcarbonyl, pyrrol-1-yl, pyrazol-1-yl, thiazol-2-yl, oxazol-2-yl, 1,2,4-triazol-1-yl, dimethylaminosulfonyl, or isoxazol-5-yl.

19. A compound selected from the group:
 3-(3-(7H-pyrrolo[2,3-d]pyrimidin-4-yl)phenyl)-2-cyano-N,N-dimethylacrylamide;
 3-(4-(7H-pyrrolo[2,3-d]pyrimidin-4-yl)phenyl)-2-cyano-N,N-dimethylacrylamide;
 3-(3-((7H-pyrrolo[2,3-d]pyrimidin-4-yl)amino)-phenyl)-2-cyano-N,N-dimethyl-acrylamide;
 2-cyano-N,N-dimethyl-3-(3-(methyl(7H-pyrrolo[2,3-d]pyrimidin-4-yl)amino)phenyl)-acrylamide;
 2-cyano-3-(3-(isopropyl(7H-pyrrolo[2,3-d]pyrimidin-4-yl)amino)phenyl)-N,N-dimethyl-acrylamide;
 3-(4-((7H-pyrrolo[2,3-d]pyrimidin-4-yl)amino)-phenyl)-2-cyano-N,N-dimethyl-acrylamide;
 2-cyano-N,N-dimethyl-3-(4-(methyl(7H-pyrrolo[2,3-d]pyrimidin-4-yl)amino)phenyl)-acrylamide;
 2-cyano-3-(4-(isopropyl(7H-pyrrolo[2,3-d]pyrimidin-4-yl)amino)phenyl)-N,N-dimethyl-acrylamide;
 3-(3-((7H-pyrrolo[2,3-d]pyrimidin-4-yl)oxy)phenyl)-2-cyano-N,N-dimethylacrylamide;
 3-(4-((7H-pyrrolo[2,3-d]pyrimidin-4-yl)oxy)phenyl)-2-cyano-N,N-dimethylacrylamide;
 3-(3-((7H-pyrrolo[2,3-d]pyrimidin-4-yl)amino)-2-methoxyphenyl)-2-cyano-N,N-dimethylacrylamide;
 3-(3-((7H-pyrrolo[2,3-d]pyrimidin-4-yl)amino)-2-methylphenyl)-2-cyano-N,N-dimethylacrylamide;
 3-(5-((7H-pyrrolo[2,3-d]pyrimidin-4-yl)amino)-2-chlorophenyl)-2-cyano-N,N-dimethylacrylamide;
 3-(5-((7H-pyrrolo[2,3-d]pyrimidin-4-yl)amino)-2-fluorophenyl)-2-cyano-N,N-dimethylacrylamide;
 3-(5-((7H-pyrrolo[2,3-d]pyrimidin-4-yl)amino)-2-methylphenyl)-2-cyano-N,N-dimethyl-acrylamide;
 3-(5-((7H-pyrrolo[2,3-d]pyrimidin-4-yl)amino)-2-methoxyphenyl)-2-cyano-N,N-dimethyl-acrylamide;
 2-(5-((7H-pyrrolo[2,3-d]pyrimidin-4-yl)amino)-pyridin-2-yl)-3-cyclopropylacrylonitrile;
 3-(3-(5H-pyrrolo[2,3-b]pyrazin-2-yl)phenyl)-2-cyano-N,N-dimethylacrylamide;
 3-(4-(5H-pyrrolo[2,3-b]pyrazin-2-yl)phenyl)-2-cyano-N,N-dimethylacrylamide;
 3-(3-((5H-pyrrolo[2,3-b]pyrazin-2-yl)amino)phenyl)-2-cyano-N,N-dimethylacrylamide;
 3-(4-((5H-pyrrolo[2,3-b]pyrazin-2-yl)amino)phenyl)-2-cyano-N,N-dimethylacrylamide;
 3-(3-((5H-pyrrolo[2,3-b]pyrazin-2-yl)oxy)phenyl)-2-cyano-N,N-dimethylacrylamide;
 3-(4-((5H-pyrrolo[2,3-b]pyrazin-2-yl)oxy)phenyl)-2-cyano-N,N-dimethylacrylamide;
 2-cyano-3-(3-(7-isobutyryl-5H-pyrrolo[2,3-b]pyrazin-2-yl)phenyl)-N,N-dimethyl-acrylamide;
 2-cyano-3-(4-(7-isobutyryl-5H-pyrrolo[2,3-b]pyrazin-2-yl)phenyl)-N,N-dimethyl-acrylamide;
 2-cyano-3-(3-((7-isobutyryl-5H-pyrrolo[2,3-b]pyrazin-2-yl)amino)phenyl)-N,N-dimethylacrylamide;
 2-cyano-3-(4-((7-isobutyryl-5H-pyrrolo[2,3-b]pyrazin-2-yl)amino)phenyl)-N,N-dimethylacrylamide;
 2-cyano-3-(3-((7-isobutyryl-5H-pyrrolo[2,3-b]pyrazin-2-yl)oxy)phenyl)-N,N-dimethyl-acrylamide;
 2-cyano-3-(4-((7-isobutyryl-5H-pyrrolo[2,3-b]pyrazin-2-yl)oxy)phenyl)-N,N-dimethyl-acrylamide;
 2-(3-(2-cyano-3-(dimethylamino)-3-oxoprop-1-en-1-yl)phenyl)-N-isopropyl-5H-pyrrolo-[2,3-b]pyrazine-7-carboxamide;
 2-(4-(2-cyano-3-(dimethylamino)-3-oxoprop-1-en-1-yl)phenyl)-N-isopropyl-5H-pyrrolo-[2,3-b]pyrazine-7-carboxamide;
 2-((3-(2-cyano-3-(dimethylamino)-3-oxoprop-1-en-1-yl)phenyl)amino)-N-isopropyl-5H-pyrrolo[2,3-b]pyrazine-7-carboxamide;
 2-((4-(2-cyano-3-(dimethylamino)-3-oxoprop-1-en-1-yl)phenyl)amino)-N-isopropyl-5H-pyrrolo[2,3-b]pyrazine-7-carboxamide;
 2-(3-(2-cyano-3-(dimethylamino)-3-oxoprop-1-en-1-yl)phenoxy)-N-isopropyl-5H-pyrrolo-[2,3-b]pyrazine-7-carboxamide;
 2-(4-(2-cyano-3-(dimethylamino)-3-oxoprop-1-en-1-yl)phenoxy)-N-isopropyl-5H-pyrrolo-[2,3-b]pyrazine-7-carboxamide;
 2-cyano-N,N-dimethyl-3-(4-((7-pivaloyl-5H-pyrrolo[2,3-b]pyrazin-2-yl)amino)phenyl)-acrylamide;
 2-cyano-N,N-dimethyl-3-(3-((7-pivaloyl-5H-pyrrolo[2,3-b]pyrazin-2-yl)amino)phenyl)-acrylamide;
 2-cyano-3-(4-((7-pivaloyl-5H-pyrrolo[2,3-b]-pyrazin-2-yl)amino)phenyl)acrylamide;
 2-cyano-N-methyl-3-(4-((7-pivaloyl-5H-pyrrolo[2,3-b]pyrazin-2-yl)amino)-phenyl)-acrylamide;
 2-(azetidine-1-carbonyl)-3-(4-((7-pivaloyl-5H-pyrrolo[2,3-b]pyrazin-2-yl)amino)phenyl)-acrylonitrile;
 2-(morpholine-4-carbonyl)-3-(4-((7-pivaloyl-5H-pyrrolo[2,3-b]pyrazin-2-yl)amino)-phenyl)acrylonitrile;
 2-(4-methylpiperazine-1-carbonyl)-3-(4-(7-pivaloyl-5H-pyrrolo[2,3-b]pyrazin-2-yl-amino)-phenyl)acrylonitrile;
 5-(4-(7-pivaloyl-5H-pyrrolo[2,3-b]pyrazin-2-ylamino)benzylidene)thiazolidine-2,4-dione;
 2-cyano-3-(2-fluoro-4-((7-pivaloyl-5H-pyrrolo[2,3-b]pyrazin-2-yl)amino)phenyl)-N,N-dimethylacrylamide;

2-cyano-N,N-dimethyl-3-(6-((7-pivaloyl-5H-pyrrolo[2,3-b]pyrazin-2-yl)amino)pyridin-3-yl)acrylamide;
3-(2-chloro-4-(7-pivaloyl-5H-pyrrolo-[2,3-b]pyrazin-2-ylamino)phenyl)-2-cyano-N,N-dimethylacrylamide;
2-cyano-3-(3-fluoro-4-((7-pivaloyl-5H-pyrrolo[2,3-b]pyrazin-2-yl)amino)phenyl)-N,N-dimethylacrylamide;
2-cyano-N,N-dimethyl-3-(5-((7-pivaloyl-5H-pyrrolo[2,3-b]pyrazin-2-yl)amino)pyridin-2-yl)acrylamide;
N-(tert-butyl)-2-((4-(2-cyano-3-(dimethylamino)-3-oxoprop-1-en-1-yl)phenyl)amino)-5H-pyrrolo[2,3-b]pyrazine-7-carboxamide;
2-((4-(2-cyano-3-(dimethylamino)-3-oxoprop-1-en-1-yl)phenyl)amino)-N-isopropyl-5H-pyrrolo[2,3-b]pyrazine-7-carboxamide;
2-cyano-N,N-dimethyl-3-(5-((7-pivaloyl-5H-pyrrolo[2,3-b]pyrazin-2-yl)amino)thiophen-2-yl)acrylamide;
2-cyano-N-isopropyl-3-(4-((7-pivaloyl-5H-pyrrolo[2,3-b]pyrazin-2-yl)amino)phenyl)-acrylamide;
2-cyano-3-(4-((7-pivaloyl-5H-pyrrolo[2,3-b]pyrazin-2-yl)amino)phenyl)-N-propylacryl-amide;
2-(piperidine-1-carbonyl)-3-(4-((7-pivaloyl-5H-pyrrolo[2,3-b]pyrazin-2-yl)amino)-phenyl)-acrylonitrile;
2-cyano-3-(4-((7-pivaloyl-5H-pyrrolo[2,3-b]pyrazin-2-yl)amino)phenyl)-N-ethyl-acrylamide;
3-ethyl-5-(4-((7-pivaloyl-5H-pyrrolo[2,3-b]pyrazin-2-yl)amino)benzylidene)thiazolidine-2,4-dione;
ethyl 2-cyano-3-(4-((7-pivaloyl-5H-pyrrolo[2,3-b]-pyrazin-2-yl)amino)phenyl)acrylate;
N-(isopropyl)-2-((4-(2-cyano-3-morpholino-3-oxoprop-1-en-1-yl)phenyl)amino)-5H-pyrrolo[2,3-b]pyrazine-7-carboxamide;
2-(methylsulfonyl)-3-(4-((7-pivaloyl-5H-pyrrolo[2,3-b]pyrazin-2-yl)amino)phenyl)-acrylonitrile;
3-(4-((7-pivaloyl-5H-pyrrolo[2,3-b]pyrazin-2-yl)amino)phenyl)-2-(thiazol-2-yl)-acrylonitrile;
2-((4-(2-cyano-3-oxo-3-(piperazin-1-yl)prop-1-en-1-yl)phenyl)amino)-N-isopropyl-5H-pyrrolo[2,3-b]pyrazine-7-carboxamide;
3-methyl-5-(4-((7-pivaloyl-5H-pyrrolo[2,3-b]pyrazin-2-yl)amino)benzylidene)-thiazolidine-2,4-dione;
2-cyano-N-methyl-N-phenyl-3-(4-((7-pivaloyl-5H-pyrrolo[2,3-b]pyrazin-2-yl)amino)-phenyl)-acrylamide;
2-(isoxazol-5-yl)-3-(4-((7-pivaloyl-5H-pyrrolo[2,3-b]pyrazin-2-yl)amino)phenyl)-acrylonitrile;
2-(piperazine-1-carbonyl)-3-(4-((7-pivaloyl-5H-pyrrolo[2,3-b]pyrazin-2-yl)amino)-phenyl)acrylonitrile;
3-(2-(dimethylamino)ethyl)-5-(4-((7-pivaloyl-5H-pyrrolo[2,3-b]pyrazin-2-yl)amino)-benzylidene)thiazolidine-2,4-dione;
3-(2-aminoethyl)-5-(4-((7-pivaloyl-5H-pyrrolo[2,3-b]pyrazin-2-yl)amino)benzylidene)-thiazolidine-2,4-dione;
2-(oxazol-2-yl)-3-(4-((7-pivaloyl-5H-pyrrolo[2,3-b]pyrazin-2-yl)amino)phenyl)-acrylonitrile;
3-(4-((7-pivaloyl-5H-pyrrolo[2,3-b]pyrazin-2-yl)amino)phenyl)-2-(1H-1,2,4-triazol-1-yl)acrylonitrile;
1-cyano-N,N-dimethyl-2-(4-((7-pivaloyl-5H-pyrrolo[2,3-b]pyrazin-2-yl)amino)phenyl)-ethenesulfonamide;
2-((4-(2-cyano-3-(4-methylpiperazin-1-yl)-3-oxoprop-1-en-1-yl)phenyl)amino)-N-isopropyl-5H-pyrrolo[2,3-b]pyrazine-7-carboxamide;
N-(tert-butyl)-2-((4-(2-cyano-3-(4-methylpiperazin-1-yl)-3-oxoprop-1-en-1-yl)phenyl)-amino)-5H-pyrrolo[2,3-b]pyrazine-7-carboxamide;
N-(tert-butyl)-2-((4-(2-cyano-3-morpholino-3-oxoprop-1-en-1-yl)phenyl)amino)-5H-pyrrolo[2,3-b]pyrazine-7-carboxamide;
2-cyano-N,N-dimethyl-3-(4-(7-pivaloyl-5H-pyrrolo[2,3-b]pyrazin-2-yl)phenyl)-acrylamide;
2-cyano-N,N-dimethyl-3-(3-(7-pivaloyl-5H-pyrrolo[2,3-b]pyrazin-2-yl)phenyl)-acrylamide;
2-cyano-N,N-dimethyl-3-(3-((7-pivaloyl-5H-pyrrolo[2,3-b]pyrazin-2-yl)oxy)phenyl)-acrylamide;
2-cyano-N,N-dimethyl-3-(4-((7-pivaloyl-5H-pyrrolo[2,3-b]pyrazin-2-yl)oxy)phenyl)-acrylamide; or (E) or (Z) isomer thereof; or
a pharmaceutically acceptable salt thereof.

20. A pharmaceutical composition comprising a compound of claim 1 or a pharmaceutically acceptable salt thereof; and a pharmaceutically acceptable excipient.

21. A method of treating rheumatoid arthritis, transplantation, psoriasis, psoriatic arthritis, Graft Host disease, ulcerative colitis or Crohn's disease in a patient which method comprises administering to the patient in need thereof, a pharmaceutical composition comprising a compound of claim 1 or a pharmaceutically acceptable salt thereof, and a pharmaceutically acceptable excipient.

22. A pharmaceutical composition comprising a compound of claim 19 or a pharmaceutically acceptable salt thereof; and a pharmaceutically acceptable excipient.

23. A method of treating rheumatoid arthritis, transplantation, psoriasis, psoriatic arthritis, Graft Host disease, ulcerative colitis or Crohn's disease in a patient which method comprises administering to the patient in need thereof, a pharmaceutical composition comprising a compound of claim 19 or a pharmaceutically acceptable salt thereof, and a pharmaceutically acceptable excipient.

\* \* \* \* \*